United States Patent
Akita et al.

(10) Patent No.: US 9,334,482 B2
(45) Date of Patent: May 10, 2016

(54) THERMOPLASTIC RESIN COMPOSITION FOR IMPACT ABSORBING MEMBER AND METHOD FOR PRODUCING SAME

(75) Inventors: Masaru Akita, Nagoya (JP); Shingo Nishida, Nagoya (JP); Hideo Matsuoka, Nagoya (JP); Shigemitsu Suzuki, Nagoya (JP); Yasufumi Morita, Nagoya (JP)

(73) Assignee: Toray Industries, Inc. (JP)

( * ) Notice: Subject to any disclaimer, the term of this patent is extended or adjusted under 35 U.S.C. 154(b) by 220 days.

(21) Appl. No.: 14/234,868

(22) PCT Filed: Jul. 11, 2012

(86) PCT No.: PCT/JP2012/067645
§ 371 (c)(1),
(2), (4) Date: Jan. 24, 2014

(87) PCT Pub. No.: WO2013/015111
PCT Pub. Date: Jan. 31, 2013

(65) Prior Publication Data
US 2014/0142219 A1  May 22, 2014

(30) Foreign Application Priority Data
Jul. 25, 2011  (JP) .................................. 2011-161808

(51) Int. Cl.
*B29C 47/00* (2006.01)
*C08J 3/20* (2006.01)
(Continued)

(52) U.S. Cl.
CPC .............. *C12N 5/166* (2013.01); *C12N 5/0691* (2013.01); *C12N 5/16* (2013.01); *C12N 2500/46* (2013.01); *C12N 2501/06* (2013.01); *C12N 2501/11* (2013.01); *C12N 2501/115* (2013.01); *C12N 2501/73* (2013.01); *C12N 2501/998* (2013.01);
(Continued)

(58) Field of Classification Search
None
See application file for complete search history.

(56) References Cited

U.S. PATENT DOCUMENTS

| 3,306,874 A | 2/1967 | Hay |
| 2006/0211822 A1 | 9/2006 | Varlet et al. |

(Continued)

FOREIGN PATENT DOCUMENTS

| CN | 1205020 A | 1/1999 |
| CN | 101415748 A | 4/2009 |

(Continued)

OTHER PUBLICATIONS

Machine translation of JP 2009-203410.*

Primary Examiner — Mark Kaucher
Assistant Examiner — Kregg Brooks
(74) Attorney, Agent, or Firm — DLA Piper LLP (US)

(57) ABSTRACT

A thermoplastic resin composition includes 1 to 200 parts by weight of an inorganic filler (C) blended with 50 to 80 parts by weight of a thermoplastic resin (A) and 20 to 50 parts by weight of a rubbery polymer having a reactive functional group (B) which together account for 100 parts by weight; wherein the thermoplastic resin (A) and the rubbery polymer having a reactive functional group (B) form a continuous phase and a dispersed phase, respectively, while the inorganic filler (C) is dispersed in the continuous phase and/or the dispersed phase; and the dispersed phase of the rubbery polymer contains fine particles with a diameter of 1 to 100 nm of a compound resulting from a reaction between the thermoplastic resin (A) and the rubbery polymer; and an area occupied by the fine particles account for 10% or more of the dispersed phase.

18 Claims, 2 Drawing Sheets

(51) Int. Cl.

| | | |
|---|---|---|
| C08K 5/09 | (2006.01) | |
| C08K 7/04 | (2006.01) | |
| C08K 7/14 | (2006.01) | |
| C08L 23/12 | (2006.01) | |
| C08L 67/02 | (2006.01) | |
| C08L 67/04 | (2006.01) | |
| C08L 69/00 | (2006.01) | |
| C08L 71/12 | (2006.01) | |
| C08L 77/02 | (2006.01) | |
| C08L 77/06 | (2006.01) | |
| C08L 81/04 | (2006.01) | |
| C08L 101/00 | (2006.01) | |
| C08L 15/00 | (2006.01) | |
| C08L 21/00 | (2006.01) | |
| C12N 5/26 | (2006.01) | |
| C12N 5/16 | (2006.01) | |
| C12N 5/071 | (2010.01) | |

(52) U.S. Cl.
CPC ......... *C12N 2506/00* (2013.01); *C12N 2506/30* (2013.01)

(56) References Cited

U.S. PATENT DOCUMENTS

| | | |
|---|---|---|
| 2008/0015303 A1 | 1/2008 | Eibeck et al. |
| 2009/0118417 A1 | 5/2009 | Tachikawa et al. |
| 2010/0273944 A1 | 10/2010 | Kobayashi et al. |
| 2011/0021707 A1 | 1/2011 | Kobayashi et al. |
| 2012/0028047 A1 | 2/2012 | Imai et al. |

FOREIGN PATENT DOCUMENTS

| | | |
|---|---|---|
| EP | 0 852 249 A1 | 7/1998 |
| JP | 2005-513186 A | 5/2005 |
| JP | 2006-089701 A | 4/2006 |
| JP | 2006-347151 A | 12/2006 |
| JP | 2007-238752 A | 9/2007 |
| JP | 2008-517117 A | 5/2008 |
| JP | 2008-156604 A | 7/2008 |
| JP | 2009-144058 A | 7/2009 |
| JP | 2009-203410 A | 9/2009 |
| JP | 2011-063015 A | 3/2011 |
| JP | 2011-195814 A | 10/2011 |
| WO | 2007/108501 A1 | 9/2007 |
| WO | 2009/119624 A1 | 10/2009 |
| WO | 2010/107022 A1 | 9/2010 |

* cited by examiner

THERMOPLASTIC RESIN COMPOSITION FOR IMPACT ABSORBING MEMBER AND METHOD FOR PRODUCING SAME

TECHNICAL FIELD

This disclosure relates to a thermoplastic resin composition suitable for shock absorbing members that are high in strength, rigidity, and heat resistance and that are resistant to fracture and able to give a high-load square wave in a high speed compression for square prism or other simple shaped molded articles.

BACKGROUND

In recent years, increasing numbers of resin components have come into use to provide lightweight vehicles in the automobile industry. Active research has been performed aiming to develop resin-based shock absorbing interior and exterior members (crushable parts) for automobiles. In load-displacement curves obtained from a high speed compression test assuming automobile collisions, shock absorbing members are required to (1) show a large displacement when the load becomes zero due to destruction and (2) suffer from little change in load attributable to a displacement under a large load (gives a high-load square wave). Many of the approaches attempted at present are focused on specially shaped members such as honeycomb structures, foams, hollow structures, and ribbed molded articles. On the other hand, few efforts are being made in the field of material development, and there are expectations for novel materials.

Major shock absorbing materials include thermoplastic elastomers such as polyurethane. Being low in strength, rigidity, and heat resistance, however, thermoplastic elastomers tend to be useful only for limited uses, and in recent years, many material development efforts are focused on polymer alloys.

Some thermoplastic resin compositions suitable for shock absorbing members have been disclosed, including highly shock absorbing thermoplastic resin compositions produced by blending a thermoplastic resin and a rubbery polymer with a reactive functional group and while controlling the phase structure formation (for example, see Japanese Unexamined Patent Publication Nos. 2006-89701 and 2008-156604). Others disclose polyamide resin compositions high in strength, rigidity, impact resistance, and heat resistance that contain a polyamide resin, inorganic filler, and thermoplastic resin having a reactive functional group, with the inorganic filler and the thermoplastic resin having a reactive functional group independently dispersed in the polyamide resin (for example, see Japanese Unexamined Patent Publication Nos. 2007-238752 and 2009-144058). Also disclosed are fiber reinforced resin compositions consisting mainly of highly shock absorbing resin composition (A) produced by blending resin (A1) with resin (A2) having a reactive functional group while controlling the phase structure formation, as well as resin (B) and fibrous filler (C) (for example, see International Publication WO 2010/107022). In addition, we have disclosed polyamide resin compositions consisting mainly of a highly shock absorbing resin composition produced by blending a polyamide resin with a rubbery polymer having a reactive functional group while controlling the phase structure formation, combined with a dendritic polyester resin, acid anhydride, and glass fiber (for example, see Japanese Unexamined Patent Publication No. 2011-195814).

JP '701 and JP '604 disclosed resin compositions that increase in rupture elongation with an increasing tension speed, but in a high speed compression test for square prism shaped molded articles produced by molding these resin compositions, the load was low. In addition, it was difficult to obtain a square wave although the displacement when load becomes zero was large. Compared to this, the resin compositions described in JP '752 and JP '058 were produced without controlling the reaction between a polyamide resin and a thermoplastic resin with a reactive functional group, and in a high speed compression test for square prism shaped molded articles produced by molding these resin compositions, the displacement when the load becomes zero was small. In addition, it was difficult to obtain a square wave. Furthermore, the resin compositions described in WO '022 contained only a small amount of resin with a reactive functional group, though having a specific phase structure, and in a high speed compression test for square prism shaped molded articles produced by molding these resin compositions, the displacement when the load becomes zero was sometimes small and it was sometimes difficult to obtain a square wave. When these conventional, generally known resin compositions are used to produce shock absorbing members, particularly shock absorbing interior and exterior members for automobiles that receive large energy at the time of a collision, it has been necessary to process them into complicated shapes such as honeycomb structures, foams, hollow structures, and ribbed molded articles, as in the case of conventional materials.

It is thus a major problem to provide a thermoplastic resin composition suitable for shock absorbing members that are high in strength, rigidity, and heat resistance and are resistant to fracture and able to exhibit a high-load square wave in a high speed compression for square prism or other simple shaped molded articles.

SUMMARY

We thus provide a thermoplastic resin composition for shock absorbing members comprising 1 to 200 parts by weight of an inorganic filler (C) blended with 50 to 80 parts by weight of a thermoplastic resin (A) and 20 to 50 parts by weight of a rubbery polymer having a reactive functional group (B) which together account for 100 parts by weight;

having morphological features observed by electron microscopy such that:

the thermoplastic resin (A) and the rubbery polymer having a reactive functional group (B), form a continuous phase and dispersed phase, respectively, while the inorganic filler (C) are dispersed in the continuous phase and/or the dispersed phase; and the dispersed phase (B) of the rubbery polymer having a reactive functional group (B) contains fine particles with a particle diameter of 1 to 100 nm of a compound resulting from a reaction between the thermoplastic resin (A) and the rubbery polymer having a reactive functional group (B); and the area occupied by the fine particles account for 10% or more of the dispersed phase (B); and giving a load-displacement curve meeting all of the requirements (I), (II) and (III) listed below when a square prism specimen with a cross section of 12.7 mm×12.7 mm and a height of 25.4 mm prepared by injection-molding the thermoplastic resin composition in a parallel direction to its height is subjected to a compression test in which a weight with a mass of 26 kg is allowed to fall freely onto the square prism specimen from a height of 0.5 m:

(I) the displacement when load becomes zero is 6 mm or more, (II) the initial load is 12 kN or more and 30 kN or less, and (III) the displacement range included in initial load ±2 kN is 4 mm or more.

It is possible to provide a thermoplastic resin composition with high shock absorbing capability that is high in strength, rigidity, and heat resistance and is resistant to fracture and able to exhibit a high-load square wave in a high speed compression for square prism or other simple shaped molded articles. The use of the thermoplastic resin composition serves to produce a simple shaped shock absorbing member that gives a high-load square wave, thus serving to provide shock absorbing members of a reduced size and cost. The thermoplastic resin composition for shock absorbing members can be melt-molded to provide molded articles that are particularly preferred for use as shock absorbing interior and exterior members for automobiles.

Figure 1:
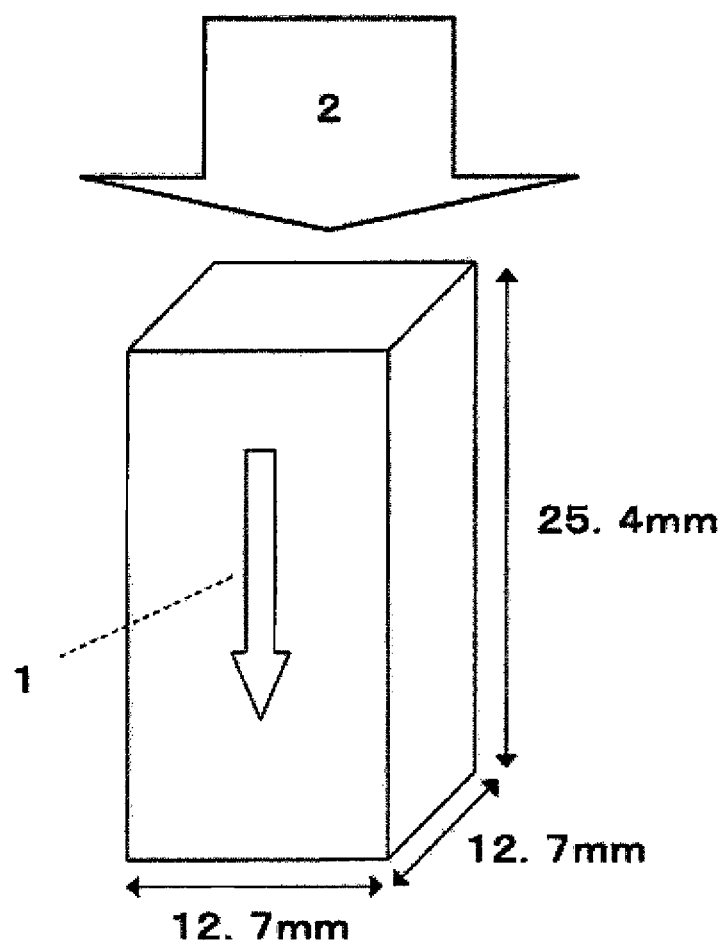
FIG. 1 is an illustrative diagram of a square prism specimen to be used for the high speed compression test.

EXPLANATION OF NUMERALS (a) displacement when load becomes zero
(b) initial load
(c) displacement range included in initial load ±2 kN
1: flow direction of thermoplastic resin composition during injection molding
2: direction of compression
3: notch
4: screw pitch
5: screw diameter D

DETAILED DESCRIPTION

Our compositions and methods are described in more detail below.

The thermoplastic resin composition for the shock absorbing members (hereinafter, referred to as thermoplastic resin composition) is produced by blending a thermoplastic resin (A), a rubbery polymer having a reactive functional group (B), and an inorganic filler (C).

There are no specific limitations on the resin to be used as the thermoplastic resin (A) as long as it can be molded by melting under heat. The addition of the thermoplastic resin (A) to the thermoplastic resin composition serves to provide a square prism shaped molded article that develops a high load in the high speed compression. The resins that are favorable as thermoplastic resin (A) include, for example, polyamide resins, polyester resins, polyphenylene sulfide resins, polyphenylene oxide resins, polycarbonate resins, polylactic acid resins, polyacetal resins, polysulfone resins, polytetrafluoroethylene resins, polyetherimide resins, polyamide-imide resins, polyimide resins, polyethersulfone resins, polyether ketone resins, polythioether ketone resins, polyether ether ketone resins, polyethylene resins, polypropylene resins, styrene based resins such as polystyrene resins, acrylonitrile/butadiene/styrene copolymers (ABS resin), and polyalkylene oxide resins. A plurality thereof may be combined unless their characteristics are impaired.

Of the thermoplastic resins listed above, preferred ones include polyamide resins, polyester resins, polyphenylene sulfide resins, polyphenylene oxide resins, polycarbonate resins, polylactic acid resins, and polypropylene resins. Polyamide resins, polyester resins, polyphenylene sulfide resins, and polyphenylene oxide resins are more preferable, and polyamide resins are still more preferable, because of having a highly reactive end group.

The polyamide resins are those of polymers having an amide bond which are produced from an amino acid, lactam or diamine and dicarboxylic acid as main raw materials. Such raw materials include amino acids such as 6-aminocaproic acid, 11-aminoundecanoic acid, 12-aminododecanoic acid, and para-aminomethyl benzoic acid; lactams such as ε-caprolactam and ω-laurolactam; aliphatic diamines such as tetramethylene diamine, pentamethylene diamine, hexamethylene diamine, 2-methyl pentamethylene diamine, nonamethylene diamine, decamethylene diamine, undecamethylene diamine, dodecamethylene diamine, 2,2,4-/2,4,4-trimethyl hexamethylene diamine, and 5-methyl nonamethylene diamine; aromatic diamines such as meta-xylylene diamine and para-xylylene diamine; alicyclic diamines such as 1,3-bis(aminomethyl)cyclohexane, 1,4-bis(aminomethyl)cyclohexane, 1-amino-3-aminomethyl-3,5,5-trimethylcyclohexane, bis(4-aminocyclohexyl)methane, bis(3-methyl-4-aminocyclohexyl)methane, 2,2-bis(4-aminocyclohexyl)propane, bis(aminopropyl)piperazine, and aminoethyl piperazine; aliphatic dicarboxylic acids such as adipic acid, suberic acid, azelaic acid, sebacic acid, and dodecanedioic acid; aromatic dicarboxylic acids such as terephthalic acid, isophthalic acid, 2-chloroterephthalic acid, 2-methyl terephthalic acid, 5-methyl isophthalic acid, 5-sodium sulfoisophthalic acid, 2,6-naphthalene dicarboxylic acid, hexahydroterephthalic acid, and hexahydroisophthalic acid; and alicyclic dicarboxylic acids such as cyclohexane dicarboxylic acid. A plurality of polyamide homopolymers or copolymers derived from these raw materials may be added.

Particularly useful polyamide resins are polyamide resins that have a crystal melting point of 150° C. or more and have a high heat resistance and strength. Specific polyamide resins having a crystal melting point of 150° C. or more include polycaproamide (polyamide 6), polyhexamethylene adipamide (polyamide 66), polypentamethylene adipamide (polyamide 56), polytetramethylene adipamide (polyamide 46), polyhexamethylene sebacamide (polyamide 610), polypentamethylene sebacamide (polyamide 510), polytetramethylene sebacamide (polyamide 410), polyhexamethylene dodecamide (polyamide 612), polyundecane amide (polyamide 11), polydodecane amide (polyamide 12), polycaproamide/polyhexamethylene adipamide copolymer (polyamide 6/66), polycaproamide/polyhexamethylene terephthalamide copolymer (polyamide 6/6T), polyhexamethylene adipamide/polyhexamethylene terephthalamide copolymer (polyamide 66/6T), polyhexamethylene adipamide/polyhexamethylene isophthalamide copolymer (polyamide 66/6I), polyhexamethylene adipamide/polyhexamethylene isophthalamide/polycaproamide copolymer (polyamide 66/6I/6), polyhexamethylene terephthalamide/polyhexamethylene isophthalamide copolymer (polyamide 6T/6I), polyhexamethylene terephthalamide/polydecane amide copolymer (polyamide 6T/12), polyhexamethylene adipamide/polyhexamethylene terephthalamide/polyhexamethylene isophthalamide copolymer (polyamide 66/6T/6I), polyxylylene adipamide (polyamide XD6), polyhexamethylene terephthalamide/poly-2-methyl pentamethylene terephthalamide copolymer (polyamide 6T/M5T), polyhexamethylene terephthalamide/polypentamethylene terephthalamide copolymer (polyamide 6T/5T), polypentamethylene terephthalamide/polypentamethylene adipamide copolymer (5T/56), polynonamethylene terephthalamide (polyamide 9T), polydecamethylene terephthalamide (polyamide 10T), as well as mixtures thereof and copolymers thereof "/" indicates a copolymer, and this applies hereinafter.

Particularly preferable ones include polyamide 6, polyamide 66, polyamide 56, polyamide 610, polyamide 510, polyamide 410, polyamide 612, polyamide 11, polyamide 12, polyamide 6/66, polyamide 66/6T, polyamide 6T/6I, polyamide 66/6I/6, and polyamide 6T/5T. It is also practically preferable to add a plurality of these polyamide resins to develop required characteristics including moldability, heat resistance, toughness, and surface properties. Of these, polyamide 6, polyamide 66, polyamide 610, polyamide 11, polyamide 12, and polyamide 66/6T are the most preferable because they have strength, rigidity, heat resistance, and injection moldability in a good balance and a square prism shaped molded articles produced by melt molding of a thermoplastic resin composition containing these polyamide resins can give a larger displacement when load becomes zero and a larger initial load in high speed compression.

There are no specific limitations on the quantity of the end groups in these polyamide resins, but it is preferable that $3 \times 10^{-5}$ mol/g or more of contained amino end groups be contained to ensure required reactivity with the rubbery polymer having a reactive functional group (B). The quantity of the amino end groups can be determined by dissolving the polyamide resin in an 85 wt % phenol-ethanol solution and titrating it with a hydrochloric acid aqueous solution using thymol blue as indicator.

There are no specific limitations on the degree of polymerization of these polyamide resins, but it is preferable for their relative viscosity to be 1.5 to 7.0. The relative viscosity as referred to herein is determined in a 98% concentrated sulfuric acid solution with a polyamide resin concentration of 0.01 g/ml at 25° C. If the relative viscosity is 1.5 or more, square prism shaped molded articles prepared by melt molding of the thermoplastic resin composition will be larger in the displacement when load becomes zero in the high speed compression. It is more preferably 1.8 or more. If the relative viscosity is 7.0 or less, on the other hand, the thermoplastic resin composition will have a melt viscosity in an appropriate range and will be melt-molded easily. It is more preferably 6.0 or less.

Polyester resins are those of polymers having ester bonds in the backbone chain. The polyester resins include polymers and copolymers produced by condensation reaction of dicarboxylic acid (or its ester-forming derivative) and a diol (or its ester-forming derivative) used as primary components. However, the dendritic polyester resin (E), which is described later, is excluded. A plurality of these polyester resins may be added.

The dicarboxylic acids and their ester-forming derivatives as described above include, for example, aromatic dicarboxylic acids such as terephthalic acid, isophthalic acid, phthalic acid, 2,6-naphthalene dicarboxylic acid, 1,5-naphthalene dicarboxylic acid, bis(p-carboxyphenyl)methane, anthracene dicarboxylic acid, 4,4'-diphenyl ether dicarboxylic acid, and 5-sodium sulfoisophthalic acid; aliphatic dicarboxylic acids such as adipic acid, sebacic acid, azelaic acid, and dodecanedioic acid; alicyclic dicarboxylic acids such as 1,3-cyclohexanedicarboxylic acid and 1,4-cyclohexanedicarboxylic acid, and ester-forming derivatives thereof. Furthermore, the diols and ester-forming derivatives thereof include, for example, aliphatic glycols with a carbon number of 2 to 20 such as ethylene glycol, propylene glycol, 1,4-butanediol, neopentyl glycol, 1,5-pentanediol, 1,6-hexanediol, and deca-methylene glycol; alicyclic glycols with a carbon number of 2 to 20 such as cyclohexanedimethanol and cyclohexanediol; long chain glycols with a molecular weight of 400 to 6,000 such as polyethylene glycol, poly-1,3-propylene glycol, and polytetramethylene glycol; and ester-forming derivatives thereof.

Preferable polymers and copolymers thereof include polybutylene terephthalate, polybutylene (terephthalate/isophthalate), polybutylene (terephthalate/adipate), polybutylene (terephthalate/sebacate), polybutylene (terephthalate/decane dicarboxylate), polybutylene naphthalate, polyethylene terephthalate, polyethylene (terephthalate/isophthalate), polyethylene (terephthalate/adipate), polyethylene (terephthalate/5-sodium sulfoisophthalate), polybutylene (terephthalate/5-sodium sulfoisophthalate), polyethylene naphthalate, and polycyclohexane dimethylene terephthalate. From the viewpoint of the moldability of the obtainable thermoplastic resin compositions, more preferable are polybutylene terephthalate, polybutylene (terephthalate/adipate), polybutylene (terephthalate/decane dicarboxylate), polybutylene naphthalate, polyethylene terephthalate, polyethylene (terephthalate/adipate), polyethylene naphthalate, and polycyclohexane dimethylene terephthalate, of which polybutylene terephthalate (polybutylene terephthalate resin) is still more preferable.

The polybutylene terephthalate resins preferably have an intrinsic viscosity of 0.35 to 2.00, more preferably 0.50 to 1.50. It can be practical to combine polybutylene terephthalate resins that are different in intrinsic viscosity. The intrinsic viscosity as referred to herein is determined in an o-chlorophenol solution with a polybutylene terephthalate resin concentration of 0.5 wt % at 25° C.

Furthermore, the quantity of carboxyl end groups in a polybutylene terephthalate resin (quantity of end groups per ton of the polymer) is preferably 1 to 50 eq/t from the viewpoint of the reactivity with the rubbery polymer having a reactive functional group (B). The quantity of carboxyl end groups is determined by performing potentiometric titration of a m-cresol solution of the polybutylene terephthalate resin with an alkali solution.

The polyphenylene sulfide resins are polymers having a structural unit as represented by structural formula below:

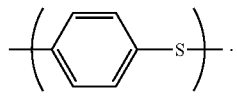

From the viewpoint of heat resistance, p-phenylene sulfide units as represented by the above structural formula preferably account for 70 mol % or more, more preferably 90 mol % or more, of all structural units. For the polyphenylene sulfide resin, less than 30 mol % of its structural units may be accounted for by structural units having structures as shown below:

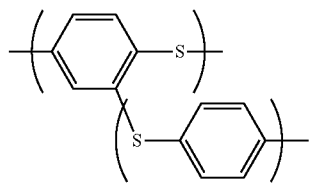

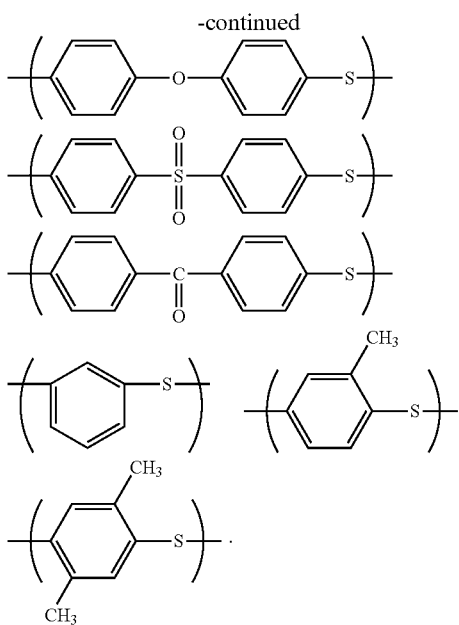

For the polyphenylene sulfide resins, there are no specific limitations on their melt viscosity as long as they can be melt-kneaded, but it is preferable for their melt flow rate (MFR) to be 30 to 30,000 g/30 min, more preferably 150 to 15,000 g/30 min (under a load of 5 kg at 315.5° C.).

Specific examples of polyphenylene oxide resins include poly(2,6-dimethyl-1,4-phenylene oxide), poly(2-methyl-6-ethyl-1,4-phenylene oxide), poly(2,6-diphenyl-1,4-phenylene oxide), poly(2-methyl-6-phenyl-1,4-phenylene oxide), poly(2,6-dichloro-1,4-phenylene oxide), and copolymers of 2,6-dimethyl phenol with other phenols (for example, 2,3,6-trimethyl phenol). In particular, poly(2,6-dimethyl-1,4-phenylene oxide) and the copolymer of 2,6-dimethyl phenol and 2,3,6-trimethyl phenol are preferable, of which poly(2,6-dimethyl-1,4-phenylene oxide) is particularly preferable.

The polyphenylene oxide resins preferably have a reduced viscosity of 0.15 to 0.70. The reduced viscosity referred to herein is determined in a chloroform solution with a polyphenylene oxide resin concentration of 0.5 g/dl at 30° C.

There are no specific limitations on the method to be used for the production of a polyphenylene oxide resin, and a generally known method may be used. For example, a polyphenylene oxide resin can be produced easily by oxidative polymerization of phenols using a complex of a cuprous salt and an amine as catalyst as proposed by Hay in U.S. Pat. No. 3,306,874. Needless to say, a polyphenylene oxide resin as produced above may be modified, activated, or subjected other various treatments with functional groups such as an acid anhydride group, epoxy group, isocyanate group, and other compounds before being used.

A polycarbonate resin may be produced easily by reacting an aromatic dihydroxy compound with carbonate precursors such as phosgene or carbonic acid diesters. For the reaction, generally known methods may be adopted such as the interface method when using phosgene and the ester interchange method when a carbonic acid diester is used for reaction in a molten state.

A major aromatic dihydroxy compound as described above is 2,2-bis(4-hydroxy-phenyl)propane [bisphenol A]. Others include, for example, bis(hydroxyaryl)alkanes such as bis(4-hydroxyphenyl)methane, 1,1-bis(4-hydroxyphenyl)ethane, 2,2-bis(4-hydroxyphenyl)butane, 2,2-bis(4-hydroxyphenyl) octane, bis(4-hydroxyphenyl)phenyl methane, 2,2-bis(4-hydroxy-3-methylphenyl)propane, 1,1-bis(4-hydroxy-3-t-butyl phenyl)propane, 2,2-bis(4-hydroxy-3-bromophenyl)propane, 2,2-bis(4-hydroxy-3,5-dibromophenyl)propane, 2,2-bis(4-hydroxy-3,5-dichlorophenyl)propane; bis(hydroxyaryl)cycloalkanes such as 1,1-bis(4-hydroxyphenyl) cyclopentane and 1,1-bis(4-hydroxyphenyl)cyclohexane; dihydroxy diaryl ethers such as 4,4'-dihydroxydiphenyl ethers and 4,4'-dihydroxy-3,3'-dimethyldiphenyl ethers; dihydroxy diaryl sulfides such as 4,4'-dihydroxydiphenyl sulfide and 4,4'-dihydroxy-3,3'-dimethyldiphenyl sulfide; dihydroxy diaryl sulfoxides such as 4,4'-dihydroxydiphenyl sulfoxide and 4,4'-dihydroxy-3,3'-dimethyldiphenyl sulfoxide; and dihydroxy diaryl sulfones such as 4,4'-dihydroxy diphenyl sulfone and 4,4'-dihydroxy-3,3'-dimethyl diphenyl sulfone. Two or more thereof may be combined. Piperazine, dipiperidyl hydroquinone, resorcin, and 4,4'-dihydroxy diphenyl may be used in combination therewith. It is also possible to use a branched aromatic polycarbonate resin that is combined with a polyfunctional compound such as phloroglucin.

Carbonate precursors to be reacted with an aromatic dihydroxy compound include, for example, phosgene; diaryl carbonates such as diphenyl carbonate, ditolylcarbonate; and alkyl carbonates such as dimethyl carbonate and diethyl carbonate.

The polycarbonate resins preferably have a molecular weight of 10,000 to 50,000. The molecular weight referred to herein is the viscosity average molecular weight converted from the viscosity of a methylene chloride solution of a polycarbonate resin at a temperature of 25° C.

The methods serving to produce an aromatic polycarbonate resin with an intended molecular weight include, for example, generally known methods such as the use of an end stopping agent or molecular weight modifier and the use of appropriately selected polymerization reaction conditions.

The polylactic acid resins are polymers containing a L-lactic acid and/or D-lactic acid as main constituents and may contain copolymerization components other than lactic acids. Such other copolymerization components include glycol compounds such as ethylene glycol, propylene glycol, butanediol, heptanediol, hexanediol, octanediol, nonanediol, decanediol, 1,4-cyclohexane dimetanol, neopentyl glycol, glycerin, pentaerythritol, bisphenol A, polyethylene glycol, polypropylene glycol, and polytetramethylene glycol; dicarboxylic acids such as oxalic acid, adipic acid, sebacic acid, azelaic acid, dodecanedioic acid, malonic acid, glutaric acid, cyclohexanedicarboxylic acid, terephthalic acid, isophthalic acid, phthalic acid, naphthalene dicarboxylic acid, bis(p-carboxyphenyl)methane, anthracene dicarboxylic acid, 4,4'-diphenyl ether dicarboxylic acid, 5-sodium sulfoisophthalic acid, and 5-tetrabutyl phosphonium isophthalic acid; hydroxycarboxylic acids such as glycolic acid, hydroxypropionic acid, hydroxybutyric acid, hydroxyvaleric acid, hydroxycaproic acid, and hydroxybenzoic acid; and lactones such as caprolactone, valerolactone, propiolactone, undecalactone, and 1,5-oxepane-2-one. Commonly, these copolymerization components preferably account for 30 mol % or less, more preferably 10 mol % or less, of all the monomer components.

It is preferable to use a polylactic acid with a high optical purity of the lactic acid components from injection moldability. Specifically, of all the lactic acid components of the polylactic acid, it is preferable that the L-form components account for 80% or more or the D-form components account for 80% or more; it is more preferable that the L-form components account for 90% or more or the D-form components account for 90% or more; and it is still more preferable that the L-form components account for 95% or more or the D-form components account for 95% or more. Furthermore, it is preferable to use polylactic acid with a high optical purity composed mainly of L-form or D-form components as primary components or also preferable to use them in combination.

Such a polylactic acid resin preferably has a weight average molecular weight of 100,000 to 270,000. The weight average molecular weight referred to herein is a polymethyl methacrylate (PMMA) based molecular weight determined gel permeation chromatography using hexafluoroisopropanol as eluent.

A polylactic acid resin can be produced by a generally known polymerization method such as direct polymerization from a lactic acid and ring opening polymerization via a lactide.

The polypropylene resins are polymers containing propylene as main constituents. They may have any of the homo, block, and random structures, but it is preferable to use a homopolypropylene resin to produce a square prism shaped molded article that can develop a higher load in high speed compression. The polypropylene resins preferably have a functional group introduced at a chain end or in the backbone chain. The useful functional groups include amino group, carboxyl group, carboxyl metal salt, hydroxyl group, epoxy group, acid anhydride group, isocyanate group, mercapto group, oxazoline group, and sulfonic acid group, a plurality of which may be contained.

There are no specific limitations on the method to be used to introduce an acid anhydride group into a polypropylene resin, and commonly, a generally known technique such as grafting an acid anhydride on a polypropylene resin, may be used. For example, an acid anhydride group can be introduced into a polypropylene resin by dry-blending 0.1 to 10 parts by weight of maleic anhydride and 0.01 to 1 parts by weight of a radical-generating agent with 100 parts by weight of a polypropylene resin and melt-kneaded together at a cylinder temperature of 200 to 230° C.

The rubbery polymer that constitutes the rubbery polymer having a reactive functional group (B) is a polymer having a glass transition temperature lower than room temperature and in which part of the molecules are mutually restrained by covalent bonds, ionic bonds, van der Waals force, entanglement and the like. The addition of the rubbery polymer (B) to the thermoplastic resin composition serves to provide a square prism shaped molded article that has an increased displacement when load becomes zero in the high speed compression. Substances useful as rubbery polymer (B) include, for example, diene based rubbers such as polybutadiene, polyisoprene, styrene/butadiene random or block copolymer, hydrogenated products of the aforementioned block copolymer, acrylonitrile/butadiene copolymers, and butadiene/isoprene copolymer; ethylene/propylene random or block copolymer; ethylene/butene random or block copolymer; ethylene/α-olefin copolymer; ethylene/unsaturated carboxylate copolymers such as ethylene/acrylate, and ethylene/methacrylate; acrylate/butadiene copolymers such as butyl acrylate/butadiene copolymer; copolymers of ethylene and fatty acid vinyl such as ethylene/vinyl acetate copolymer; ethylene/propylene/nonconjugated diene ternary copolymers such as ethylene/propylene/ethylidene norbornene copolymer and ethylene/propylene/hexadiene copolymer; butylene/isoprene copolymer; chlorinated polyethylene; and thermoplastic elastomers such as polyamide elastomer, and polyester elastomer.

In particular, in the case where a polyamide resin is used as thermoplastic resin (A), the use of an ethylene/unsaturated carboxylate copolymer is preferred from the viewpoint of compatibility. Useful unsaturated carboxylates include (meth)acrylates, and esters of (meth)acrylic acid and alcohol are preferred. Specific examples of such (meth)acrylates include methyl (meth)acrylate, ethyl (meth)acrylate, 2-ethylhexyl(meth)acrylate, and stearyl(meth)acrylate. There are no specific limitations on the weight ratio between the ethylene component and the unsaturated carboxylate component in a copolymer, but it is preferably 90/10 to 10/90, more preferably 85/15 to 15/85. There are no specific limitations on the number average molecular weight of the ethylene/unsaturated carboxylate copolymer, but it is preferably 1,000 to 70,000. There are no specific limitations on the melt viscosity of the ethylene/unsaturated carboxylate copolymer as long as it can be melt-kneaded, but its melt flow rate (MFR) is preferably 0.1 to 500 g/10 min, more preferably 1 to 100 g/10 min, (190° C., 2.16 kg load) from the viewpoint of the flowability the thermoplastic resin composition and the mechanical characteristics of molded articles.

There are no specific limitations on the reactive functional group existing in the rubbery polymer having a reactive functional group (B) as long as it reacts with the functional group existing in the thermoplastic resin (A). The useful reactive functional groups include, for example, epoxy group, acid anhydride group, amino group, carboxyl group, carboxyl metal salt, oxazoline group, hydroxyl group, isocyanate group, mercapto group, and sulfonic acid group. Two or more thereof may be contained. Of these, epoxy group, acid anhydride group, amino group, carboxyl group, carboxyl metal salt, and oxazoline group are preferred because of having high reactivity and less liable to side reactions such as decomposition and crosslinking. In the case where a polyamide resin is used as thermoplastic resin (A), in particular, it is preferable for the rubbery polymer (B) to have an epoxy group, acid anhydride group, or carboxyl group that are highly reactive with the terminal amino group in the polyamide resin.

The useful acid anhydrides for the acid anhydride group include, for example, maleic anhydride, itaconic anhydride, endic anhydride, citraconic anhydride, and 1-butene-3,4-dicarboxylic anhydride. A plurality thereof may be used in combination. Of these, maleic anhydride and itaconic anhydride are preferred.

There are no specific limitations on the method to be used to introduce an acid anhydride group into a rubbery polymer, but commonly, a generally known technique can be used such as copolymerizing an acid anhydride with a monomer that serve as raw material for the rubbery polymer and grafting an acid anhydride on a rubbery polymer.

There are no specific limitations on the method to be used to introduce an epoxy group into a rubbery polymer, but commonly, a generally known technique can be used such as copolymerizing a vinylic monomer containing an epoxy group with a monomer that serve as raw material for the rubbery polymer, using a polymerization initiator or chain transfer agent containing an epoxy group to polymerize a rubbery polymer, and grafting an epoxy compound on a rubbery polymer. Such vinylic monomers containing an epoxy group include, for example, glycidyl ester compounds of α,β-unsaturated acids such as glycidyl acrylate, glycidyl methacrylate, glycidyl ethacrylate, and glycidyl itaconate.

There are no specific limitations on the method to be used to introduce an oxazoline group into a rubbery polymer, but commonly, a generally known technique can be used such as copolymerizing a vinylic monomer containing an oxazoline group with a monomer that serve as raw material for the rubbery polymer. Such vinylic monomers containing an oxazoline group include, for example, 2-isopropenyl-oxazoline, 2-vinyl-oxazoline, 2-acryloyl-oxazoline, and 2-styryl-oxazoline.

There are no specific limitations on the method to be used to introduce an amino group into a rubbery polymer, but commonly, a generally known technique can be used such as copolymerizing a vinylic monomer containing an amino group with a monomer that serve as raw material for the rubbery polymer and grafting an amino group-containing compound on a rubbery polymer.

There are no specific limitations on the method to be used to introduce a carboxyl group into a rubbery polymer, but commonly, a generally known technique can be used such as copolymerizing an unsaturated carboxylic acid based monomer containing a carboxyl group with a monomer that serve as raw material for the rubbery polymer. Such unsaturated carboxylic acids include, for example, (meth)acrylic acid.

A carboxyl metal salt produced by converting at least part of the carboxyl group into a metal salt may be effective as reactive functional group, and the examples thereof include metallic (meth)acrylates. There are no specific limitations on the metal in the metal salt to be used, and preferable ones include alkali metals such as sodium, alkaline earth metals such as magnesium, and zinc. Rubbery polymers containing a metallic carboxylate as reactive functional group include, for example, ethylene/unsaturated carboxylic acid/unsaturated metallic carboxylate copolymers such as ethylene/acrylic acid/metallic acrylate copolymer and ethylene/methacrylic acid/metallic methacrylate copolymer. There are no specific limitations on the weight ratio between the unsaturated carboxylic acid component and the unsaturated metallic carboxylate component in a copolymer, but it is preferably 95/5 to 5/95, more preferably 90/10 to 10/90.

There are no specific limitations on the number of functional groups included in one molecular chain of the rubbery polymer having a reactive functional group (B), but commonly it is preferably 1 to 10, and more preferably 1 to 5, to reduce side reactions such as crosslinking. Some molecular chains may completely free of functional groups, but their proportion should be as small as possible.

With respect to the blending quantities of the thermoplastic resin (A) and the rubbery polymer having a reactive functional group (B) in the thermoplastic resin composition, the thermoplastic resin (A) accounts for 50 to 80 parts by weight while the rubbery polymer having a reactive functional group (B) accounts for 20 to 50 parts by weight. If the blending quantity of the rubbery polymer having a reactive functional group (B) is less than 20 parts by weight, square prism shaped molded articles prepared by melt molding of the thermoplastic resin composition will be small in the displacement when load becomes zero or small in the displacement range included in initial load ±2 kN in the high speed compression. For such square prism shaped molded articles to show a larger displacement when load becomes zero and a larger displacement range included in initial load ±2 kN in the high speed compression, the components of (A) and (B) preferably account for 75 or less parts by weight and 25 or more parts by weight, respectively, more preferably 70 or less parts by weight and 30 or more parts by weight, respectively. If the blending quantity of the component of (B) accounts for more than 50 parts by weight, on the other hand, square prism shaped molded articles prepared by melt molding of the thermoplastic resin composition will become lower in the initial load in the high speed compression. To further improve the load in the high speed compression, the components of (A) and (B) preferably account for 55 or more parts by weight and 45 or less parts by weight, respectively, more preferably 60 or more parts by weight and 40 or less parts by weight, respectively.

The thermoplastic resin composition is characterized by further comprising an inorganic filler (C). The addition of an inorganic filler (C) to the thermoplastic resin composition serves for molded articles produced from the thermoplastic resin composition to have high strength, rigidity, and heat resistance and furthermore, give a high-load square wave in the high speed compression for square prism shaped molded specimens. Specifically, molded articles produced by melt molding of the thermoplastic resin composition will show an improved initial load in the high speed compression and can deform while maintaining the initial load. With respect to its configuration, the inorganic filler (C) may be either fibrous or nonfibrous, but it is preferably fibrous to develop a higher load. It is also practical to use a fibrous inorganic filler and a nonfibrous inorganic filler in combination.

Useful inorganic fillers include, for example, fibrous inorganic fillers such as glass fiber, carbon fiber, potassium titanate whisker, zinc oxide whisker, aluminum borate whisker, alumina fiber, silicon carbide fiber, ceramic fiber, asbestos fiber, gypsum fiber, metal fiber; metal silicates such as wollastonite, zeolite, sericite, kaolin, mica, clay, pyrophyllite, bentonite, asbestos, talc, and alumina silicate; metal oxides such as alumina, silicon oxide, magnesium oxide, zirconium oxide, titanium oxide, and iron oxide; carbonates such as calcium carbonate, magnesium carbonate, and dolomite; metal sulfates such as calcium sulfate and barium sulfate; metal hydroxides such as magnesium hydroxide, calcium hydroxide, and aluminum hydroxide; and nonfibrous inorganic fillers such as glass beads, ceramic beads, boron nitride, and silicon carbide, which may be in a hollow form. A plurality of these inorganic fillers may be used in combination. Furthermore, these fibrous and/or nonfibrous inorganic fillers may be subjected to preliminary treatment with a coupling agent such as isocyanate based compound, organic silane based compound, organic titanate based compound, organic borane based compound, and epoxy compound, which can further improve the load in the high speed compression.

Of the inorganic fillers listed above, glass fiber, carbon fiber, wollastonite, kaolin, mica, clay, talc, alumina, and glass beads are preferable. Glass fiber, in particular, is used more favorably because square prism shaped molded articles will easily give a high-load square wave in the high speed compression.

There are no specific limitations on the glass fiber, and generally known material can be used. Different types of glass fiber, including chopped strands with a predetermined length, roving strands, and milled fiber, and generally, those with an average fiber diameter of 5 to 15 μm are used favorably. When using chopped strands, there are no specific limitations on their fiber length, but glass fiber with a strand length of 3 mm is used favorably because of high in workability for extrusion and kneading. When using roving strands, the generally known technique of feeding roving strands directly into an extruder is used to produce a composite material. A plurality of these glass fibers may be used in combination.

There are no specific limitations on the carbon fiber, and generally known various carbon fibers including such as carbonaceous fibers produced from, for example, polyacrylonitrile (PAN), pitch, rayon, lignin, or hydrocarbon gas, as well as graphite fiber and other ones produced by coating these fibers with metal. In particular, PAN-based carbon fiber can be used favorably because improved mechanical characteristics can be expected. Carbon fibers are commonly in the form of chopped strands with a predetermined length, roving strands, and milled fibers, which have a diameter of 15 μm or less, preferably 5 to 10 μm. When using chopped strands, there are no specific limitations on their fiber length, but it is preferable to use those with a strand length that ensures high workability for extrusion and kneading. When using roving strands, the generally known technique of feeding roving strands directly into an extruder is used to produce a composite material. It is preferable to use chopped strands, and the carbon fiber strands used as precursor for chopped carbon fiber is preferably composed of 1,000 to 150,000 filaments from the viewpoint of production cost and stability in the production process.

The blending quantity of the inorganic filler (C) in the thermoplastic resin composition is 1 to 200 parts by weight relative to the total quantity, or 100 parts by weight, of the thermoplastic resin (A) and the rubbery polymer having a reactive functional group (B). If the blending quantity of the inorganic filler (C) accounts for less than 1 part by weight, square prism shaped molded articles prepared by melt molding of the thermoplastic resin composition will be low in the initial load in the high speed compression and will have difficulty in giving a square wave. It is preferably 10 or more parts by weight and more preferably 20 or more parts by weight. If the blending quantity of the inorganic filler (C) is more than 200 parts by weight, on the other hand, the thermoplastic resin composition will increase melt viscosity considerably and will not be easily processed into molded articles. It is preferably 150 or less parts by weight and more preferably 100 or less parts by weight.

When observed by electron microscopy, the thermoplastic resin composition is mainly composed of a continuous phase of the thermoplastic resin (A) and a dispersed phase of the rubbery polymer having a reactive functional group (B), with the inorganic filler (C) being dispersed in the continuous phase and/or dispersed phase, and at the same time, has morphological features such that the dispersed phase (B) of the rubbery polymer having a reactive functional group contains fine particles with a particle diameter of 1 to 100 nm of a compound resulting from a reaction between the thermoplastic resin (A) and the rubbery polymer having a reactive functional group (B), with the area occupied by the fine particles accounting for 10% or more of the entire dispersed phase (B). The state in which the inorganic filler (C) is dispersed in the continuous phase and/or dispersed phase may be hereinafter referred to as the formation of a dispersed phase by the inorganic filler (C). The compound produced by a reaction between the thermoplastic resin (A) and the rubbery polymer having a reactive functional group (B) commonly exists at the interface between the continuous phase (A) and the dispersed phase (B). However, as the quantity of the compound resulting from the reaction between the thermoplastic resin (A) and the rubbery polymer having a reactive functional group (B) increases, the compound will start to be incorporated into the continuous phase (A) and/or the dispersed phase (B). The compound thus incorporated will form micells to maintain stable existence, and these micells will be seen as fine particles with a particle diameter of 1 to 100 nm when observed by electron microscopy. Accordingly, if the area occupied by the fine particles with a particle diameter 1 to 100 nm accounts for a large proportion, it suggests that a large amount of the compounds are produced by the reaction between the thermoplastic resin (A) and the rubbery polymer having a reactive functional group (B). It is necessary to allow the thermoplastic resin (A) and the rubbery polymer having a reactive functional group (B) to reaction to an extent that the area occupied by the fine particles accounts for 10% or more of the entire dispersed phase (B). If the area occupied by the fine particles is less than 10% of the dispersed phase (B), both the displacement when load becomes zero and the displacement range included in initial load ±2 kN will be small, and the shock absorption capability in the high speed compression will decrease. A thermoplastic resin composition having such morphology can be produced by, for example, forming a thermoplastic resin-rubbery polymer composite composition (A-B) by the method described later. The inorganic filler (C) may be either dispersed in the continuous phase of (A) or dispersed in the dispersed phase (B) in thermoplastic resin composition, or may be dispersed in both the continuous phase of (A) and the dispersed phase (B). In general, the fiber length of the inorganic filler (C) is larger than the particle diameter in the dispersed phase (B), and accordingly, it is preferable for the inorganic filler (C) to be dispersed in both the continuous phase of (A) and the dispersed phase (B) to ensure easy development of a high-load square wave in the high speed compression for square prism shaped molded specimens.

Generally known techniques may be used for the morphology observation. In general, the morphology in a thermoplastic resin composition will be maintained after melt molding. Therefore, morphological observation is carried out using a molded article prepared by injection molding of the thermoplastic resin composition. Specifically, the following observation method may be used. First, injection molding is carried out at a cylinder temperature that is 25° C. higher than the melting point of the thermoplastic resin (A) (or 100° C. higher than the glass transition temperature of the thermoplastic resin (A) when it is an amorphous resin such as polyphenylene oxide resin and polycarbonate resin) to prepare an ISO test piece, and a 1 to 2 mm square is cut out from its cross-sectional center portion. Then, the rubbery polymer having a reactive functional group (B) is dyed with ruthenium tetroxide. An ultrathin section of 0.1 μm or less (about 80 nm) is sliced off from the dyed material using an ultramicrotome at −196° C., and the continuous phase and the dispersed phase are observed by transmission electron microscopy first at a magnification of 5,000. In this observation, the thermoplastic resin (A) appears black or gray while the rubbery polymer having a reactive functional group (B) appears white. If the continuous phase and the dispersed phase cannot be seen definitely at a magnification of 5,000, the magnification is increased gradually up to 35,000 so that the continuous phase and the dispersed phase can be observed. Dispersed phase domains with a maximum diameter of 10 nm or more are observed in the phase. Then, the magnification is increased to 35,000, and observation is performed to determine if fine particles with a particle diameter of 1 to 100 nm exist in the dispersed phase (B). The particle diameter and the area occupied by fine particles the dispersed phase (B) are calculated by using an image analyzing program Scion Image supplied by Scion Corporation. For their particle diameter, 10 particles are selected randomly from the image obtained, and the number average particle diameter is determined. The diameter of a particle is determined by averaging the maximum and minimum sizes across the particle.

For the thermoplastic resin composition, a square prism specimen with a cross section of 12.7 mm×12.7 mm and a height of 25.4 mm prepared by the injection molding process in which the thermoplastic resin composition flows in the parallel direction to its height is characterized by giving a load-displacement curve that meets the requirements of (I), (II), and (III) described below when subjected to compression (high speed compression test) using a weight with a mass of 26 kg falling from a height of 0.5 m. If the weight is allowed to fall freely from a height of 0.5 m, the weight has a speed of 11 km per hour immediately before coming in contact with the square prism specimen, which simulates a collision of an automobile while braking (I) The displacement when load becomes zero is 6 mm or more, (II) the initial load is 12 kN or more and 30 kN or less, and (III) the displacement range included in initial load ±2 kN is 4 mm or more.

Figure 2:
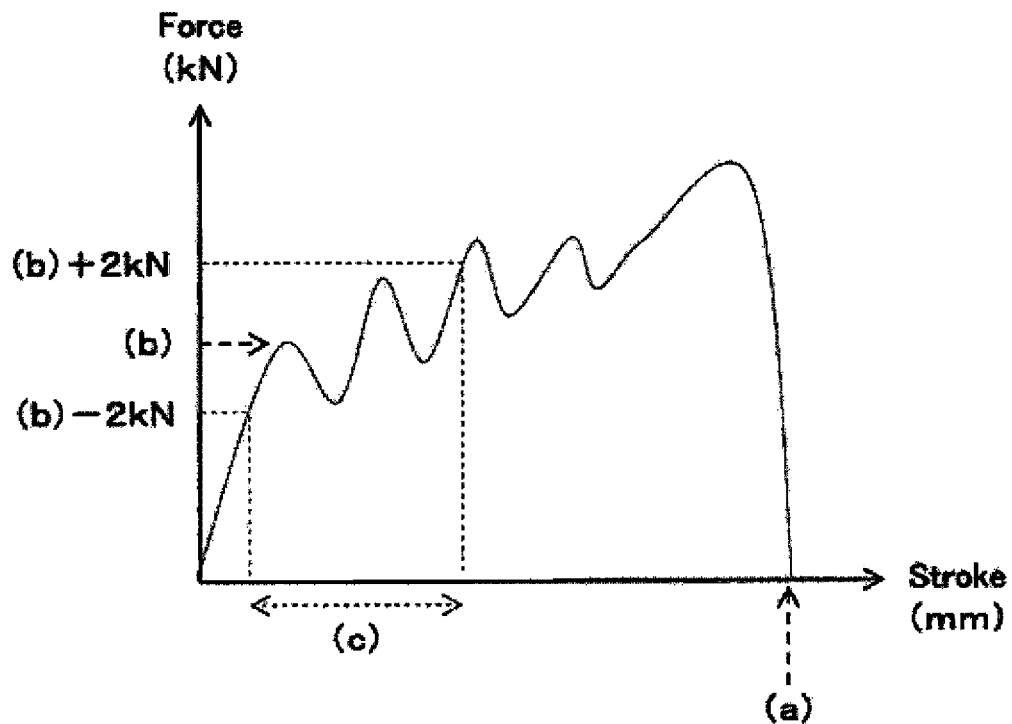
FIG. 2 is an illustrative diagram of a load-displacement curve obtained from the high speed compression test.

FIG. 1 shows an illustrative diagram of a square prism specimen to be used for the high speed compression test. In FIG. 1, the thermoplastic resin composition during injection molding flows in flow direction 1, which coincides with the height direction of the square prism specimen, and compression is applied in direction 2, which coincides with flow direction 1 of the thermoplastic resin composition during injection molding. FIG. 2 shows an illustrative diagram of a load-displacement curve obtained from the high speed compression test. In FIG. 2, the horizontal axis represents the displacement while the longitudinal axis represents the load. Point (a) shows the displacement when load becomes zero, that is, the displacement that occurs when the square prism specimen is destroyed. Point (b) shows the initial load, that is, the load at the first maximum that appears in load-displacement curve. Range (c) shows the displacement range included in initial load ±2 kN, that is, the range where the displacement changes continuously while showing a load within ±2 kN of the initial load.

(I) A displacement when load becomes zero, where the specimen is destroyed, of 6 mm or more suggests that the molded specimen is not destroyed easily when deformed under a high speed compression, demonstrating that the material is suitable for shock absorbing members. A larger displacement when load becomes zero, where the specimen is destroyed, indicates that the molded specimen is less breakable, demonstrating that the material is more suitable for shock absorbing members. (II) An initial load of 12 kN or more suggests that the molded specimen is not deformed easily even when compressed with a large energy that can take place in, for example, an automobile collision, demonstrating that the material is suitable for shock absorbing members liable to a large load. It is more preferably 16 kN or more. If the initial load is 30 kN or less, on the other hand, it suggests that in an automobile collision, for example, the other party (collided object) will not suffer from a large damage, demonstrating that the material is suitable for shock absorbing members. It is more preferably 25 kN or less. (III) A displacement range included in initial load ±2 kN of 4 mm or more suggests that the molded specimen can deform largely while maintaining the initial load, demonstrating that the material is suitable for shock absorbing members. A larger displacement range included in initial load ±2 kN is more preferred because the molded material can absorb shock stably.

It is desirable that in a load-displacement curve obtained from the high speed compression, a shock absorbing member is not easily breakable even when deformed under a large high speed compression, gives a high initial load, and can deform largely while maintaining the initial load (gives a high-load square wave). A load-displacement curve that meets the requirements from (I) to (III) can be obtained from, for example, a thermoplastic resin composition that contains specific quantities of a thermoplastic resin (A), rubbery polymer having a reactive functional group (B), and inorganic filler (C) and has a specific morphology as described above.

Conventional materials in a simple square prism shape cannot meet the aforementioned characteristics requirements, and therefore, they have been processed to have a complicated shape such as honeycomb structure, foam, hollow body, and ribbed structure, suitable for shock absorption. Even in a square prism shape, the thermoplastic resin composition can meet all of the requirements of (I), (II), and (III) and give a high-load square wave. Thus, the thermoplastic resin composition serves to provide small-sized, low-cost shock absorbing members.

If glass fiber is used as inorganic filler (C) for the thermoplastic resin composition, the glass fiber in the thermoplastic resin composition preferably has a weight-average fiber length of 300 to 400 μm and the glass fiber filaments with a length of 300 μm or less preferably account for 20 to 40 wt % of the total glass fiber quantity.

If the glass fiber in the thermoplastic resin composition has a weight-average fiber length of 300 μm or more, the strength of the glass fiber itself can be reflected easily in the molded material, and square prism shaped molded articles prepared by melt molding of the thermoplastic resin composition will show a larger initial load in the high speed compression. The displacement range included in initial load ±2 kN will also be larger. The glass fiber more preferably has a weight-average fiber length of 320 μm or more. If the glass fiber in the thermoplastic resin composition has a weight-average fiber length of 400 μm or less, on the other hand, the contact area between the glass fiber and the thermoplastic resin can be increased, and square prism shaped molded articles prepared by melt molding of the thermoplastic resin composition will show a larger displacement when load becomes zero in the high speed compression. The displacement range included in initial load ±2 kN will also be larger. The glass fiber more preferably has a weight-average fiber length of 380 μm or less.

If glass fiber with a fiber length of 300 μm or less accounts for 20 wt % or more of the total glass fiber quantity in the thermoplastic resin composition, the contact area between the glass fiber and thermoplastic resin can be increased, and square prism shaped molded articles prepared by melt molding of the thermoplastic resin composition will show a larger displacement when load becomes zero in the high speed compression. The displacement range included in initial load ±2 kN will also be larger. Glass fiber with a fiber length of 300 μm or less more preferably accounts for 23 wt % or more. If glass fiber with a fiber length of 300 μm or less accounts for 40 wt % or less of the total glass fiber quantity, square prism shaped molded articles prepared by melt molding of the thermoplastic resin composition will show a larger initial load in the high speed compression. The displacement range included in initial load ±2 kN will also be larger. Glass fiber with a fiber length of 300 μm or less more preferably accounts for 37 wt % or less.

The fiber length and distribution of glass fiber in a thermoplastic resin composition are measured by the methods described below. In general, the fiber length and distribution of glass fiber in a thermoplastic resin composition will be maintained after the composition is melt-molded. Therefore, observation of the fiber length and distribution of glass fiber is carried out for molded specimens prepared by injection molding of the thermoplastic resin composition. First, an ISO test piece is prepared by injection molding, and an about 5 g portion is taken from a central parallel region, and heated for ashing in a crucible at 550° C. for 2.5 hours. An 8 mg portion of the remaining glass fiber is sampled and dispersed in 40 cc of distilled water. Then, 0.3 ml of the dispersion liquid is put on a slide glass using a dropper, and observed and photographed at a magnification of 20 under an ECLIPSE 80i microscope manufactured by Nikon Corporation. For about 500 filaments of the photographed glass fiber, the weight-average fiber length of the glass fiber and the proportion of the glass fiber filaments with a fiber length of 300 μm or less are measured using a WinROOF image analysis program.

The calculation formula used to determine the weight-average fiber length is shown below. In the formula, $W_i$ represents the weight of glass fiber, $r_i$ represents the diameter of glass fiber filaments, $L_i$ represents the length of glass fiber filaments, $q_i$ represents the number of glass fiber filaments with a length of $L_i$, and $\rho$ represents the density of the glass fiber. The fiber length $L_i$ is assumed to be 4.8 μm or more.

$$\text{Weight-average fiber length} = \Sigma(W_i \times L_i)/\Sigma(W_i)$$

$$= \Sigma(\pi r_i^2 \times L_i \times \rho \times q_i \times L_i)/\Sigma(\pi r_i^2 \times L_i \times \rho \times q_i)$$

If the fiber diameter $r_i$ and the density $\rho$ are constant, the above formula can be simplified as shown below:

$$\text{Weight-average fiber length} = \Sigma(q_i \times L_i^2)/\Sigma(q_i \times L_i).$$

Assuming that the fiber diameter and density are constant, the proportion of glass fiber filaments with a fiber length of 300 μm or less can be calculated from the fiber length distribution. The fiber length is assumed to be 4.8 μm or more.

The thermoplastic resin composition preferably has a specific glass fiber length distribution in addition to a specific morphology formed by the thermoplastic resin (A) and the rubbery polymer having a reactive functional group (B) because molded articles, even in a simple shape such as square prism, will be so high in shock absorption capability as to be more highly indestructible and able to give a higher-load square wave under high speed compression.

The thermoplastic resin composition may further comprise a dendritic polyester resin (E) to improve the flowability during injection molding. Its blending quantity is preferably 0.1 to 30 parts by weight, more preferably 1 to 5 parts by weight, relative to the total weight of the thermoplastic resin (A) and the rubbery polymer having a reactive functional group (B), which accounts for 100 parts by weight. If the dendritic polyester resin (E) accounts for 0.1 or more parts by weight, the flowability during injection molding is improved. If the dendritic polyester resin (E) accounts for 30 or less parts by weight, on the other hand, the thermoplastic resin composition can be maintained good in other general physical properties. It is preferable for the dendritic polyester resin (E) to form a dispersed phase other than that of the rubbery polymer (B) in the thermoplastic resin composition.

The dendritic polyester resin (E) is a dendritic polyester resin that contains at least one structural unit selected from the group consisting of aromatic oxycarbonyl unit (S), aromatic and/or aliphatic dioxy unit (T), and aromatic dicarbonyl unit (U), along with a tri- or higher functional organic residue (D), with the component of (D) accounting for 7.5 to 50 mol % of the total quantity of the monomers that constitute the dendritic polyester.

The aromatic oxycarbonyl unit (S), aromatic and/or aliphatic dioxy unit (T), and aromatic dicarbonyl unit (U) are preferably structural units that are represented by Formula (1) below:

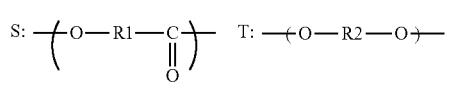

(1)

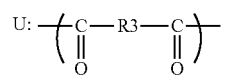

wherein R1 and R3 each are an aromatic residue. R2 is either an aromatic residue or aliphatic residue. In the dendritic polyester resin (E), R1, R2, and R3 may be either identical to or different from each other. The above aromatic residues may be, for example, a substituted or unsubstituted phenylene group, naphthylene group, or biphenylene group. Such aliphatic residues include, for example, ethylene, propylene, and butylene. R1, R2, and R3 each preferably have a structure as represented by the formulas below:

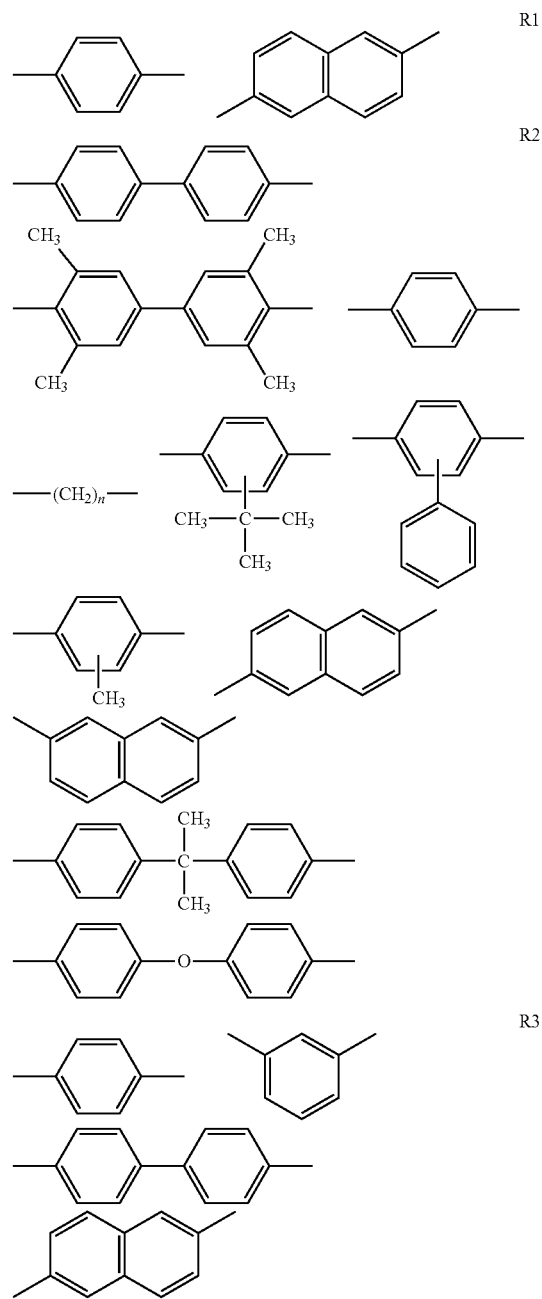

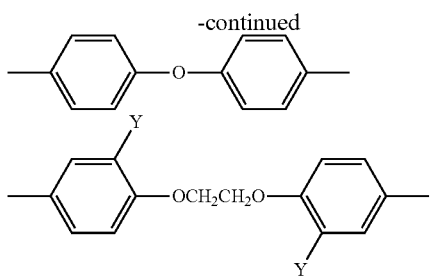

wherein Y's may be either identical to or different from each other and they are a hydrogen atom, halogen atom, or alkyl group. The alkyl groups preferably contain 1 to 4 carbon atoms. In the formulas, n is an integer of 2 to 8.

Specifically, R1 is a structure derived from an aromatic oxycarbonyl unit such as a structural unit produced from p-hydroxybenzoic acid or 6-hydroxy-2-naphthoic acid. Particularly preferable is a structural unit derived from p-hydroxybenzoic acid, and a structural unit derived from 6-hydroxy-2-naphthoic acid may be used in combination. In addition, structural units derived from an aliphatic hydroxycarboxylic acid such as glycolic acid, lactic acid, hydroxypropionic acid, hydroxybutyric acid, hydroxyvaleric acid, and hydroxycaproic acid may also be contained unless they impair the advantageous effects.

R2 is a structure derived from an aromatic and/or aliphatic dioxy unit, and examples include, for example, structural units produced from 4,4'-dihydroxy biphenyl, hydroquinone, 3,3',5,5'-tetramethyl-4,4'-dihydroxy biphenyl, t-butyl hydroquinone, phenyl hydroquinone, methyl hydroquinone, 2,6-dihydroxy naphthalene, 2,7-dihydroxy naphthalene, 2,2-bis (4-hydroxyphenyl)propane, 4,4'-dihydroxy diphenyl ether, ethylene glycol, 1,3-propylene glycol, or 1,4-butanediol. Preferable are structural units produced from 4,4'-dihydroxy biphenyl, hydroquinone, or ethylene glycol, and it is preferable that a structural unit produced from 4,4'-dihydroxy biphenyl and hydroquinone or from 4,4'-dihydroxy biphenyl and ethylene glycol be contained from the viewpoint of the control of liquid crystallinity.

R3 is a structural unit produced from an aromatic dicarbonyl unit, and its examples include those structural units produced from terephthalic acid, isophthalic acid, 2,6-naphthalene dicarboxylic acid, 4,4'-diphenyl dicarboxylic acid, 1,2-bis(phenoxy)ethane-4,4'-dicarboxylic acid, 1,2-bis(2-chlorophenoxy)ethane-4,4'-dicarboxylic acid, or 4,4'-diphenyl ether dicarboxylic acid. Preferable are structural units produced from terephthalic acid or isophthalic acid, and it is more preferably to use both of them in combination because it will be easy to adjust the melting point. In addition, structural units produced from sebacic acid or adipic acid may also be contained partially unless they impair the advantageous effect of this disclosure.

The dendritic polyester resin (E) comprises as basic skeleton a triply or higher multiply branching structure containing units of the tri- or higher functional organic residue (D) directly connected through ester bonding and/or amide bonding or connected via a structural unit selected from intermediate structural parts S, T, and U. The branched structure may comprise a single three- or four-branched skeleton or may comprise a plurality of three- or four-branched skeletons. It is not necessary for every polymer chain to have such a basic skeleton and, for example, a different structure may be at an end for terminal blocking. In the case where D is a trifunctional organic residue, structures in which all three functional groups in D are in a reacted form and structures in which only one or two functional groups are in a reacted form coexist in the dendritic polyester resin. It is preferable that the structures in which all three functional groups in D are in a reacted form preferably account for 15 mol % or more, more preferably 30 mol % or more, of the total quantity of D. In the case where D is a tetrafunctional organic residue, furthermore, structures in which all four functional groups in D are in a reacted form and structures in which only one, two, or three functional groups are in a reacted form coexist in the dendritic polyester resin. It is preferable that the structures in which all four functional groups in D are in a reacted form account for 10 mol % or more of the total quantity of D while the structures in which three functional groups are in a reacted form account for 20 mol % or more, and it is more preferable that the structures in which all four functional groups are in a reacted form account for 25 mol % or more of the total quantity of D while the structures in which three functional groups are in a reacted form account for 35 mol % or more of the total quantity of D.

D is preferably an organic residue of a trifunctional compound and/or a tetrafunctional compound, and it is most preferably an organic residue of a trifunctional compound.

Such a three-branched basic skeleton is schematically represented by Formula (2). Such a four-branched basic skeleton is schematically represented by Formula (3).

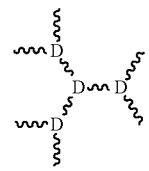

(2)

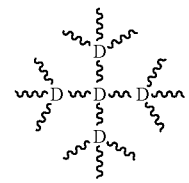

(3)

The dendritic polyester resin (E) is preferably a molten liquid crystalline resin. A molten liquid crystalline resin show a liquid crystalline state in a certain temperature range as it is heated from room temperature. A liquid crystal state is defined as one where the resin shows optical anisotropy when sheared.

To show a molten liquid crystallinity, a three-branched basic skeleton preferably contains organic residue (D) units connected to each other via an intermediate structural part R's that include a structural unit selected from a group consisting of S, T, and U, as shown in Formula (4) below:

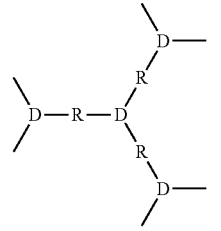

(4)

Similarly, in the case of a four-branched basic skeleton, a structure as shown by Formula (5) is preferable.

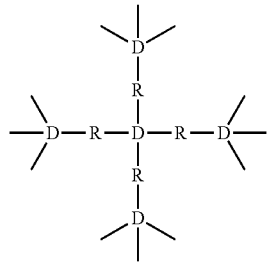

(5)

There are no specific limitations on the trifunctional organic residue represented by D, but it is preferably an organic residue of a compound containing at least one functional group selected from the group consisting of carboxyl group, hydroxyl group, and amino group. Their examples include residues of aliphatic compounds such as glycerol, methylol propane, tricarballylic acid, diaminopropanol, and diaminopropionic acid; and residues of aromatic compounds such as trimesic acid, trimellitic acid, 4-hydroxy-1,2-benzene dicarboxylic acid, phloroglucinol, α-resorcin acid, β-resorcin acid, γ-resorcin acid, tricarboxynaphthalene, dihydroxynaphthoic acid, aminophthalic acid, 5-aminoisophthalic acid, aminoterephthalic acid, diaminobenzoic acid, melamine, and cyanuric acid. Of these, residues of aromatic compounds are preferable, and residues represented by Formula (6) below are more preferable. Residues represented by Formula (6) include those of trimesic acid or α-resorcin acid are preferable, of which residues derived from trimesic acid are particularly preferable.

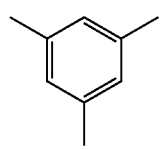

(6)

The tetra- or higher functional organic residue D is preferably an organic residue of a compound containing at least one functional group selected from the group consisting of carboxyl group, hydroxyl group, and amino group. Its examples include residues of aliphatic compounds such as erythritol, pentaerythritol, threitol, xylitol, glucitol, mannitol, 1,2,3,4-butane tetracarboxylic acid, 1,2,4,5-cyclohexane tetraol, 1,2,3,4,5-cyclohexanepentol, 1,2,3,4,5,6-cyclohexane hexyl, 1,2,4,5-cyclohexane tetracarboxylic acid, 1,2,3,4,5-cyclohexane pentacarboxylic acid, 1,2,3,4,5,6-cyclohexane hexacarboxylic acid, citric acid, and tartaric acid; and residues of aromatic compounds such as 1,2,4,5-benzene tetraol, 1,2,3,4-benzene tetraol, 1,2,3,5-benzene tetraol, 1,2,3,4,5-benzene pentol, 1,2,3,4,5,6-benzene hexyl, 2,2',3,3'-tetrahydroxy biphenyl, 2,2',4,4'-tetrahydroxy biphenyl, 3,3',4,4'-tetrahydroxy biphenyl, 3,3',5,5'-tetrahydroxy biphenyl, 2,3,6,7-naphthalene tetraol, 1,4,5,8-naphthalene tetraol, pyromellitic acid, mellophanic acid, prehnitic acid, mellic acid, 2,2',3,3'-biphenyl tetracarboxylic acid, 2,2',4,4'-biphenyl tetracarboxylic acid, 3,3',4,4'-biphenyl tetracarboxylic acid, 3,3',5,5'-biphenyl tetracarboxylic acid, 2,3,6,7-naphthalene tetracarboxylic acid, 1,4,5,8-naphthalene tetracarboxylic acid, 2,3,6,7-naphthalene tetraol, 1,4,5,8-naphthalene tetraol, 1,2,4,5,6,8-naphthalene hexyl, 1,2,4,5,6,8-naphthalene hexacarboxylic acid, and gallic acid. Residues as represented by Formula (7) below are more preferable:

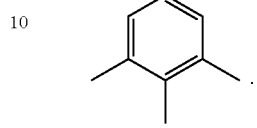

(7)

Specifically, preferable examples of the above tetrafunctional organic residues include residues of 1,2,4,5-benzene tetraol, 1,2,3,4-benzene tetraol, 1,2,3,5-benzene tetraol, pyromellitic acid, mellophanic acid, prehnitic acid, and gallic acid, of which residues of gallic acid are particularly preferable.

The aromatic hydroxycarbonyl unit (S), aromatic and/or aliphatic dioxy unit (T), and aromatic dicarbonyl unit (U) of a dendritic polyester resin (E) are units that form intermediate structural parts that connect the branches of the dendritic polyester resin (E). Assuming that the content d of D is 1 mole, it is preferable that p+q+r=1 to 10 where p, q, and r are the average contents (molar ratios) of the structural units S, T, and U, respectively. The total of p+q+r is more preferably in the range of 2 to 6. If the branch chain length is in this range, it will be possible to improve the effect of characteristics such as shear responsibility, that are attributed to the rigid, dense dendritic structures. For example, the values of p, q, and r can be determined by dissolving the dendritic polyester resin in a mixed solvent of 50 wt % pentafluorophenol and 50 wt % chloroform and subjected to proton nuclear magnetic resonance spectrum analysis at 40° C., and calculating the values from the ratios of peak strengths attributable to the structural units. The average contents are calculated from the integrated peak intensity ratios of the structural units and rounded to the nearest hundredth. The average chain length of the branch portions R is calculated from the integrated peak intensity ratios to the content d of branching structure D and it is assumed to represent the value of p+q+r. This value is also rounded to the nearest hundredth.

Both the ratio between p and q and the ratio between p and r (p/q and p/r) are preferably 5/95 to 95/5 and more preferably 20/80 to 80/20. If the ratios are in this range, liquid crystallinity will develop easily. If the ratios of p/q and p/r are 95/5 or less, the dendritic polyester resin will have a melting point in an appropriate range, while if p/q and p/r are 5/95 or more, the dendritic polyester resin will have molten liquid crystallinity.

It is preferable for the values of q and r to be substantially equal (equimolar), but either component may be added in excess with the aim of controlling the end group. The ratio of q/r is preferably in the range of 0.7 to 1.5 and more preferably 0.9 to 1.1. Being "equimolar" as referred to herein means being equal in molar quantity within a repeating unit, excluding the terminal structures. A terminal structure means the terminal of an intermediate structural part, and if the terminal is blocked, it means the end of the branch structure portion nearest to the terminal.

The intermediate structural part of the dendritic polyester resin preferably composed mainly of a polyester skeleton, but unless the characteristics are largely influenced, it is also possible to introduce a carbonate structure, amide structure, or urethane structure, of which the introduction of an amide structure is preferable. The introduction of such other bonds serves to adjust the compatibility with a wide variety of thermoplastic resins. A preferable method to introduce and amide structure is copolymerization with an aromatic amine compound such as p-aminobenzoic acid, m-aminobenzoic acid, p-aminophenol, m-aminophenol, p-phenylene diamine, m-phenylene diamine, m-xylylene diamine, and p-xylylene diamine; an aliphatic amine compound such as tetramethylene diamine, pentamethylene diamine, hexamethylene diamine, 2-methyl pentamethylene diamine, nonamethylene diamine, undecamethylene diamine, dodecamethylene diamine, 2,2,4-/2,4,4-trimethyl hexamethylene diamine, and 5-methyl nonamethylene diamine, or an alicyclic amine compound such as 1,3-bis(aminomethyl)cyclohexane, 1,4-bis (aminomethyl)cyclohexane, 1-amino-3-aminomethyl-3,5,5-trimethylcyclohexane, bis(4-aminocyclohexyl)methane, bis (3-methyl-4-aminocyclohexyl)methane, 2,2-bis(4-aminocyclohexyl)propane, bis(aminopropyl)piperazine, and aminoethyl piperazine. In particular, copolymerization with p-aminophenol or p-aminobenzoic acid is preferable.

Specific examples of intermediate structural part R containing a structural unit selected from the group consisting of S, T, and U include structures containing a structural unit produced from p-hydroxybenzoic acid and a structural unit produced from 6-hydroxy-2-naphthoic acid; structures containing a structural unit produced from p-hydroxybenzoic acid, a structural unit produced from 6-hydroxy-2-naphthoic acid; structures containing a structural unit produced from 4,4'-dihydroxy biphenyl, and a structural unit produced from terephthalic acid; structures containing a structural unit produced from p-hydroxybenzoic acid, a structural unit produced from 4,4'-dihydroxy biphenyl, a structural unit produced from terephthalic acid, and a structural unit produced from isophthalic acid; structures containing a structural unit produced from p-hydroxybenzoic acid, a structural unit produced from 4,4'-dihydroxy biphenyl, a structural unit produced from hydroquinone, a structural unit produced from terephthalic acid, and a structural unit produced from isophthalic acid; structures containing a structural unit produced from p-hydroxybenzoic acid, a structural unit produced from ethylene glycol, and a structural unit produced from terephthalic acid; structures containing a structural unit produced from p-hydroxybenzoic acid, a structural unit produced from ethylene glycol, a structural unit produced from 4,4'-dihydroxy biphenyl, and a structural unit produced from terephthalic acid; structures containing a structural unit produced from p-hydroxybenzoic acid, a structural unit produced from hydroquinone, a structural unit produced from 4,4'-dihydroxy biphenyl, a structural unit produced from terephthalic acid, and a structural unit produced from 2,6-naphthalene dicarboxylic acid; and structures containing a structural unit produced from p-hydroxybenzoic acid, a structural unit produced from 6-hydroxy-2-naphthoic acid, a structural unit produced from hydroquinone, and a structural unit produced from terephthalic acid.

In particular, an R containing structural units (I), (II), (III), (IV), and (V) below or an R containing structural units structural units (I), (II), (VI), and (IV) below is preferable.

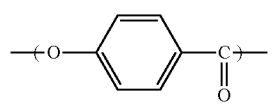

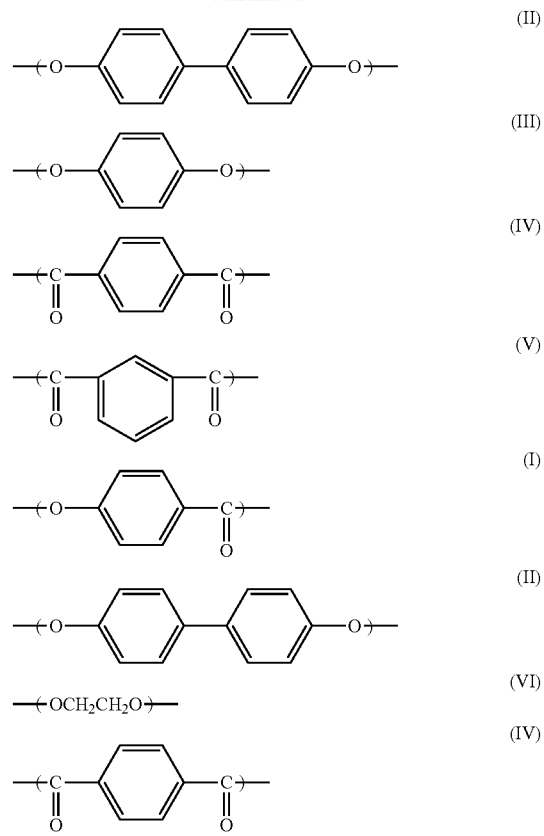

In the case of an R containing structural units (I), (II), (III), (IV), and (V) above, the content p of structural unit (I) preferably accounts for 30 to 70%, more preferably 45 to 60%, of the total content of the structural units, i.e., p+q+r. The content q(II) of structural unit (II) preferably accounts for 60 to 75%, more preferably 65 to 73%, of the total content q of structural units (II) and (III). Furthermore, the content r(IV) of structural unit (IV) preferably accounts for 60 to 92%, more preferably 62 to 68%, of the total content r of structural units (IV) and (V). These cases are preferable because shear responsiveness and flowability improving effect of their addition to the thermoplastic resin are developed significantly.

In the case of an R containing structural units (I), (II), (VI), and (IV) above, the content p of structural unit (I) above preferably accounts for 30 to 90%, more preferably 40 to 80%, of the total content of structural units (I), (II), (VI), and (IV). The content q(VI) of structural unit (VI) preferably accounts for 70 to 5%, more preferably 60 to 8%, of the total content q of structural units (II) and (VI).

Furthermore, the terminal of the dendritic polyester resin is preferably carboxyl group, hydroxyl group, amino group, or residue of a derivative containing these groups. Derivatives of the hydroxyl group and derivatives having the carboxyl group include, for example, alkyl esters such as methyl ester, and aromatic esters such as phenyl ester and benzyl ester.

The terminals may be blocked using a monofunctional epoxy compound, oxazoline compound, orthoester, acid anhydride compound and the like. Useful terminal blocking methods include a method in which a monofunctional organic compound is add in advance before synthesizing a dendritic polyester resin and a method in which a monofunctional organic compound is added at a stage where the skeleton of the dendritic polyester resin have progressed to some degree.

Specifically, when the hydroxyl group terminal and acetoxy terminal are to be blocked, it is preferable to add benzoic acid, 4-t-butyl benzoic acid, 3-t-butyl benzoic acid, 4-chlorobenzoic acid, 3-chlorobenzoic acid, 4-methyl benzoic acid, 3-methyl benzoic acid, 3,5-dimethyl benzoic acid and the like.

The carboxyl group terminal can be blocked by reacting it with a monofunctional compound reactive with carboxylic acid. A monofunctional compound reactive with carboxylic acid is a compound that has, in its molecule, one functional group that reacts with carboxylic acid at room temperature or elevated temperature to form an ester, amide, urethane, or urea bond. If a monofunctional compound reactive with carboxylic acid is reacted with a carboxylic acid group existing at the molecular terminal of a dendritic polyester resin to introduce a monofunctional compound at the molecular terminal, the retention stability and hydrolysis resistant of the dendritic polyester resin will be improved and, during kneading of other thermoplastic resins and fillers, the decomposition of the thermoplastic resins and fillers will be depressed. Furthermore, the improvement in the dispersibility of the dendritic polyester is expected to work to improve the flowability and other physical properties.

Monofunctional compounds reactive with carboxylic acid that can be used for the dendritic polyester resin include, for example, oxazoline compounds, epoxy compounds, orthoester compounds, isocyanate compounds, carbodiimide compounds, and diazo compounds. From the viewpoint of the reactivity with carboxylic acid and handleability, oxazoline compounds, epoxy compounds, orthoester compounds, and isocyanate compounds can be used favorably. A plurality thereof may be used in combination.

Preferable oxazoline compounds include 2-methyl-2-oxazoline, 2-ethyl-2-oxazoline, 2-propyl-2-oxazoline, 2-butyl-2-oxazoline, 2-isopropyl-2-oxazoline, 2-isobutyl-2-oxazoline, 2-sec-butyl-2-oxazoline, 2-tert-butyl-2-oxazoline, 2-phenyl-2-oxazoline, and 2-biphenyl-2-oxazoline. Preferable epoxy compounds include ethylene oxide, propylene oxide, butyl glycidyl ether, phenyl glycidyl ether, and benzoic acid glycidyl ester. Preferable orthoester compounds include trimethyl orthoacetate, triethyl orthoacetate, trimethyl orthoformate, and triethyl orthoformate. Preferable isocyanate compounds include methyl isocyanate, ethyl isocyanate, propyl isocyanate, butyl isocyanate, and phenyl isocyanate.

Theoretically, terminal blocking can be carried out by adding an organic compound used for terminal blocking in an amount that corresponds to that of the end group at the terminal to be blocked. It is preferable to add the organic compound used for terminal blocking in an amount of 1.005 or more equivalents, more preferably 1.008 or more equivalents, relative to the amount of the end group at the terminal to be blocked. The effect of terminal blocking is achieved adequately if the organic compound used for terminal blocking is added in an amount of 1.005 or more equivalents. It is preferable for the organic compound used for terminal blocking to be added in an amount of 2.5 or less equivalents. If the amount of the organic compound used for terminal blocking is 2.5 or less equivalents, the gas generation attributable to the remaining excess organic compound can be depressed. The effect for terminal blocking will be achieved adequately.

The content of organic residue D represents the proportion of the polyfunctional compound that produces organic residues relative to the total quantity of monomers that constitute the dendritic polyester, and the content is preferably 7.5 mol % or more, more preferably, 10 mol % or more, and still more preferably 13 mol % or more. In such a case, the intermediate structural part will have a sequence length that is suitable for the dendritic polyester to be in a dendritic form. With respect to the upper limit, the content of organic residue D is preferably 50 mol % or less, and more preferably 45 mol % or less, and still more preferably 40 mol % or less. Furthermore, the dendritic polyester resin may be partially crosslinked unless it has significant influence on characteristics.

There are no specific limitations on the method to be used to produce a dendritic polyester resin, and its production can be carried out by a generally known condensation method for polymerization of polyester. In a preferable method, the monomers used to constitute the structural units represented by R1, R2, and R3 are acylated, and when a trifunctional monomer is reacted, the feed quantity (moles) of the trifunctional monomer is adjusted to 7.5 mol % or more of the total monomer quantity (moles). In the case of a dendritic polyester resin produced from an R composed of structural units (I), (II), (III), (IV), and (V), and trimesic acid, preferable methods include (1) acetic anhydride is reacted with p-hydroxybenzoic acid, 4,4'-dihydroxy biphenyl, hydroquinone, terephthalic acid, and isophthalic acid to acylate the phenolic hydroxyl groups, and then acetic acid elimination type condensation polymerization is carried out to synthesize liquid crystalline polyester oligomers, followed by addition of trimesic acid and further acetic acid elimination type condensation polymerization, and (2) acetic anhydride is reacted with p-hydroxybenzoic acid, 4,4'-dihydroxy biphenyl, hydroquinone, terephthalic acid, isophthalic acid, and trimesic acid to acylate the phenolic hydroxyl groups, followed by carrying out acetic acid elimination type condensation polymerization. To produce a dendritic polyester resin by acetic acid elimination type condensation polymerization, it is preferable to use a melt polymerization process in which reaction is carried out at a temperature where the dendritic polyester resin melts, under reduced pressure as required, and a predetermined quantity of acetic acid is distilled out to complete the condensation polymerization reaction. More specifically, production can be carried out by, for example, the dendritic polyester resin production method described in Japanese Unexamined Patent Publication (Kokai) No. 2011-195814.

It is preferred that the number average molecular weight of dendritic polyester resin (E) is 1,000 to 40,000, more preferably 1,000 to 20,000. The number average molecular weight is measured by GPC-LS (gel penetration chromatography-light scattering) using a solvent that can dissolve the dendritic polyester resin (E).

In addition, it is preferable for the dendritic polyester resin (E) to have a melt viscosity of 0.01 to 50 Pa·s, more preferably 1 to 20 Pa·s. The melt viscosity at a temperature 10° C. higher than the liquid crystallization starting temperature and a shear rate of 100/s using a constant-load, orifice-type flow tester.

If the thermoplastic resin (A) is a polyamide resin, it is preferable to further add an acid anhydride (F). The addition of an acid anhydride serves to block the amino-terminals of the polyamide resin to improve the flowability during injection molding. Useful acid anhydrides include, for example, benzoic anhydride, isobutyric anhydride, itaconic anhydride, octanoic anhydride, glutaric anhydride, succinic anhydride, acetic anhydride, dimethyl maleic anhydride, decanoic anhydride, trimellitic anhydride, 1,8-naphthalic anhydride, phthalic anhydride, maleic anhydride, and derivatives thereof. A plurality thereof may be used in combination. Of these, succinic anhydride and phthalic anhydride are used favorably, and succinic anhydride is particularly preferable. Its blending quantity is preferably 0.01 to 3 parts by weight, more preferably 0.1 to 2 parts by weight, relative to the total weight of the thermoplastic resin (A) and the rubbery polymer having a reactive functional group (B), which accounts for 100 parts by weight. If the acid anhydride (F) accounts for 0.01 or more parts by weight, the flowability during injection molding can be further improved. If the acid anhydride accounts for 3 or less parts by weight, on the other hand, the thermoplastic resin composition can be maintained good in other general physical properties.

The thermoplastic resin composition may contain components other than (A), (B), (C), (E), and (F) unless its characteristics are impaired.

For example, the thermoplastic resin composition may contain a rubber component other than (B) as required unless its characteristics are impaired. Such a rubber component may be a rubbery polymer that is given above as an example of the rubbery polymer having a reactive functional group (B) and that is free of reactive functional groups. A plurality thereof may be combined. If such a rubber is used, there are no specific limitations on the blending quantity, it is preferably 0.1 to 400 parts by weight relative to the total weight of the thermoplastic resin (A) and the rubbery polymer having a reactive functional group (B), which accounts for 100 parts by weight.

In addition, the thermoplastic resin composition may contain various additives as required unless its characteristics are impaired. Such various additives include, for example, crystal nucleating agent, color protecting agent, antioxidant (thermal stabilizer), weathering agent, mold releasing agent, plasticizer, lubricant agent, dye type coloring agent, pigment type coloring agent, antistatic agent, flame retarder, and blowing agent. A plurality thereof may be combined. There are no specific limitations on their blending quantity, it is preferably 0.01 to 20 parts by weight relative to the total weight of the thermoplastic resin (A) and the rubbery polymer having a reactive functional group (B), which accounts for 100 parts by weight.

Favorable antioxidants (thermal stabilizers) include hindered phenolic compounds, hindered amine based compounds, hydroquinone based compounds, phosphorous compounds, and substitution products thereof, as well as copper halides and iodized compounds.

Favorable weathering agents include resorcinol based compounds, salicylate based compounds, benzotriazole based compounds, benzophenone based compounds, and hindered amine based compounds.

Favorable mold releasing agents include aliphatic alcohol, aliphatic amide, aliphatic bisamide, ethylene bis-stearyl amide, and higher fatty acid esters.

Favorable plasticizers include octyl p-oxybenzoate, and N-butyl benzene sulfone amide.

Favorable dye type coloring agents include nigrosine, and aniline black.

Favorable pigment type coloring agents include cadmium sulfide, phthalocyanine, and carbon black.

Favorable antistatic agents include alkyl sulfate type anionic antistatic agents, quaternary ammonium salt type cationic antistatic agents, nonionic antistatic agents such as polyoxy ethylene sorbitan monostearate, and betaine based amphoteric antistatic agents.

Favorable flame retarders include melamine cyanurate, hydroxides such as magnesium hydroxide, aluminum hydroxide, ammonium polyphosphate, brominated polystyrene, brominated polyphenylene oxide, brominated polycarbonate, brominated epoxy resin, and combinations of antimony trioxide and these bromine based flame retarders.

Favorable antioxidants and thermal stabilizers include hindered phenolic compounds and phosphorous compounds in particular.

Specific examples of the hindered phenolic compounds include triethylene glycol-bis[3-t-butyl-(5-methyl-4-hydroxyphenyl) propionate], N,N'-hexamethylene bis(3,5-di-t-butyl-4-hydroxy-hydrocinnamide), tetrakis[methylene-3-(3',5'-di-t-butyl-4'-hydroxyphenyl) propionate]methane, pentaerythrityl tetrakis[3-(3',5'-di-t-butyl-4'-hydroxyphenyl) propionate], 1,3,5-tris(3,5-di-t-butyl-4-hydroxybenzyl)-s-triazine-2,4,6-(1H,3H,5H)-trione, 1,1,3-tris-(2-methyl-4-hydroxy-5-t-butyl phenyl)butane, 4,4'-butylidene bis(3-methyl-6-t-butyl phenol), n-octadecyl-3-(3,5-di-t-butyl-4-hydroxyphenyl) propionate, 3,9-bis[2-(3-(3-t-butyl-4-hydroxy-5-methyl phenyl) propionyloxy)-1,1-dimethylethyl]-2,4,8,10-tetraoxaspiro[5,5]undecane, and 1,3,5-trimethyl-2,4,6-tris-(3,5-di-t-butyl-4-hydroxybenzyl)benzene.

In particular, ester based polymer hindered phenol type ones are preferable, and specific examples include tetrakis[methylene-3-(3',5'-di-t-butyl-4'-hydroxyphenyl) propionate]methane, pentaerythrityl tetrakis[3-(3',5'-di-t-butyl-4'-hydroxyphenyl) propionate], and 3,9-bis[2-(3-(3-t-butyl-4-hydroxy-5-methyl phenyl) propionyloxy)-1,1-dimethylethyl]-2,4,8,10-tetraoxaspiro[5,5]undecane.

Specific examples of the phosphorous compounds include phosphite based compounds such as bis(2,6-di-t-butyl-4-methyl phenyl)pentaerythritol-di-phosphite, bis(2,4-di-t-butyl phenyl)pentaerythritol-di-phosphite, bis(2,4-di-cumyl phenyl)pentaerythritol-diphosphite, tris-(2,4-di-t-butyl phenyl) phosphite, tetrakis(2,4-di-t-butyl phenyl)-4,4'-bisphenylene phosphite, di-stearyl pentaerythritol-di-phosphite, and triphenyl phosphite; and 3,5-di-butyl-4-hydroxybenzyl phosphonate diethyl ester.

With respect to the production methods for the thermoplastic resin composition, it can be produced either in a molten state or in a solution state, of which production in a molten state is preferred from the viewpoint of reactivity improvement. For the production in a molten state, the available techniques include the use of an extruder for melt kneading and the use of a kneader for melt kneading, of which melt kneading with an extruder that can perform continuous production is preferred from the viewpoint of productivity. The useful extruders for melt kneading include single screw extruder, multi-axis extruders such as twin screw extruder, four screw extruder, and biaxial-uniaxial composite extruder, and one or more extruders can be used. From the viewpoint of kneading performance, reactivity, and productivity improvement, the use of multi-axis extruders such as twin screw extruder and four screw extruder is preferable, and the use of a twin screw extruder for melt kneading is the most preferable.

A preferable production process for the thermoplastic resin composition is to mix a thermoplastic resin (A) and a rubbery polymer having a reactive functional group (B) to produce a thermoplastic resin-rubbery polymer composite composition (A-B) having morphological features such that the thermoplastic resin (A) and the rubbery polymer having a reactive functional group (B) form a continuous phase and a dispersed phase, respectively, and the dispersed phase (B) formed by the rubbery polymer having a reactive functional group contains fine particles with a diameter of 1 to 100 nm of a compound resulting from a reaction between the thermoplastic resin (A) and the rubbery polymer having a reactive functional group (B), with the area occupied by the fine particles accounting for 10% or more of the dispersed phase (B), followed by adding an inorganic filler (C) and, if necessary, a dendritic polyester resin (E), an acid anhydride (F), and other various additives. The dendritic polyester resin (E), acid anhydride (F), and other various additives as described above may be fed together with the thermoplastic resin (A) and the rubbery polymer having a reactive functional group (B) to such an extent that the formation of the thermoplastic resin-rubbery polymer composite composition (A-B) is not impaired.

The thermoplastic resin-rubbery polymer composite composition (A-B) preferably meets the relation E(V1)>E(V2) where E(V1) and E(V2) represent the tensile modulus at tension speeds V1 and V2, respectively, and where V1<V2. Furthermore, the thermoplastic resin-rubbery polymer composite composition (A-B) preferably meets the relation $\epsilon$(V1) <$\epsilon$(V2) where $\epsilon$(V1) and $\epsilon$(V2) represent the tensile elongation at break at tension speeds V1 and V2, respectively, and where V1<V2. The tensile test for this case is conducted in accordance with a method specified in applicable standards, for example, by using JIS-5A dumbbell type test pieces prepared by injection molding. The tensile modulus is defined as the gradient of the initial straight line portion of a stress-strain curve. The tensile elongation at break is defined as the elongation at the moment of breakage. The above relational expressions are preferably met at any V1 and V2 values in the tension speed range of 10 mm/min or more and 500 mm/min or less, more preferably at any V1 and V2 values in the tension speed range of 1 mm/min or more and 1,000 mm/min or less.

The methods from (1) to (3) below are effective for the production of a thermoplastic resin-rubbery polymer composite composition (A-B) having morphology and tensile characteristics as described above. The method of (3) is more preferable from the viewpoint of productivity.

(1) For example, the method described in Japanese Unexamined Patent Publication (Kokai) No. 2008-156604 may be offered. Specifically, a thermoplastic resin (A) and a rubbery polymer having a reactive functional group (B) are fed to a twin screw extruder having a plurality of full flight zones and kneading zones and having a screw length of L and a screw diameter D with a ratio L/D of 50 or more, and production is carried out by melt kneading under the conditions where the following relation is met:

$Pk\text{max} \geq Pf\text{min} + 0.3$ where Pkmax (MPa) is the resin pressure in the kneading zone that has the highest resin pressure in the screw and Pfmin (MPa) is the resin pressure in the full flight zone that has the lowest resin pressure in the screw. The ratio L/D is calculated by dividing the screw length L by the screw diameter D. The screw length is the distance from the upstream-side end of the screw segment located at the root of the screw where the material is fed (feed port), to the tip of the screw. In an extruder, the direction toward the position where material is supplied and that toward the position where molten resin is discharged are sometimes referred to as upstream and downstream, respectively. In this method, the reaction can be accelerated effectively by increasing the resin pressure in kneading zones above the resin pressure in full flight zones in a certain range.

(2) For example, the method described in WO 2009/119624 can be cited. Specifically, production is carried out by melt-kneading a thermoplastic resin (A) and a rubbery polymer having a reactive functional group (B) under elongational flow. An elongational flow consists of two flows moving in opposite directions in which molten resin is stretched. On the other hand, a shear flow, which has been commonly used, consists of two flows moving at different speeds in same directions in which molten resin is deformed. Compared to a shear flow, which has been generally used for melt kneading, elongational flow kneading of a thermoplastic resin-rubbery polymer having reactive functional group composite composition (A-B) can achieve high dispersion efficiency. In the case of production for alloy with reaction such as reactive processing, it facilitates efficient progress of the reaction.

(3) For example, the method described in Japanese Unexamined Patent Publication (Kokai) No. 2011-063015 may be cited. Specifically, production is carried out by melt-kneading a thermoplastic resin (A) and a rubbery polymer having a reactive functional group (B) under elongational flow, then melt-kneading in mixing screw having notch section.

For the aforementioned method of (3), the inflow-effect pressure fall between the inlet and outlet of the zone where the resin is melt-kneaded under elongational flow (elongational flow zone) is preferably 10 to 1,000 kg/cm$^2$ (0.98 to 98 MPa). The inflow-effect pressure fall between the inlet and outlet of an elongational flow zone is calculated by subtracting the pressure difference ($\Delta P_0$) in the elongational flow zone from the pressure difference ($\Delta P$) immediately before the elongational zone. If the inflow-effect pressure fall between the inlet and outlet of the elongational flow zone is 10 kg/cm$^2$ (0.98 MPa) or more, an elongational flow is more likely to be formed in the elongational flow zone, and the pressure distribution can be made more uniform. If the inflow-effect pressure fall between the inlet and outlet of the elongational flow zone is 1,000 kg/cm$^2$ (98 MPa) or less, the back pressure in the extruder is maintained in a moderate range, facilitating stable production. The inflow-effect pressure fall between the inlet and outlet of the elongational flow zone is more preferably 100 to 500 kg/cm$^2$ (9.8 to 49 MPa).

For the aforementioned method of (3) where Lk is the length of an elongational flow zone of a screw in an extruder and D is the screw diameter, the ratio Lk/D is preferably 2 to 10 from the viewpoint of kneading performance and reactivity. It is more preferably more preferably 3 to 8.

Preferable methods for forming an elongational flow zone include, for example, the use of twist kneading disks arranged so that the helix angle θ, i.e., the angle between an apex of the front end side of the disk and an apex of the rear surface side of the disk, is 0°<θ<90° in the caracole direction of the screws, the use of a flighted screw designed so that the flight portion contains a resin passage having a cross section that decreases in the direction from the front vertex toward the rear vertex of the screw, and the use of an extruder containing a resin passage in which the cross section for passing the molten resin is decreasing gradually.

Figure 3:
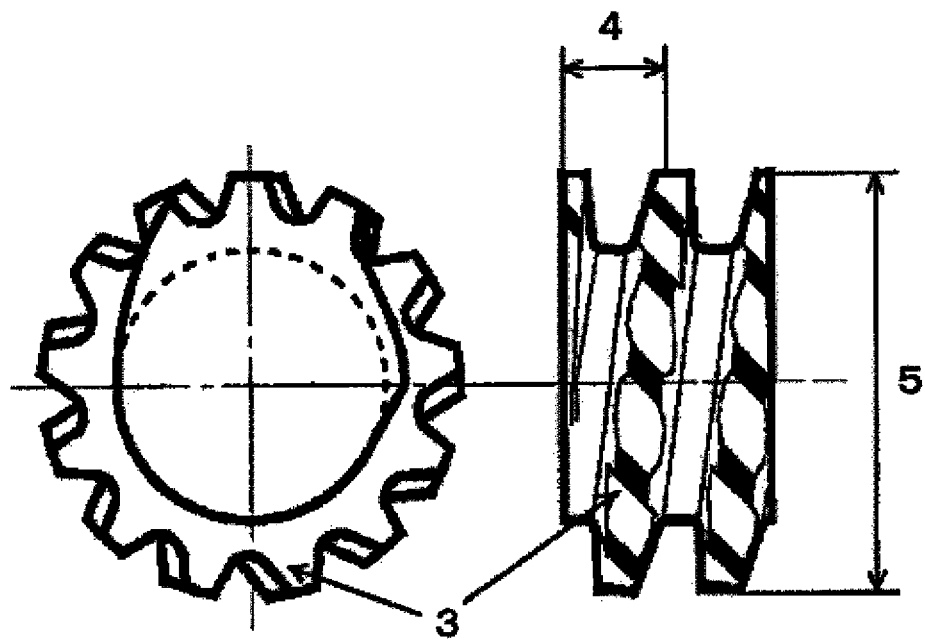
FIG. 3 is a schematic diagram of a mixing screw having notch section.

For the aforementioned method of (3), the notches in the mixing screw having notch section are produced by scraping ridge portions of the screw. FIG. 3 shows a schematic diagram of a mixing screw having notch section. The left and right diagrams give a cross-sectional view and a side view, respectively, and show notches (3), screw pitch (4), and screw diameter D (5). The screw pitch 4 represents the distance over which the screw moves as it rotates by 360°. The use of mixing screws having notch section serves to increase the resin filling rate, and the molten resin passing through a mixing zone containing interlinked mixing screws having notch section is susceptible to the cylinder temperature of the extruder. Accordingly, even if the molten resin is heated as a result of the acceleration of reaction in the elongational flow zone located in the upstream region of the extruder, it can be cooled efficiently in the mixing zone down to a low resin temperature. Since the reaction is accelerated in the elongational flow zone located in the front part, the resin is high in melt viscosity during its passage through the mixing zone, and the notches of the mixing screw having notch section work effectively to shear the resin, thereby accelerating the reaction. Thus, the technique that performs melt kneading under elongational flow and subsequent melt kneading by mixing screws having notch section serves to improve the kneading performance and reactivity while depress the temperature rise in the resin. Accordingly, even if a large-type extruder with a small L/D ratio between the screw length L and screw diameter D is used for processing in large quantities, thermal degradation of the resin is depressed to make it possible to provide a thermoplastic resin-rubbery polymer composite composition (A-B) with high shock absorbing capability.

For the aforementioned method of (3), the zone where melt kneading is performed by mixing screws having notch section (mixing zone) preferably includes interlinked mixing screws having notch section each in the form of a single thread screw with a screw pitch of 0.1 D to 0.5 D and 8 to 16 notches per pitch, from the viewpoint of improving cooling efficiency due to efficient filling with the molten resin as well as improved kneading performance and improved reactivity. It is more preferable to use interlinked mixing screws having notch section with a screw pitch of 0.1 D to 0.3 D and 10 to 15 notches per pitch. A single thread screw has one screw flight ridge per 360° rotation of the screw.

For the aforementioned method of (3) where Lm is the length of a mixing zone of a screw in an extruder and D is the screw diameter, the ratio Lm/D is preferably 4 to 20 from the viewpoint of improving cooling efficiency due to efficient filling with the molten resin as well as improved kneading performance and improved reactivity. It is more preferably 5 to 15.

For the aforementioned method of (3), it is preferable to provide two or more mixing zones from the viewpoint of improving cooling efficiency due to efficient filling with the molten resin as well as improved kneading performance and improved reactivity.

For the aforementioned method of (3), it is preferable that 70% or more of the mixing screws having notch section included in the mixing zones have a thread direction opposite to the screw axis rotation direction from the viewpoint of improving cooling efficiency due to efficient filling with the molten resin as well as improved kneading performance and improved reactivity. It is more preferably 75% or more.

For the aforementioned method of (3), it is preferable that melt kneading is performed under conditions where the relation $Ck-Cm \geq 40$ is met where Ck and Cm represent the extruder cylinder temperature in the elongational flow zones and the extruder cylinder temperature in the mixing zones, respectively, from the viewpoint of significant improving cooling efficiency of the molten resin as well as significantly improved kneading performance and significantly improved reactivity. It is preferable to perform melt kneading under conditions where the relation $Ck-Cm \geq 60$ is met. In general, a chemical reaction progresses more rapidly at a higher reaction temperature, and the rate of a reaction between a thermoplastic resin and a reactive functional group tends to decrease with a decreasing resin temperature. On the contrary, in the aforementioned method of (3), the reaction can be progressed by lowering the cylinder temperature in the mixing zones. This is considered to be because zones for melt kneading under elongational flow are provided in the upstream region to promote the reaction between the thermoplastic resin and the reactive functional group, and the resin has a high melt viscosity when pass the mixing zones. Accordingly, if the resin temperature is decreased to further increase the melt viscosity, it is expected that the notches of the mixing screws having notch section will have stronger shearing effect, thereby accelerating the reaction to a degree that overcomes the decrease in the reaction rate caused by the decrease in the resin temperature. This effect is enhanced significantly when the screw arrangement is such that the elongational flow zones precede the mixing zones containing mixing screws having notch section. Compared to this, in the case where, for example, common kneading disks that are unable to form an elongational flow are used for melt kneading in the upstream region, the rate of reaction between the thermoplastic resin and reactive functional groups will be small and, even if mixing zones containing mixing screws having notch section are provided following the kneading disk zones, the melt viscosity of the resin passing through the mixing zones will be low. Accordingly, the notches of the mixing screws having notch section will not have a significant shearing effect, and the rate of reaction will be small compared to the case where zones designed for melt kneading under elongational flow are provided in the upstream region.

For the aforementioned method of (3), useful extruders include, for example, single screw extruders, twin screw extruders, and multiple screw extruders equipped with three or more screws. In particular, single screw extruders and twin screw extruders are used favorably, of which twin screw extruders are more preferred. There are no specific limitations on the type of screws for the twin screw extruder to be used, and useful ones include screws of a complete intermeshing type, incomplete intermeshing type, and non-intermeshing type, of which screws of a complete intermeshing type are preferred from the viewpoint of kneading performance and reactivity. With respect to the rotation direction, the screws may rotate either in the same direction or in different directions, but they preferably rotate in the same direction from the viewpoint of kneading performance and reactivity. It is most preferable to use complete intermeshing type co-rotating screws.

The aforementioned method of (3) is applied favorably to melt kneading using general purpose twin screw extruders with a L/D ratio of less than 50. If twin screw extruders with a large screw diameter D with the aim of increasing the processing rate, it is still possible to produce a thermoplastic resin composition with a high heat resistance, impact resistance, shock absorbing capability and the like, while depressing thermal resin degradation.

For the aforementioned method of (3), the total length of the zones designed for melt kneading under elongational flow are provided in the upstream region (elongational flow zones) preferably account for 5 to 40% of the overall screw length of the extruder, and the total length of the zones containing mixing screws having notch section for melt kneading (mixing zones) preferably account for 15 to 40% of the overall screw length of the extruder, from the viewpoint of improving cooling efficiency due to efficient filling with the molten resin as well as improved kneading performance and improved reactivity. It is more preferable that the total length of the elongational flow zones account for 8 to 35%, and at the same time, the total length of the mixing zones account for 17 to 35%.

For the aforementioned method of (3), the residence time in the extruder is preferably 6 to 1,200 seconds. The residence time is defined as the time period when the material stays in the extruder after its supply until its exit from the discharge port. To determine the residence time, a coloring agent is fed together with the material through the root portion of the screw where the material is supplied, followed by measuring the time period from the feeding of the coloring agent until the degree of coloring of the extruded material with the coloring agent reaches a maximum as it is extruded out of the discharge port of the extruder. If the residence time is 6 seconds or more, the reaction in the extruder progresses adequately to achieve good characteristics (good balance between heat resistance and impact resistance) and the shock absorbing capability with the peculiar viscoelasticity characteristics of the thermoplastic resin-rubbery polymer composite composition (A-B). If the residence time is 1,200 seconds or less, thermal degradation of the resin, which would result from a long residence time, can be depressed. The residence time is preferably 30 to 300 seconds.

It is preferable that the inorganic filler (C), dendritic polyester resin (E), acid anhydride (F), and other additive be supplied from the root of the extruder after the formation of a thermoplastic resin-rubbery polymer composite composition (A-B) as described above or that they be supplied from a midstream portion of the extruder by a method such as side feeding.

For the production of the thermoplastic resin composition, it is preferable that the inorganic filler (C) be fed to the twin screw extrude after a thermoplastic resin-rubbery polymer composite composition (A-B) has been formed by a twin screw extruder by the aforementioned method. The thermoplastic resin-rubbery polymer composite composition (A-B) may be prepared in advance by a extruder other than the twin screw extruder in which an inorganic filler is added, or may be produced before the addition of an inorganic filler in the twin screw extruder in which the inorganic filler is to be added.

In particular, if glass fiber is used as inorganic filler and fed by the latter method where the material resin is supplied from an upstream port and the molten resin is discharge from an downstream port with the upstream end of the screw and the downstream end of the screw being defined as being located at the 0% position and the 100% position, respectively, it is preferable for the glass fiber to be fed at a 50% or more and 80% or less position. The thermoplastic resin (A) and the rubbery polymer having a reactive functional group (B) are fed at a 0 to 5% position. The percentage in this case shows a length-basis proportion.

The feeding of glass fiber at the aforementioned position allows the glass fiber in the thermoplastic resin composition to have a weight-average fiber length of 300 to 400 μm while allowing the glass fiber filaments with a fiber length of 300 μm or less to account for 20 to 40 wt % of the total quantity of the glass fiber. As a result, in the high speed compression, a square prism shaped molded article prepared by melt molding of the thermoplastic resin composition will be able to show a larger displacement when load becomes zero, a larger initial load, and a larger displacement range included in initial load ±2 kN.

The thermoplastic resin composition can be processed by melt molding. Any appropriate molding method may be used to produce a product of any appropriate shape. Applicable molding methods include, for example, extrusion molding, injection molding, hollow molding, calender molding, compression molding, vacuum molding, and foam molding. Applicable molding shapes include, for example, square prism, round bar, pellet, plate, film, sheet, pipe, hollow, and box.

In particular, the thermoplastic resin composition is used favorably to produce square prism- or round bar-like molded articles to be used as shock absorbing members because square prism specimens subjected to high speed compression test shows a large displacement when load becomes zero and a constant load unchanged with changing displacement (showing a high-load square wave) in a high load range. It serves to provide products that are intended particularly for uses that require a high shock absorbing capability while maintaining a small size and low cost. For example, such products are used favorably as shock absorbing interior and exterior members for automobiles such as crushable boxes, air bag parts, pillars, fenders, and door panels for automobiles.

In addition, molded articled prepared by melt molding of the thermoplastic resin composition have strength, rigidity, impact resistance, and heat resistance in good balance, and can be used for various uses including electronic parts, electric equipment parts, household goods, office equipment, automobile and vehicle related parts, building materials, and sporting goods, as well as the aforementioned shock absorbing interior and exterior members for automobiles.

Such electronic parts include, for example, connector, coil, sensor, LED lamp, socket, resistor, relay case, small switch, coil bobbin, capacitor, variable capacitor case, optical pickup, oscillator, various terminal plates, transformer, plug, print substrate, tuner, speaker, microphone, headphone, small motor, magnetic head base, power module, semiconductor, liquid crystal, FDD carriage, FDD chassis, motor brush holder, parabolic antenna, and computer related parts.

Such electric equipment parts include, for example, power generator, electric motor, potential transformer, current transformer, voltage regulator, rectifier, inverter, relay, contact for electric power equipment, switch, shutoff device, knife switch, multiple rod, and electric parts cabinet.

Such household goods and office equipment include, for example, VTR parts, TV parts, iron, hair drier, rice cooker parts, microwave oven parts, sound parts, parts for audio/video devices such as audio/laser disk (registered trademark), compact disc, and DVD, lighting parts, refrigerator parts, air conditioner parts, typewriter parts, word processor parts, houses of electronic instruments such as personal computer and notebook computer, office computer related parts, telephone related parts, facsimile related parts, copier related parts, jig for cleaning device, motor parts, lighter, typewriter, microscope, binocular, camera, and clock.

Such automobile/vehicle related parts include, for example, alternator terminal, alternator connector, IC regulator, potentiometer base for lamp dimmer, various valves such as exhaust gas valve, various pipes, hoses, and tubes for fuel system, cooling system, brake system, wiper system, exhaust system, and suction system, air intake nozzle snorkel, intake manifold, fuel pump, engine cooling water joint, carburetor main body, carburetor spacer, exhaust gas sensor, cooling water sensor, oil temperature sensor, brake pad wear sensor, throttle position sensor, crank shaft position sensor, air flow meter, brake pad abrasion sensor, battery accessories, air conditioner thermostat base, heating air flow control valve, radiator motor brush holder, water pump impeller, turbine vane, wiper motor relation parts, distributor, starter switch, starter relay, transmission wire harness, transmission oil pan, window washer nozzle, air conditioner panel switch substrate, fuel related electromagnetic valve coil, various connectors such as wire harness connector, SMJ connector, PCB connector, door grommet connector, fuse connector, hone terminal, electrical equipment parts insulation plate, step motor rotor, lamp socket, lamp reflector, lamp housing, brake piston, solenoid bobbin, engine oil pan, engine oil filter, ignition equipment case, torque control lever, safe belt parts, register blade, washer lever, wind regulator handle, wind regulator handle knob, passing light lever, sun visor bracket, instrument panel, air bag accessories, door pad, pillar, console box, various motor housing, roof rail, fender, garnish, roof panel, hood panel, trunk lid, door mirror stay, spoiler, hood louver, wheel cover, wheel cap, grill apron cover frame, lamp bezel, door handle, door molding, rear finisher, and wiper.

Such building materials include, for example, walls, roof/ceiling member related parts, wind member related parts, insulator related parts, floor related parts, base isolation/vibration control member related parts, and vital utilities related parts of large buildings and structures.

Such sporting goods include, for example, golf related goods such as golf club and shaft; body protectors for sports such as mask, helmet, chest protector, elbow pad, and knee pad for American football, baseball, soft ball and the like; shoe related goods such as soles of sports shoes; fishing related goods such as fishing pole and fishing line; summer sports related goods such as for surfing; winter sports related goods such as ski and snow board; and other indoor and outdoor sports related goods.

EXAMPLES

The advantageous effects of our compositions and methods are described in more detail below with reference to Examples. It should be noted that this disclosure should not be construed as limited to the Examples provided below.

The thermoplastic resin (A) used in Examples and Comparative Examples are listed below:

(A-1): polyamide 6 resin with a melting point of 225° C., a relative viscosity of 2.75 as measured in a 98% concentrated sulfuric acid solution at 25° C. with a resin concentration of 0.01 g/ml, and an amino-terminal content of $5.8 \times 10^{-5}$ mol/g.

(A-2): polyamide 66 resin with a melting point of 265° C., a relative viscosity of 3.60 as measured in a 98% concentrated sulfuric acid solution at 25° C. with a resin concentration of 0.01 g/ml, and an amino-terminal content of $3.7 \times 10^{-5}$ mol/g.

(A-3): polyamide 610 resin with a melting point of 225° C., a relative viscosity of 2.70 as measured in a 98% concentrated sulfuric acid solution at 25° C. with a resin concentration of 0.01 g/ml, and an amino-terminal content of $4.0 \times 10^{-5}$ mol/g.

(A-4): polyamide 11 resin with a melting point of 190° C., a relative viscosity of 2.55 as measured in a 98% concentrated sulfuric acid solution at 25° C. with a resin concentration of 0.01 g/ml, and an amino-terminal content of $4.0 \times 10^{-5}$ mol/g.

(A-5): polyamide 12 resin with a melting point of 180° C., a relative viscosity of 2.55 as measured in a 98% concentrated sulfuric acid solution at 25° C. with a resin concentration of 0.01 g/ml, and an amino-terminal content of $4.0 \times 10^{-5}$ mol/g.

(A-6): polyamide 66/6T=50/50 resin with a melting point of 295° C., a relative viscosity of 2.70 as measured in a 98% concentrated sulfuric acid solution at 25° C. with a resin concentration of 0.01 g/ml, and an amino-terminal content of $5.0 \times 10^{-5}$ mol/g.

(A-7): polybutylene terephthalate resin with a melting point of 225° C., an intrinsic viscosity of 0.70 as measured in an o-chlorophenol solution at 25° C. with a resin concentration of 0.5 wt %, and a carboxyl-terminal content of 35 eq/ton.

(A-8): polyethylene terephthalate resin with a melting point of 265° C., an intrinsic viscosity of 0.85 as measured in an o-chlorophenol solution at 25° C. with a resin concentration of 0.5 wt %, and an carboxyl-terminal content of 26 eq/ton.

(A-9): bisphenol A type polycarbonate resin TARFLON (registered trademark) A2600 (manufactured by Idemitsu Kosan Co., Ltd.) with a glass transition temperature 150° C., and a viscosity average molecular weight of 26,000 (converted from a solution viscosity measured using methylene chloride at a temperature of 25° C.).

(A-10): poly-L-lactic acid resin with a melting point of 170° C., a weight average molecular weight of 210,000 (measured by gel permeation chromatography, 1,1,1,3,3,3-hexafluoro-2-propanol used as eluant, PMMA-based conversion), and a D-form content of 1.2%.

(A-11): poly(2,6-dimethyl-1,4-phenylene oxide) resin with a glass transition temperature of 220° C., and a reduced viscosity of 0.50 as measured in a chloroform solution at 30° C. with a resin concentration 0.5 g/dl.

(A-12): polyphenylene sulfide resin with a melting point of 280° C., and a MFR of 500 g/30 min (315.5° C. under a load of 5 kg), containing 95 mol % of p-phenylene sulfide units.

(A-13): polypropylene resin with a melting point of 160° C., a MFR of 0.5 g/10 min (230° C. under a load of 2.16 kg), and a density of 0.910 g/cm$^3$, prepared by dry-blending 100 parts by weight of polypropylene resin, 1 part by weight of maleic anhydride, and 0.1 part by weight of radical-generating agent (PERHEXA 25B, manufactured by NOF Corporation), and melt-kneading them at a cylinder temperature 230° C.

The rubbery polymer having a reactive functional group (B) used in Examples and Comparative Examples are listed below:

(B-1): ethylene/methyl acrylate/glycidyl methacrylate (70/27/3) copolymer with a melt flow rate of 7(190° C. under a load of 2.16 kg), BONDFAST (registered trademark) BF7L (manufactured by Sumitomo Chemical Co., Ltd.).

(B-2): ethylene/methyl acrylate/glycidyl methacrylate (67/27/6) copolymer with a melt flow rate of 7 (190° C. under a load of 2.16 kg), BONDFAST (registered trademark) BF7M (manufactured by Sumitomo Chemical Co., Ltd.).

(B-3): maleic anhydride modified ethylene-1-butene copolymer, TAFMER (registered trademark) MH7020 (manufactured by Mitsui Chemicals Inc.).

(B-4): ethylene-glycidyl methacrylate copolymer-g-PMMA resin, Modipper (registered trademark) A4200 (manufactured by NOF Corporation).

The inorganic filler (C) used in Examples and Comparative Examples are listed below:

(C-1): glass fiber, T-249 (manufactured by Nippon Electric Glass Co., Ltd.).

(C-2): carbon fiber, TORAYCA (registered trademark) Cut Fiber TV14-006 (manufactured by Toray Industries, Inc.).

(C-3): kaolin, Satintone No. 5 (manufactured by BASF).

(C-4): glass fiber, T-289 (manufactured by Nippon Electric Glass Co., Ltd.).

(C-5): glass fiber, 3J-948 (manufactured by Nitto Boseki Co., Ltd.).

(C-6): glass fiber, T-747 GH (manufactured by Nippon Electric Glass Co., Ltd.).

(C-7): glass fiber, ECS03-350 (manufactured by Central Glass Co., Ltd.).

The dendritic polyester resin (E) used in Examples and Comparative Examples are listed below:

(E-1): Reference Example 1

The acid anhydride (F) used in Examples and Comparative Examples are listed below:

(F-1): succinic anhydride (manufactured by KISHIDA CHEMICAL Co., Ltd.).

The components other than (A), (B), (C), (E), and (F) used in Examples and Comparative Examples are listed below:
- (G-1): thermal stabilizer, IR1098 (manufactured by Chiba Specialty Chemicals Co., Ltd.).
- (G-2): thermal stabilizer, IR1010 (manufactured by Chiba Specialty Chemicals Co., Ltd.).
- (G-3): thermal stabilizer, PEP36 (supplied by Adeka Corporation CORPORATION).
- (G-4): thermal stabilizer, AO80 (supplied by Adeka Corporation CORPORATION).

The evaluations in Example and Comparative Example were made by the method described below:

(1) Injection Molding (1-1) Test pieces for evaluation of tensile modulus and tensile elongation at break in Reference Examples 2 to 19

Using an injection molding machine (NP7-1F) manufactured by Nissei Plastic Industrial Co., Ltd., the pellets prepared in each Reference Example were subjected to injection molding under the conditions of the cylinder temperature and mold temperature settings given in Table 2 and Table 4 and an injection pressure higher by 5 kgf/cm$^2$ than the lower limit pressure (minimum filling pressure) to prepare JIS-5A dumbbell type test pieces (with a length of 75 mm×end portion width of 12.5 mm×thickness of 2 mm).

(1-2) Test pieces for evaluation of tensile strength, flexural modulus, Charpy impact strength, deflection temperature under load and observation of morphology in Reference Examples 2 to 19, test pieces for evaluation of general physical properties, observation of morphology, and evaluation of glass fiber distribution in Examples and Comparative Examples.

Using an injection molding machine (SE75DUZ) manufactured by Sumitomo Heavy Industries, Ltd., the pellets prepared in each Reference Example, Example and Comparative Example were subjected to injection molding under the conditions of the cylinder temperature and mold temperature settings given in Table 2, Table 4, Table 6, Table 8, Table 10, Table 12, Table 14, and Table 16, an injection rate of 100 mm/sec, and an injection pressure higher by 5 kgf/cm$^2$ than the lower limit pressure (minimum filling pressure) to prepare ISO test pieces (with a length of 170 mm, end portion width of 20 mm, parallel portion length of 80 mm, parallel portion width of 10 mm, and thickness of 4 mm).

(1-3) Test pieces for high speed compression test

Using an injection molding machine (NEX1000) manufactured by Nissei Plastic Industrial Co., Ltd., the pellets prepared in each Reference Example, Example and Comparative Example were subjected to injection molding under the conditions of the cylinder temperature and mold temperature settings given in Table 2, Table 4, Table 6, Table 8, Table 10, Table 12, Table 14, and Table 16, and an injection pressure higher by 5 kgf/cm$^2$ than the lower limit pressure (minimum filling pressure) to prepare ASTM ½ inch test pieces (½ inch (12.7 mm)×½ inch (12.7 mm)×2 inch (50.8 mm)).

(2) Morphology Observation

A 1 to 2 mm square was cut out of the cross-sectional center portion of an ISO test piece prepared by injection molding, and rubbery polymer having a reactive functional group (B) was dyed with ruthenium tetroxide. A ultrathin section of 0.1 µm or less (about 80 nm) is sliced off from the dyed specimen using a ultra-microtome at −196° C., and the continuous phase and the dispersed phase were observed by transmission electron microscopy first at a magnification of 5,000. At this time, the thermoplastic resin (A) appears black or gray while rubbery polymer having a reactive functional group (B) appears white. If the continuous phase and the dispersed phase were not distinguished definitely at a magnification of 5,000, the magnification was increased gradually up to 35,000 until the continuous phase and the dispersed phase became observable. Dispersed phase domains with a maximum diameter of 10 nm or more were identified in the phase. Then, the magnification was increased to 35,000, and observation was performed to determine if fine particles with a particle diameter of 1 to 100 nm existed in the dispersed phase (B) of the rubbery polymer having a reactive functional group. The area occupied by fine particles the dispersed phase (B) of the rubbery polymer having a reactive functional group were calculated by using an image analyzing program Scion Image supplied by Scion Corporation. For their particle diameter, 10 particles are selected randomly from the image obtained, and the maximum and minimum sizes across the particles were measured and averaged, followed by calculating the number average of the average values for the 10 particles.

(3) Flowability

Using an injection molding machine (SG75H-MIV) manufactured by Sumitomo Heavy Industries, Ltd., injection molding was performed under the conditions of the cylinder temperature and mold temperature settings given in Table 2, Table 4, Table 6, Table 8, Table 10, Table 12, Table 14, and Table 16, and an injection pressure of 30 MPa to prepare bar flow test pieces (with a length of 200 mm, width of 10 mm, and thickness of 1 mm), followed by measuring the bar flow length at a holding pressure of zero. A longer flow length suggests a higher flowability.

(4) Evaluation of Tensile Modulus and Tensile Elongation at Break in Reference Examples 2 to 19

JIS-5A dumbbell type test pieces prepared by injection molding were subjected to a tensile test in Autographraph AG100 kNG (Shimadzu Corporation) with a chuck distance of 50 mm at three tension speeds of 100 mm/min, 500 mm/min, and 1,000 mm/min to measure the tensile modulus and tensile elongation at break at each speed. The tensile elongation at break is the rupture elongation ratio based on the chuck distance of 50 mm.

(5) Evaluation of Tensile Strength

Using ISO test pieces prepared by injection molding, a tensile test was carried out according to ISO527-1 and -2 in an atmosphere at a temperature of 23° C. and humidity 50% under the condition of a strain speed of 50 mm/min in Comparative Examples 1 to 3 and a strain speed of 5 mm/min in the other examples to measure the tensile strength.

(6) Evaluation of Tensile Elongation at Break for Examples and Comparative Examples Using ISO test pieces prepared by injection molding, a tensile test was carried out according to ISO527-1 and -2 in an atmosphere at a temperature of 23° C. and humidity 50% under the condition of a strain speed of 50 mm/min in Comparative Examples 1 to 3 and a strain speed of 5 mm/min in the other examples to measure the tensile elongation at break.

(7) Evaluation of Flexural Modulus (Rigidity)

Using ISO test pieces prepared by injection molding, a bending test was carried out according to ISO178 in an atmosphere at a temperature of 23° C. and humidity 50% under the condition of a strain speed of 2 mm/min to measure the flexural modulus.

(8) Evaluation of Charpy Impact Strength

Using ISO test pieces prepared by injection molding, a Charpy impact test (notched) was carried out according to ISO179 in an atmosphere at a temperature of 23° C. and humidity 50% to measure the impact strength.

(9) Evaluation of Deflection Temperature Under Load (Heat Resistance)

Using ISO test pieces prepared by injection molding, the deflection temperature under load was measured under a load of 0.45 MPa according to ISO75.

(10) High Speed Compression Test (as a Test for Shock Absorbing Members)

ASTM ½ inch test pieces prepared by injection molding were cut to provide square prism specimens (FIG. 1) with a cross section of 12.7 mm×12.7 mm and height 25.4 mm in which the flow of the thermoplastic resin composition was parallel to their height direction. With a high speed compression testing machine INSTRON 9250HV Dynatup, a load-displacement curve was obtained using a weight with a mass 26 kg which was allowed to fall freely from a height of 0.5 m (11 km/hour), and evaluations for the following items were evaluated according to FIG. 2. At Point (a), the load becomes zero, which means that the square prism specimen is destroyed.

(a) displacement when load becomes zero
(b) initial load
(c) displacement range included in initial load ±2 kN

(11) Evaluation of Distribution of Glass Fiber in Thermoplastic Resin Composition Since the length and distribution of glass fiber in a thermoplastic resin composition are maintained after melt molding, the length and distribution of glass fiber were measured for ISO test pieces prepared by injection molding. From an ISO test piece prepared by injection molding, an about 5 g portion was taken from a central parallel region, and heated for ashing in a crucible at 550° C. for 2.5 hours. An 8 mg portion of the glass fiber residue was sampled and dispersed in 40 cc of distilled water. Then, 0.3 ml of the dispersion liquid is put on a slide glass using a dropper, and observed and photographed at a magnification of 20 under an ECLIPSE 80i microscope manufactured by Nikon Corporation. For about 500 filaments of the photographed glass fiber, the weight-average fiber length of the glass fiber filaments and the proportion of the glass fiber filaments with a fiber length of 300 µm or less were measured using a WinROOF image analysis program.

On the assumption that the fiber diameter and density are constant, the weight-average fiber length of glass fiber was calculated by the following formula. In the formula, $L_i$ and $q_i$ represent the fiber length and the number of filaments with a fiber length $L_i$. The fiber length $L_i$ is assumed to be 4.8 µm or more.

Weight-average fiber length=$\Sigma(q_i \times L_i^2)/\Sigma(q_i \times L_i)$

On the assumption that the fiber diameter and density are constant, the proportion of glass fiber filaments with a length of 300 µm or less was calculated from the fiber length distribution. The fiber length is assumed to be 4.8 µm or more.

Reference Example 1

In a 500 mL reaction container equipped with stirring blades and a distillation tube, 51.93 g (0.38 moles) of p-hydroxybenzoic acid, 19.1 g (0.10 moles) of 4,4'-dihydroxy biphenyl, 5.86 g (0.035 moles) of terephthalic acid, 21.2 g (0.10 moles) of trimesic acid, 5.55 g (0.045 moles) of benzoic acid, 11.3 g (0.059 moles) of polyethylene terephthalate with an intrinsic viscosity of about 0.6 dl/g, and 65.3 g of acetic anhydride (1.10 equivalents of total phenolic hydroxyl groups) were fed, and stirred for reaction in a nitrogen gas atmosphere at 145° C. for 2 hours. The resulting material was heated for 3 hours up to 290° C., and then the pressure was reduced for 30 minutes down to 1.0 mm Hg (133 Pa) with the polymerization temperature held at 290° C. The polymerization reaction was stopped when the stirring torque reached 2.5 kg·cm, and then the contents was transferred into water. The resulting dendritic polyester resin (E-1) was heated and dried at 110° C. for 4 hours, crushed with a blender, and washed with ethanol and deionized water. Subsequently, a vacuum heater-dryer was used to perform vacuum drying at 110° C. for 16 hours, and the resulting powdery dendritic polyester resin (E-1) was subjected to various measurements.

The resulting dendritic polyester resin (E-1) was analyzed by nuclear magnetic resonance spectroscopy and found to have a trimesic acid content of 14 mol %. Specifically, the dendritic polyester resin (E-1) was dissolved in a mixed solvent of 50 wt % pentafluorophenol and 50 wt % deuterated chloroform, and the resulting solution was analyzed by proton nuclear magnetic resonance spectroscopy at 40° C. The detected peaks included those from p-oxybenzoate units at 7.44 ppm and 8.16 ppm, from 4,4'-dioxybiphenyl units at 7.04 ppm and 7.70 ppm, from terephthalate units at 8.31 ppm, from ethylene oxide units at 4.75 ppm, and from trimesic acid at 9.25 ppm. From the integrated peak intensity ratio, the content of trimesic acid was calculated and rounded to the nearest whole number.

The resulting dendritic polyester resin (E-1) has a melting point of 235° C., a liquid crystallization start temperature of 191° C., and a number average molecular weight of 12,500. The melt viscosity was measured using a constant-load, orifice-type flow tester at temperature of 270° C. and a shear velocity of 100/s and found to be 18 Pa·s. To determine the melting point (Tm) by differential scanning calorimetry, the dendritic polyester resin (E-1) was heated from room temperature at a heating rate of 20° C./min while measuring the endothermic peak temperature (Tm1), and then it was maintained at a temperature higher by 20° C. than Tm1 for 5 minutes, cooled to room temperature at a cooling rate of 20° C./min, and heated again at a heating rate of 20° C./min to measure the endothermic peak temperature (Tm). To determine the liquid crystallization start temperature, the resin was observed in a shearing-heating apparatus (CSS-450) under the conditions of a shear velocity of 100 (1/sec), heating rate 5.0° C./min, and objective lens magnification of 60 to determine the temperature at which the material started to flow in the entire field of view. The number average molecular weight was measured by GPC (gel penetrate chromatography) under the conditions described below:

Column: K-806M (×2), K-802 (×1) (manufactured by Showa Denko K.K.)
Solvent: pentafluorophenol/chloroform (35/65 by wt %)
Flow rate: 0.8 mL/min
Specimen concentration: 0.08 g/L
Injection volume: 0.200 mL
Temperature: 23° C.
Detector: differential refractive index (RI) detector (RI-8020, manufactured by Tosoh Corporation)
Calibration curve: calibration curve based on monodisperse polystyrene.

Reference Examples 2 to 18

The required components were mixed in the proportions given in Tables 1 and 3 and processed by melt kneading under a nitrogen flow at a cylinder temperature, screw rotating speed, and extrusion rate as given in Tables 1 to 4 in a complete intermeshing type co-rotating twin screw extruder (TEX-65αII, manufactured by Japan Steel Works, Ltd.) equipped with two double-thread screws with a screw diameter of 65 mm and a L/D ratio of 31.5, thereby discharging a molten resin strand from the outlet (L/D=31.5). The screw used is configured so that twist kneading disks in which the spiral angle θ between the apex of the front end side of the kneading disk and the apex of its rear surface side is 20° in the caracole direction of the screw are interlinked over a length of Lk/D=4.0 starting at a position where L/D=10, thereby forming zones (elongational flow zones) where the material is subjected to melt kneading under elongational flow. In addition, a reverse screw zone with an L/D ratio of 0.5 was provided on the downstream side of the elongational flow zones. The proportion (%) of the total length of the elongational flow zones to the overall screw length was calculated at 13% by the following formula: (total length of elongational flow zones)/(overall screw length)×100. The inflow-effect pressure fall between the inlet and outlet of the elongational flow zone was calculated at 150 kg/cm$^2$ (14.7 MPa) by subtracting the pressure difference ($\Delta P_0$) in the elongational flow zone from the pressure difference ($\Delta P$) immediately before the twist kneading disks. Furthermore, mixing screws having notch section including single thread screws with a screw pitch of 0.25 D and 12 notches per pitch were interlinked over a length of Lm/D=4.0 starting at positions where L/D=16 or 21, respectively, thereby forming two mixing zones. The proportion (%) of the total length of the mixing zones to the overall screw length was calculated at 25% by the following formula: (total length of mixing zones)/(overall screw length)×100. In addition, 75% of the mixing screws having notch section that constituted the mixing zones had a thread direction opposite to the screw axis rotation direction. This screw configuration is referred to as configuration (I). A vent vacuum zone is provided at a position where L/D=27, and the volatile components were removed at a gauge pressure of −0.1 MPa. As the molten resin having passed the die head was discharged from 4 mm diameter×23 holes, the molten resin was observed visually to see if gelled material was contained while measuring the temperature of the molten resin with a thermometer. Subsequently, the discharged resin was pulled to produce a strand and cooled as it passed through a cooling bath, and it was cut by a pelletizer while being taken up, thus providing pellets of thermoplastic resin-rubbery polymer composite composition (A-B). The pellets were then vacuum-dried at 80° C. for 12 hours or more, and subsequently subjected to injection molding as described above, followed by various evaluations. The kneading conditions used and various evaluation results obtained are given in Tables 1 to 4.

Reference Example 19

The required components were mixed in the proportions given in Table 3 and processed by melt kneading under a nitrogen flow at a cylinder temperature, screw rotating speed, and extrusion rate as given in Tables 3 and 4 in a complete intermeshing type co-rotating twin screw extruder (TEX-65αII, manufactured by Japan Steel Works, Ltd.) equipped with two double-thread screws with a screw diameter of 65 mm and a L/D ratio of 35, thereby discharging a molten resin strand from the outlet (L/D=35). The screw configuration was such that three kneading zones, starting at positions where L/D=7, 16, or 25, respectively, were provided, and the kneading zones had lengths Lk/D of 3.0, 3.0, and 3.0, respectively. In addition, a reverse screw zone is provided on the downstream side of each kneading zone, and the reverse screw zones had lengths Lr/D of 0.5, 0.5, and 0.5, respectively. The proportion (%) of the total length of the kneading zone to the overall screw length was calculated at 26% by the following formula: (total length of kneading zones)/(overall screw length)×100. This screw configuration is referred to as configuration (II). A vent vacuum zone is provided at a position where L/D=30, and the volatile components were removed at a gauge pressure of −0.1 MPa. As the molten resin having passed the die head was discharged from 4 mm diameter×23 holes, the molten resin was observed visually to see if gelled material was contained while measuring the temperature of the molten resin with a thermometer. Subsequently, the discharged resin was pulled to produce a strand and cooled as it passed through a cooling bath, and it was cut by a pelletizer while being taken up, thus providing pellets of thermoplastic resin-rubbery polymer composite composition (A-B). The pellets were then vacuum-dried at 80° C. for 12 hours or more, and subsequently subjected to injection molding as described above, followed by various evaluations. The kneading conditions used and various evaluation results obtained are given in Tables 3 and 4.

TABLE 1

| | | | | Reference Example | | | | | | | | |
|---|---|---|---|---|---|---|---|---|---|---|---|---|
| | | | | 2 | 3 | 4 | 5 | 6 | 7 | 8 | 9 | 10 |
| Compounding ratio | thermoplastic resin (A) | A-1 | parts by weight | 70 | 80 | 60 | 70 | 70 | 0 | 0 | 0 | 0 |
| | | A-2 | parts by weight | 0 | 0 | 0 | 0 | 0 | 70 | 0 | 0 | 0 |
| | | A-3 | parts by weight | 0 | 0 | 0 | 0 | 0 | 0 | 70 | 0 | 0 |
| | | A-4 | parts by weight | 0 | 0 | 0 | 0 | 0 | 0 | 0 | 70 | 0 |
| | | A-5 | parts by weight | 0 | 0 | 0 | 0 | 0 | 0 | 0 | 0 | 70 |
| | rubbery polymer having a reactive functional group (B) | B-1 | parts by weight | 30 | 20 | 40 | 15 | 0 | 0 | 0 | 30 | 30 |
| | | B-2 | parts by weight | 0 | 0 | 0 | 0 | 0 | 30 | 30 | 0 | 0 |
| | | B-3 | parts by weight | 0 | 0 | 0 | 15 | 30 | 0 | 0 | 0 | 0 |
| | thermal stabilizer (G) | G-1 | parts by weight | 0.2 | 0.2 | 0.2 | 0.2 | 0.2 | 0.2 | 0.2 | 0.2 | 0.2 |
| | | G-2 | parts by weight | 0.2 | 0.2 | 0.2 | 0.2 | 0.2 | 0.2 | 0.2 | 0.2 | 0.2 |

TABLE 1-continued

| | | | Reference Example | | | | | | | | |
|---|---|---|---|---|---|---|---|---|---|---|---|
| | | | 2 | 3 | 4 | 5 | 6 | 7 | 8 | 9 | 10 |
| Melt kneading | screw diameter of twin screw extruder | mm | 65 | 65 | 65 | 65 | 65 | 65 | 65 | 65 | 65 |
| | L/D of twin screw extruder | — | 31.5 | 31.5 | 31.5 | 31.5 | 31.5 | 31.5 | 31.5 | 31.5 | 31.5 |
| | screw configuration | — | I | I | I | I | I | I | I | I | I |
| | Elongational flow zone existent/absent | — | existent | existent | existent | existent | existent | existent | existent | existent | existent |
| | inflow-effect pressure fall | kg/cm² | 150 | 150 | 150 | 150 | 150 | 150 | 150 | 150 | 150 |
| | proportion to overall length | % | 13 | 13 | 13 | 13 | 13 | 13 | 13 | 13 | 13 |
| | size of each elongational flow zone (Lk/D) | — | 4 | 4 | 4 | 4 | 4 | 4 | 4 | 4 | 4 |
| | number of elongational flow zones | number | 1 | 1 | 1 | 1 | 1 | 1 | 1 | 1 | 1 |
| | cylinder temperature setting | °C. | 230 | 230 | 230 | 230 | 230 | 260 | 230 | 200 | 200 |
| | mixing zone existent/absent | — | existent | existent | existent | existent | existent | existent | existent | existent | existent |
| | proportion to overall length | % | 25 | 25 | 25 | 25 | 25 | 25 | 25 | 25 | 25 |
| | size of each mixing zone (Lm/D) | — | 4 | 4 | 4 | 4 | 4 | 4 | 4 | 4 | 4 |
| | number of mixing zones | number | 2 | 2 | 2 | 2 | 2 | 2 | 2 | 2 | 2 |
| | cylinder temperature setting | °C. | 230 | 230 | 230 | 230 | 230 | 260 | 230 | 200 | 200 |
| | cylinder temperature setting outside elongational flow zones and mixing zones | °C. | 240 | 240 | 240 | 240 | 240 | 270 | 240 | 210 | 210 |
| | screw rotating speed | rpm | 350 | 350 | 270 | 250 | 250 | 350 | 350 | 350 | 350 |
| | extrusion rate | kg/h | 200 | 200 | 200 | 200 | 200 | 200 | 200 | 200 | 200 |
| | discharged resin temperature | °C. | 320 | 307 | 330 | 325 | 330 | 340 | 310 | 275 | 270 |
| | existent/absent of gelled material | — | absent | absent | absent | absent | absent | absent | absent | absent | absent |

TABLE 2

| | | | Reference Example | | | | | | | | |
|---|---|---|---|---|---|---|---|---|---|---|---|
| | | | 2 | 3 | 4 | 5 | 6 | 7 | 8 | 9 | 10 |
| Morphology | continuous phase resin | — | A | A | A | A | A | A | A | A | A |
| | dispersed phase resin | — | B | B | B | B | B | B | B | B | B |
| | existent/absent of 1 to 100 nm fine particles in dispersed phase | — | existent | existent | existent | existent | existent | existent | existent | existent | existent |
| | proportion of 1 to 100 nm fine particles in dispersed phase | % | 24 | 20 | 25 | 24 | 23 | 23 | 22 | 22 | 23 |
| Molding | cylinder temperature setting | °C. | 250 | 250 | 250 | 250 | 250 | 290 | 250 | 215 | 205 |
| | mold temperature setting | °C. | 80 | 80 | 80 | 80 | 80 | 80 | 80 | 80 | 80 |
| Flowability | flow length | mm | 37 | 50 | 22 | 28 | 25 | 20 | 35 | 40 | 40 |
| General physical properties | tensile modulus 100 mm/min | GPa | 1.4 | 1.7 | 1.1 | 1.3 | 1.2 | 1.4 | 1.3 | 0.9 | 0.8 |
| | 500 mm/min | GPa | 1.3 | 1.6 | 1.0 | 1.1 | 1.1 | 1.2 | 1.1 | 0.7 | 0.6 |
| | 1,000 mm/min | GPa | 1.0 | 1.5 | 0.8 | 0.9 | 0.9 | 1.0 | 1.0 | 0.6 | 0.5 |
| | (1,000 mm/min) − (100 mm/min) | GPa | −0.4 | −0.2 | −0.3 | −0.4 | −0.3 | −0.4 | −0.3 | −0.3 | −0.3 |
| | tensile elongation at break 100 mm/min | % | 119 | 110 | 97 | 140 | 118 | 100 | 150 | 110 | 123 |
| | 500 mm/min | % | 136 | 100 | 105 | 152 | 130 | 112 | 162 | 120 | 135 |
| | 1,000 mm/min | % | 141 | 90 | 113 | 167 | 135 | 116 | 170 | 125 | 140 |
| | (1,000 mm/min) − (100 mm/min) | % | 22 | −20 | 16 | 27 | 17 | 16 | 20 | 15 | 17 |
| | tensile strength ISO527-1, 2 | MPa | 43 | 50 | 32 | 40 | 36 | 44 | 40 | 24 | 23 |
| | flexural modulus ISO178 | GPa | 1.5 | 1.6 | 1.1 | 1.3 | 1.1 | 1.6 | 1.3 | 0.9 | 0.8 |
| | Charpy impact strength ISO179 | kJ/m² | 107 | 78 | 98 | 129 | 130 | 96 | 102 | 90 | 90 |
| | deflection temperature under load ISO75, 0.45 MPa | kJ/m² | 85 | 95 | 65 | 80 | 75 | 100 | 78 | 60 | 62 |
| High speed compression test (as test for shock absorption members) | displacement when load becomes zero | mm | >10 | >10 | >10 | >10 | >10 | >10 | >10 | >10 | >10 |
| | initial load | kN | 9.5 | 11.0 | 7.0 | 8.5 | 7.5 | 9.3 | 8.0 | 6.0 | 6.0 |
| | displacement range included in initial load ±2 kN | mm | <2 | <2 | <2 | <2 | <2 | <2 | <2 | <2 | <2 |

TABLE 3

| | | | | Reference Example | | | | | | | | |
|---|---|---|---|---|---|---|---|---|---|---|---|---|
| | | | | 11 | 12 | 13 | 14 | 15 | 16 | 17 | 18 | 19 |
| Compounding ratio | thermoplastic resin (A) | A-1 | parts by weight | 0 | 0 | 0 | 0 | 0 | 0 | 0 | 0 | 70 |
| | | A-6 | parts by weight | 70 | 0 | 0 | 0 | 0 | 0 | 0 | 0 | 0 |
| | | A-7 | parts by weight | 0 | 75 | 0 | 0 | 0 | 0 | 0 | 0 | 0 |
| | | A-8 | parts by weight | 0 | 0 | 75 | 0 | 0 | 0 | 0 | 0 | 0 |
| | | A-9 | parts by weight | 0 | 0 | 0 | 70 | 0 | 0 | 0 | 0 | 0 |
| | | A-10 | parts by weight | 0 | 0 | 0 | 0 | 70 | 0 | 0 | 0 | 0 |
| | | A-11 | parts by weight | 0 | 0 | 0 | 0 | 0 | 70 | 0 | 0 | 0 |
| | | A-12 | parts by weight | 0 | 0 | 0 | 0 | 0 | 0 | 75 | 0 | 0 |
| | | A-13 | parts by weight | 0 | 0 | 0 | 0 | 0 | 0 | 0 | 70 | 0 |
| | rubbery polymer having a reactive functional group (B) | B-1 | parts by weight | 30 | 0 | 0 | 0 | 0 | 0 | 0 | 0 | 30 |
| | | B-2 | parts by weight | 0 | 0 | 25 | 30 | 30 | 30 | 25 | 30 | 0 |
| | | B-4 | parts by weight | 0 | 25 | 0 | 0 | 0 | 0 | 0 | 0 | 0 |
| | thermal stabilizer (G) | G-1 | parts by weight | 0.2 | 0 | 0 | 0 | 0 | 0 | 0 | 0 | 0.2 |
| | | G-2 | parts by weight | 0.2 | 0.2 | 0.2 | 0.2 | 0.2 | 0.2 | 0 | 0.2 | 0.2 |
| | | G-3 | parts by weight | 0 | 0 | 0 | 0 | 0 | 0 | 0.2 | 0 | 0 |
| | | G-4 | parts by weight | 0 | 0 | 0 | 0 | 0 | 0 | 0.2 | 0 | 0 |
| Melt kneading | screw diameter of twin screw extruder | | mm | 65 | 65 | 65 | 65 | 65 | 65 | 65 | 65 | 65 |
| | L/D of twin screw extruder | | — | 31.5 | 31.5 | 31.5 | 31.5 | 31.5 | 31.5 | 31.5 | 31.5 | 35 |
| | screw configuration | | — | I | I | I | I | I | I | I | I | II |
| | elongational flow zone | existent/absent | — | existent | existent | existent | existent | existent | existent | existent | existent | absent |
| | | inflow-effect pressure fall | kg/cm² | 150 | 150 | 150 | 150 | 150 | 150 | 150 | 150 | — |
| | | proportion to overall length | % | 13 | 13 | 13 | 13 | 13 | 13 | 13 | 13 | — |
| | | size of each elongational flow zone (Lk/D) | — | 4 | 4 | 4 | 4 | 4 | 4 | 4 | 4 | — |
| | | number of elongational flow zones | number | 1 | 1 | 1 | 1 | 1 | 1 | 1 | 1 | — |
| | | cylinder temperature setting | °C. | 280 | 230 | 260 | 250 | 200 | 280 | 280 | 200 | — |
| | mixing zone | existent/absent | — | existent | existent | existent | existent | existent | existent | existent | existent | absent |
| | | proportion to overall length | % | 25 | 25 | 25 | 25 | 25 | 25 | 25 | 25 | — |
| | | size of each mixing zone (Lm/D) | — | 4 | 4 | 4 | 4 | 4 | 4 | 4 | 4 | — |
| | | number of mixing zones | number | 2 | 2 | 2 | 2 | 2 | 2 | 2 | 2 | — |
| | | cylinder temperature setting | °C. | 280 | 230 | 260 | 250 | 200 | 280 | 280 | 200 | — |

TABLE 4

| | | | | Reference Example | | | | | | | | |
|---|---|---|---|---|---|---|---|---|---|---|---|---|
| | | | | 11 | 12 | 13 | 14 | 15 | 16 | 17 | 18 | 19 |
| Melt kneading | cylinder temperature setting outside elongational flow zones and mixing zones | | °C. | 290 | 240 | 270 | 260 | 210 | 290 | 290 | 210 | 250 |
| | screw rotating speed | | rpm | 300 | 350 | 350 | 350 | 350 | 350 | 350 | 300 | 150 |
| | extrusion rate | | kg/h | 200 | 200 | 200 | 200 | 200 | 200 | 200 | 200 | 400 |
| | discharged resin temperature | | °C. | 346 | 322 | 336 | 323 | 245 | 345 | 344 | 250 | 276 |
| | existent/absent of gelled material | | — | absent | absent | absent | absent | Absent | absent | absent | absent | absent |
| Morphology | continuous phase resin | | — | A | A | A | A | A | A | A | A | A |
| | dispersed phase resin | | — | B | B | B | B | B | B | B | B | B |
| | existent/absent of 1 to 100 nm fine particles in dispersed phase | | — | existent | existent | existent | existent | Existent | existent | existent | existent | existent |
| | proportion of 1 to 100 nm fine particles in dispersed phase | | % | 22 | 16 | 16 | 14 | 15 | 17 | 21 | 15 | 3 |
| Molding | cylinder temperature setting | | °C. | 320 | 250 | 290 | 250 | 195 | 320 | 305 | 185 | 250 |
| | mold temperature setting | | °C. | 130 | 80 | 130 | 80 | 80 | 130 | 130 | 40 | 80 |
| Flowability | flow length | | mm | 30 | 40 | 43 | 46 | 47 | 20 | 35 | 50 | 60 |
| General physical properties | tensile modulus | 100 mm/min | GPa | 1.3 | 1.3 | 1.0 | 1.4 | 1.7 | 1.4 | 1.5 | 0.9 | 1.4 |
| | | 500 mm/min | GPa | 1.2 | 1.2 | 0.7 | 1.3 | 1.6 | 1.3 | 1.4 | 0.8 | 1.4 |
| | | 1,000 mm/min | GPa | 1.0 | 1.0 | 0.6 | 1.2 | 1.4 | 1.1 | 1.1 | 0.7 | 1.6 |
| | | (1000 mm/min) − (100 mm/min) | GPa | −0.3 | −0.3 | −0.4 | −0.2 | −0.3 | −0.3 | −0.4 | −0.2 | 0.2 |
| | tensile elongation at break | 100 mm/min | % | 112 | 90 | 95 | 70 | 60 | 63 | 122 | 87 | 108 |
| | | 500 mm/min | % | 118 | 95 | 110 | 80 | 72 | 70 | 139 | 100 | 105 |
| | | 1000 mm/min | % | 124 | 104 | 112 | 84 | 75 | 80 | 144 | 106 | 93 |
| | | (1,000 mm/min) − (100 mm/min) | % | 12 | 14 | 17 | 14 | 15 | 17 | 22 | 19 | −15 |
| | tensile strength | ISO527-1, 2 | MPa | 44 | 31 | 23 | 39 | 39 | 35 | 44 | 22 | 41 |
| | flexural modulus | ISO178 | GPa | 1.5 | 1.3 | 1.0 | 1.4 | 1.7 | 1.3 | 1.6 | 1.0 | 1.5 |

TABLE 4-continued

| | | | | Reference Example | | | | | | | | |
|---|---|---|---|---|---|---|---|---|---|---|---|---|
| | | | | 11 | 12 | 13 | 14 | 15 | 16 | 17 | 18 | 19 |
| | Charpy impact strength | ISO179 | kJ/m$^2$ | 72 | 83 | 75 | 65 | 70 | 55 | 97 | 70 | 99 |
| | deflection temperature under load | ISO75, 0.45 MPa | kJ/m$^2$ | 112 | 78 | 65 | 80 | 52 | 186 | 102 | 50 | 82 |
| High speed compression test (as test for shock absorption members) | displacement when load becomes zero | | mm | >10 | >10 | >10 | >10 | >10 | >10 | >10 | >10 | >10 |
| | initial load | | kN | 9.5 | 6.8 | 6.0 | 8.0 | 8.3 | 7.0 | 9.0 | 5.8 | 9.1 |
| | displacement range included in initial load ±2 kN | | mm | <2 | <2 | <2 | <2 | <2 | <2 | <2 | <2 | <2 |

In Reference Examples 2 to 18, the process for melt-kneading thermoplastic resin (A) and rubbery polymer having a reactive functional group (B) is controlled elaborately so that the dispersed phase (B) contains fine particles with a particle diameter of 1 to 100 nm formed of a compound resulting from the reaction between thermoplastic resin (A) and rubbery polymer having a reactive functional group (B) and that the area occupied by the fine particles account for 10% or more of the area of the dispersed phase (B) of the rubbery polymer having a reactive functional group. Except for Reference Example 3, results of the tensile tests show that the tensile modulus decreases and the tensile elongation at break increases as the tension speed increases. However, results of the high speed compression test for square prism specimens suggest that although the displacement when load becomes zero is large, the initial load is small and the displacement range included in initial load ±2 kN is small (less likely to give a square wave).

In Reference Example 19, the process for melt-kneading the thermoplastic resin (A) and the rubbery polymer having a reactive functional group (B) is not controlled elaborately, and consequently, although the dispersed phase (B) of the rubbery polymer having a reactive functional group contains a small amount of fine particles with a particle diameter of 1 to 100 nm formed of a compound resulting from a reaction between the thermoplastic resin (A) and the rubbery polymer having a reactive functional group (B), the area occupied by the fine particles account for only less than 10% of the area of the dispersed phase (B). It is also seen from the results of the tensile tests that the tensile modulus increases and the tensile elongation at break decreases as the tension speed increases. Furthermore, results of the high speed compression test for square prism specimens suggest that although the displacement when load becomes zero is large, the initial load is small and the displacement range included in initial load ±2 kN is small (less likely to give a square wave).

Examples 1 to 12 and 14 to 29 and Comparative Examples 3 to 6, 8, 12, 13

The required components were mixed in the proportions given in Tables 5, 7, 9, 11, 13, and 15 and processed by melt kneading under a nitrogen flow at a cylinder temperature, screw rotating speed, and extrusion rate as given in Tables 5, 7, 9, 11, 13, and 15 in a complete intermeshing type co-rotating twin screw extruder (TEX-65αII, manufactured by Japan Steel Works, Ltd.) equipped with two double-thread screws with a screw diameter of 65 mm and a L/D ratio of 35, thereby discharging a molten resin strand from the outlet (L/D=35). The screw configuration was such that three kneading zones, starting at positions where L/D=7, 16, or 25, respectively, were provided, and the kneading zones had lengths Lk/D of 3.0, 3.0, and 3.0, respectively. In addition, a reverse screw zone is provided on the downstream side of each kneading zone, and the reverse screw zones had lengths Lr/D of 0.5, 0.5, and 0.5, respectively. The proportion (%) of the total length of the kneading zones to the overall screw length was calculated at 26% by the following formula: (total length of kneading zones)/(overall screw length)×100. This screw configuration is referred to as configuration (III). Furthermore, a side feeder is provided at a position where L/D=23, and the materials were fed from the root of the extruder (a position where L/D=1) (a 3% position assuming that the materials are fed from near the upstream end while molten resin is discharged from near the downstream end and that the upstream end of the screw is located at the 0% position while the downstream end of the screw is located at the 100% position) and also from a midstream position (a position where L/D=23) (a 66% position assuming that the materials are fed from near the upstream end while molten resin is discharged from near the downstream end and that the upstream end of the screw is located at the 0% position while the downstream end of the screw is located at the 100% position) as specified in Tables 5, 7, 9, 11, 13, and 15. A vent vacuum zone is provided at a position where L/D=30, and the volatile components were removed at a gauge pressure of −0.1 MPa. Subsequently, the molten resin having passed the die head and being discharged from 4 mm diameter×23 holes was pulled to produce a strand and cooled as it passed through a cooling bath, and it was cut by a pelletizer while being taken up, thus providing pellets of a thermoplastic resin composition. The pellets were then vacuum-dried at 80° C. for 12 hours or more and subsequently subjected to injection molding as described above, followed by various evaluations. The kneading conditions used and various evaluation results obtained are given in Tables 5 to 16.

Example 13

The required components were mixed in the proportions given in Table 7 and processed by melt kneading under a nitrogen flow at a cylinder temperature, screw rotating speed, and extrusion rate as given in Table 7 in a complete intermeshing type co-rotating twin screw extruder (TEX-65αII, manufactured by Japan Steel Works, Ltd.) equipped with two double-thread screws with a screw diameter of 65 mm and a L/D ratio of 45, thereby discharging a molten resin strand from the outlet (L/D=45). The screw used is configured so that twist kneading disks in which the spiral angle θ between the apex of the front end side of the kneading disk and the apex of its rear surface side is 20° in the caracole direction of the screw are interlinked over a length of Lk/D=4.0 starting at a position where L/D=10, thereby forming zones (elongational flow zones) where the material is subjected to melt kneading under elongational flow. In addition, a reverse screw zone with an L/D ratio of 0.5 was provided on the downstream side of the elongational flow zone. The proportion (%) of the total length of elongational flow zones to the overall screw length was calculated at 9% by the following formula: (total length of elongational flow zone)/(overall screw length)×100. The inflow-effect pressure fall between the inlet and outlet of the elongational flow zone was calculated at 150 kg/cm$^2$ (14.7 MPa) by subtracting the pressure difference ($\Delta P_0$) in the elongational flow zone from the pressure difference ($\Delta P$) immediately before the twist kneading disks. Furthermore, mixing screws having notch section including single thread screws with a screw pitch of 0.25 D and 12 notches per pitch were interlinked over a length of Lm/D=4.0 starting at positions where L/D=16 or 21, respectively, thereby forming two mixing zones. The proportion (%) of the total length of mixing zones to the overall screw length was calculated at 18% by the following formula: (total length of mixing zones)/(overall screw length)×100. In addition, 75% of the mixing screws having notch section that constituted the mixing zones had a thread direction opposite to the screw axis rotation direction. Furthermore, a kneading zone with a Lk/D ratio of 3.0 was provided at a position where L/D=35 and a reverse screw zone with a Lr/D ratio of 0.5 was provided in its downstream side. This screw configuration is referred to as configuration (IV). A side feeder is provided at a position where L/D=33, and the materials were fed from the root of the extruder (a position where L/D=1) (a 2% position assuming that the materials are fed from near the upstream end while molten resin is discharged from near the downstream end and that the upstream end of the screw is located at the 0% position while the downstream end of the screw is located at the 100% position) and also from a midstream position (a position where L/D=33) (a 73% position assuming that the materials are fed from near the upstream end while molten resin is discharged from near the downstream end and that the upstream end of the screw is located at the 0% position while the downstream end of the screw is located at the 100% position) as specified in Table 7. A vent vacuum zone is provided at a position where L/D=40, and the volatile components were removed at a gauge pressure of –0.1 MPa. As the molten resin having passed the die head was discharged from 4 mm diameter×23 holes, the molten resin was observed visually to see if gelled material was contained while measuring the temperature of the molten resin with a thermometer. Subsequently, the discharged resin was pulled to produce a strand and cooled as it passed through a cooling bath, and it was cut by a pelletizer while being taken up, thus providing pellets of a thermoplastic resin composition. The pellets were then vacuum-dried at 80° C. for 12 hours or more, and subsequently subjected to injection molding as described above, followed by various evaluations. The kneading conditions used and various evaluation results obtained are given in Tables 7 and 8.

Comparative Example 1

The pellets of (A-1) were then vacuum-dried at 80° C. for 12 hours or more, and subsequently subjected to injection molding as described above, followed by various evaluations. Results of the various evaluations are given in Table 14.

Comparative Example 2

The pellets prepared in Reference Example 2 were vacuum-dried at 80° C. for 12 hours or more, and subsequently subjected to injection molding as described above, followed by various evaluations. Results of the various evaluations are given in Table 14.

Comparative Examples 7 and 9 to 11

The required components were mixed in the proportions given in Tables 13 and 15 and processed by melt kneading under a nitrogen flow at a cylinder temperature, screw rotating speed, and extrusion rate as given in Tables 13 and 15 in a complete intermeshing type co-rotating twin screw extruder (TEX-65αII, manufactured by Japan Steel Works, Ltd.) equipped with two double-thread screws with a screw diameter of 65 mm and a L/D ratio of 35, thereby discharging a molten resin strand from the outlet (L/D=35). Screw configuration (III) was adopted. The entire materials were fed from the root of the extruder (a position where L/D=1) (a 3% position assuming that the materials are fed from near the upstream end while molten resin is discharged from near the downstream end and that the upstream end of the screw is located at the 0% position while the downstream end of the screw is located at the 100% position) as specified in Tables 13 and 15. A vent vacuum zone is provided at a position where L/D=30, and the volatile components were removed at a gauge pressure of –0.1 MPa. Subsequently, the molten resin having passed the die head and being discharged from 4 mm diameter×23 holes was pulled to produce a strand and cooled as it passed through a cooling bath, and it was cut by a pelletizer while being taken up, thus providing pellets of a thermoplastic resin composition. The pellets were then vacuum-dried at 80° C. for 12 hours or more, and subsequently subjected to injection molding as described above, followed by various evaluations. The kneading conditions used and various evaluation results obtained are given in Tables 13 to 16.

TABLE 5

| | | | | Example | | | | | |
|---|---|---|---|---|---|---|---|---|---|
| | | | | 1 | 2 | 3 | 4 | 5 | 6 |
| Compounding Ratio | thermoplastic resin-rubbery polymer composite composition (A-B) | Reference Example 2 | parts by weight | 100 | 100 | 100 | 100 | 100 | 100 |
| | inorganic filler (C) | C-1 | parts by weight | 45 | 100 | 45 | 45 | 45 | 45 |
| | dendritic polyester resin (E) | E-1 | parts by weight | 0 | 0 | 1.5 | 5 | 0 | 0 |
| | anhydride (F) | F-1 | parts by weight | 0 | 0 | 0 | 0 | 0.2 | 1 |
| Melt | screw diameter of twin screw extruder | | mm | 65 | 65 | 65 | 65 | 65 | 65 |

TABLE 5-continued

| | | | Example 1 | Example 2 | Example 3 | Example 4 | Example 5 | Example 6 |
|---|---|---|---|---|---|---|---|---|
| kneading | L/D of twin screw extruder | — | 35 | 35 | 35 | 35 | 35 | 35 |
| | screw configuration | — | III | III | III | III | III | III |
| | components fed at root of extruder | — | A-B | A-B | A-B | A-B | A-B | A-B |
| | | | | | E | E | F | F |
| | components fed at midstream of extruder | — | C | C | C | C | C | C |
| | position of midstream feeding of components into extruder | % | 66 | 66 | 66 | 66 | 66 | 66 |
| | elongational flow zone   existent/absent | — | absent | absent | absent | absent | absent | absent |
| | inflow-effect pressure fall | kg/cm² | — | — | — | — | — | — |
| | proportion to overall length | % | — | — | — | — | — | — |
| | size of each elongational flow zone (Lk/D) | — | — | — | — | — | — | — |
| | number of elongational flow zones | number | — | — | — | — | — | — |
| | cylinder temperature setting | °C. | — | — | — | — | — | — |
| | mixing zone   existent/absent | — | absent | absent | absent | absent | absent | absent |
| | proportion to overall length | % | — | — | — | — | — | — |
| | size of each mixing zone (Lm/D) | — | — | — | — | — | — | — |
| | number of mixing zones | number | — | — | — | — | — | — |
| | cylinder temperature setting | °C. | — | — | — | — | — | — |
| | cylinder temperature setting outside elongational flow zones and mixing zones | °C. | 250 | 250 | 250 | 250 | 250 | 250 |
| | screw rotating speed | rpm | 200 | 200 | 200 | 200 | 200 | 200 |
| | extrusion rate | kg/h | 300 | 300 | 300 | 300 | 300 | 300 |
| | discharged resin temperature | °C. | 305 | 300 | 300 | 300 | 300 | 300 |
| | existent/absent of gelled material | — | absent | absent | absent | absent | absent | absent |

TABLE 6

| | | | Example 1 | Example 2 | Example 3 | Example 4 | Example 5 | Example 6 |
|---|---|---|---|---|---|---|---|---|
| Morphology | continuous phase resin | — | A | A | A | A | A | A |
| | dispersed phase resin | — | B | B | B | B | B | B |
| | existent/absent of 1 to 100 nm fine particles in dispersed phase | — | existent | existent | existent | existent | existent | existent |
| | proportion of 1 to 100 nm fine particles in dispersed phase | % | 24 | 24 | 24 | 24 | 24 | 24 |
| distribution of glass fiber in thermoplastic resin composition | weight average fiber length of glass fiber | μm | 355 | 325 | 370 | 385 | 368 | 380 |
| | proportion of glass fiber filaments with 300 μm or less length to entire glass fiber | wt % | 31 | 35 | 28 | 24 | 30 | 26 |
| Molding | cylinder temperature setting | °C. | 250 | 250 | 250 | 250 | 250 | 250 |
| | mold temperature setting | °C. | 80 | 80 | 80 | 80 | 80 | 80 |
| Flowability | flow length | mm | 20 | 10 | 42 | 73 | 35 | 62 |
| General physical properties | tensile strength | ISO527-1, 2  MPa | 110 | 145 | 113 | 112 | 113 | 111 |
| | tensile elongation at break | ISO527-1, 2  % | 7.5 | 6.6 | 7.4 | 6.6 | 7.3 | 6.3 |
| | flexural modulus | ISO178  GPa | 6.6 | 10.0 | 6.6 | 6.7 | 6.6 | 6.7 |
| | Charpy impact strength | ISO179  kJ/m² | 38 | 39 | 37 | 31 | 37 | 30 |
| | deflection temperature under load | ISO75, 0.45 MPa  kJ/m² | 215 | 220 | 215 | 215 | 216 | 215 |
| High speed compression test (as test for shock absorption members) | displacement when load becomes zero | mm | 7.5 | 7.0 | 7.2 | 6.5 | 7.0 | 6.2 |
| | initial load | kN | 17.0 | 22.0 | 17.5 | 17.0 | 17.0 | 17.2 |
| | displacement range included in initial load ±2 kN | mm | 5.8 | 5.2 | 5.5 | 5.3 | 5.5 | 5.0 |

TABLE 7

| | | | | Example 7 | Example 8 | Example 9 | Example 10 | Example 11 | Example 12 | Example 13 |
|---|---|---|---|---|---|---|---|---|---|---|
| Compounding ratio | thermoplastic resin (A) | A-1 | parts by weight | 0 | 0 | 0 | 0 | 0 | 35 | 70 |
| | rubbery polymer having a reactive | B-1 | parts by weight | 0 | 0 | 0 | 0 | 0 | 0 | 30 |
| | | B-3 | parts by weight | 0 | 0 | 0 | 0 | 0 | 15 | 0 |

TABLE 7-continued

| | | | Example | | | | | | |
|---|---|---|---|---|---|---|---|---|---|
| | | | 7 | 8 | 9 | 10 | 11 | 12 | 13 |
| | functional group (B) thermoplastic resin-rubbery polymer composite composition (A-B) | Reference Example 2 | parts by weight | 100 | 100 | 100 | 100 | 100 | 50 | 0 |
| | inorganic filler (C) | C-1 | parts by weight | 45 | 100 | 0 | 0 | 0 | 45 | 45 |
| | | C-2 | parts by weight | 0 | 0 | 20 | 45 | 0 | 0 | 0 |
| | | C-3 | parts by weight | 0 | 0 | 0 | 0 | 45 | 0 | 0 |
| | dendritic polyester resin (E) | E-1 | parts by weight | 1.5 | 1.5 | 0 | 0 | 0 | 0 | 0 |
| | anhydride (F) | F-1 | parts by weight | 0.2 | 0.2 | 0 | 0 | 0 | 0 | 0 |
| | thermal stabilizer (G) | G-1 | parts by weight | 0 | 0 | 0 | 0 | 0 | 0 | 0.2 |
| | | G-2 | parts by weight | 0 | 0 | 0 | 0 | 0 | 0 | 0.2 |
| Melt kneading | screw diameter of twin screw extruder | | mm | 65 | 65 | 65 | 65 | 65 | 65 | 65 |
| | L/D of twin screw extruder | | — | 35 | 35 | 35 | 35 | 35 | 35 | 45 |
| | screw configuration | | — | III | III | III | III | III | III | IV |
| | components fed at root of extruder | | | A-B E F | A-B E F | A-B | A-B | A-B C | A B A-B | A B G |
| | components fed at midstream of extruder | | — | C | C | C | C | — | C | C |
| | position of midstream feeding of components into extruder | | % | 66 | 66 | 66 | 66 | — | 66 | 73 |
| | elongational flow zone | existent/absent | — | absent | absent | absent | absent | absent | absent | existent |
| | | inflow-effect pressure fall | kg/cm² | — | — | — | — | — | — | 150 |
| | | proportion to overall length | % | — | — | — | — | — | — | 9 |
| | | size of each elongational flow zone (Lk/D) | — | — | — | — | — | — | — | 4 |
| | | number of elongational flow zones | number | — | — | — | — | — | — | 1 |
| | | cylinder temperature setting | °C. | — | — | — | — | — | — | 230 |
| | mixing zone | existent/absent | — | absent | absent | absent | absent | absent | absent | existent |
| | | proportion to overall length | % | — | — | — | — | — | — | 18 |
| | | size of each mixing zone (Lm/D) | — | — | — | — | — | — | — | 4 |
| | | number of mixing zones | number | — | — | — | — | — | — | 2 |
| | | cylinder temperature setting | °C. | — | — | — | — | — | — | 230 |

TABLE 8

| | | | | Example | | | | | | |
|---|---|---|---|---|---|---|---|---|---|---|
| | | | | 7 | 8 | 9 | 10 | 11 | 12 | 13 |
| Melt kneading | cylinder temperature setting outside elongational flow zones and mixing zones | | °C. | 250 | 250 | 250 | 250 | 250 | 250 | 240 |
| | screw rotating speed | | Rpm | 200 | 200 | 200 | 200 | 200 | 200 | 350 |
| | extrusion rate | | kg/h | 300 | 300 | 300 | 300 | 300 | 300 | 200 |
| | discharged resin temperature | | °C. | 290 | 300 | 305 | 328 | 290 | 295 | 325 |
| | existent/absent of gelled material | | — | absent | absent | absent | absent | absent | absent | absent |
| Morphology | continuous phase resin | | — | A | A | A | A | A | A | A |
| | dispersed phase resin | | — | B | B | B | B | B | B | B |
| | existent/absent of 1 to 100 nm fine particles in dispersed phase | | — | existent | existent | existent | existent | existent | existent | existent |
| | proportion of 1 to 100 nm fine particles in dispersed phase | | % | 24 | 24 | 24 | 24 | 24 | 20 | 25 |
| distribution of glass fiber in thermoplastic resin composition | weight average fiber length of glass fiber | | Mm | 370 | 340 | — | — | — | 365 | 360 |
| | proportion of glass fiber filaments with 300 μm or less length to entire glass fiber | | wt % | 30 | 33 | — | — | — | 32 | 30 |
| Molding | cylinder temperature setting | | °C. | 250 | 250 | 250 | 250 | 250 | 250 | 250 |
| | mold temperature setting | | °C. | 80 | 80 | 80 | 80 | 80 | 80 | 80 |
| Flowability | flow length | | Mm | 60 | 23 | 35 | 12 | 45 | 40 | 30 |
| General physical Properties | tensile strength | ISO527-1, 2 | MPa | 116 | 150 | 108 | 130 | 62 | 103 | 113 |
| | tensile elongation at break | ISO527-1, 2 | % | 7.2 | 6.5 | 8.7 | 6.0 | 26.0 | 7.7 | 7.5 |
| | flexural modulus | ISO178 | GPa | 6.7 | 10.2 | 8.0 | 13.0 | 4.2 | 6.0 | 6.5 |
| | Charpy impact strength | ISO179 | kJ/m² | 35 | 37 | 40 | 20 | 63 | 37 | 37 |

TABLE 8-continued

|  |  |  |  | Example | | | | | | |
|---|---|---|---|---|---|---|---|---|---|---|
|  |  |  |  | 7 | 8 | 9 | 10 | 11 | 12 | 13 |
|  | deflection temperature under load | ISO75, 0.45 MPa | kJ/m² | 215 | 221 | 205 | 219 | 170 | 210 | 215 |
| High speed compression test (as test for shock absorption members) | displacement when load becomes zero | | Mm | 7.7 | 7.0 | 8.0 | 6.2 | >10 | 7.8 | 7.5 |
|  | initial load | | kN | 18.0 | 22.3 | 20.0 | 23.0 | 13.0 | 16.5 | 17.2 |
|  | displacement range included in initial load ±2 kN | | Mm | 6.0 | 5.3 | 5.0 | 4.5 | 4.2 | 5.2 | 5.5 |

TABLE 9

|  |  |  |  | Example | | | | | | | | |
|---|---|---|---|---|---|---|---|---|---|---|---|---|
|  |  |  |  | 1 | 14 | 15 | 16 | 17 | 18 | 19 | 20 | 21 |
| Compounding ratio | thermoplastic resin-rubbery polymer composite composition (A-B) | Reference Example 2 | parts by weight | 100 | 0 | 0 | 0 | 0 | 0 | 0 | 0 | 0 |
|  |  | Reference Example 3 | parts by weight | 0 | 100 | 0 | 0 | 0 | 0 | 0 | 0 | 0 |
|  |  | Reference Example 4 | parts by weight | 0 | 0 | 100 | 0 | 0 | 0 | 0 | 0 | 0 |
|  |  | Reference Example 5 | parts by weight | 0 | 0 | 0 | 100 | 0 | 0 | 0 | 0 | 0 |
|  |  | Reference Example 6 | parts by weight | 0 | 0 | 0 | 0 | 100 | 0 | 0 | 0 | 0 |
|  |  | Reference Example 7 | parts by weight | 0 | 0 | 0 | 0 | 0 | 100 | 0 | 0 | 0 |
|  |  | Reference Example 8 | parts by weight | 0 | 0 | 0 | 0 | 0 | 0 | 100 | 0 | 0 |
|  |  | Reference Example 9 | parts by weight | 0 | 0 | 0 | 0 | 0 | 0 | 0 | 100 | 0 |
|  |  | Reference Example 10 | parts by weight | 0 | 0 | 0 | 0 | 0 | 0 | 0 | 0 | 100 |
|  | inorganic filler (C) | C-1 | parts by weight | 45 | 45 | 45 | 45 | 45 | 0 | 0 | 45 | 45 |
|  |  | C-4 | parts by weight | 0 | 0 | 0 | 0 | 0 | 45 | 45 | 0 | 0 |
| Melt kneading | screw diameter of twin screw extruder | | mm | 65 | 65 | 65 | 65 | 65 | 65 | 65 | 65 | 65 |
|  | L/D of twin screw extruder | | — | 35 | 35 | 35 | 35 | 35 | 35 | 35 | 35 | 35 |
|  | screw configuration | | — | III | III | III | III | III | III | III | III | III |
|  | components fed at root of extruder | | — | A-B | A-B | A-B | A-B | A-B | A-B | A-B | A-B | A-B |
|  | components fed at midstream of extruder | | — | C | C | C | C | C | C | C | C | C |
|  | position of midstream feeding of components into extruder | | % | 66 | 66 | 66 | 66 | 66 | 66 | 66 | 66 | 66 |
|  | elongational flow zone | existent/absent | — | absent | absent | absent | absent | absent | absent | absent | absent | absent |
|  | mixing zone | existent/absent | — | absent | absent | absent | absent | absent | absent | absent | absent | absent |
|  | cylinder temperature setting outside elongational flow zones and mixing zones | | °C. | 250 | 250 | 250 | 250 | 250 | 280 | 250 | 220 | 220 |
|  | screw rotating speed | | rpm | 200 | 200 | 200 | 200 | 200 | 200 | 200 | 200 | 200 |
|  | extrusion rate | | kg/h | 300 | 300 | 300 | 300 | 300 | 300 | 300 | 300 | 300 |
|  | discharged resin temperature | | °C. | 305 | 290 | 320 | 307 | 310 | 324 | 286 | 260 | 255 |
|  | existent/absent of gelled material | | — | absent | absent | absent | absent | absent | absent | absent | absent | absent |

TABLE 10

|  |  |  | Example | | | | | | | | |
|---|---|---|---|---|---|---|---|---|---|---|---|
|  |  |  | 1 | 14 | 15 | 16 | 17 | 18 | 19 | 20 | 21 |
| Morphology | continuous phase resin | — | A | A | A | A | A | A | A | A | A |
|  | dispersed phase resin | — | B | B | B | B | B | B | B | B | B |
|  | existent/absent of 1 to 100 nm fine particles in dispersed phase | — | existent | existent | existent | existent | existent | existent | existent | existent | existent |
|  | proportion of 1 to 100 nm fine particles in dispersed phase | % | 24 | 24 | 24 | 24 | 23 | 23 | 22 | 22 | 23 |

TABLE 10-continued

| | | | Example | | | | | | | | |
|---|---|---|---|---|---|---|---|---|---|---|---|
| | | | 1 | 14 | 15 | 16 | 17 | 18 | 19 | 20 | 21 |
| distribution of glass fiber in thermoplastic resin composition | weight average fiber length of glass fiber | μm | 355 | 380 | 330 | 350 | 360 | 340 | 358 | 375 | 380 |
| | proportion of glass fiber filaments with 300 μm or less length to entire glass fiber | wt % | 31 | 24 | 38 | 33 | 27 | 33 | 28 | 26 | 25 |
| Molding | cylinder temperature setting | °C. | 250 | 250 | 250 | 250 | 250 | 290 | 250 | 215 | 205 |
| | mold temperature setting | °C. | 80 | 80 | 80 | 80 | 80 | 80 | 80 | 80 | 80 |
| Flowability | flow length | mm | 20 | 32 | 12 | 15 | 12 | 12 | 20 | 24 | 26 |
| General physical properties | tensile strength | ISO527-1, 2 | MPa | 110 | 130 | 95 | 106 | 100 | 120 | 101 | 85 | 82 |
| | tensile elongation at break | ISO527-1, 2 | % | 7.5 | 6.8 | 6.9 | 8.2 | 9.0 | 7.0 | 7.3 | 7.0 | 8.0 |
| | flexural modulus | ISO178 | GPa | 6.6 | 7.1 | 6.0 | 6.4 | 6.1 | 6.9 | 6.2 | 5.0 | 4.9 |
| | Charpy impact strength | ISO179 | kJ/m² | 38 | 31 | 32 | 40 | 43 | 35 | 35 | 34 | 36 |
| | deflection temperature under load | ISO75, 0.45 MPa | kJ/m² | 215 | 218 | 210 | 215 | 210 | 245 | 212 | 165 | 160 |
| High speed compression test (as test for shock absorption members) | displacement when load becomes zero | mm | 7.5 | 6.7 | 6.5 | 8.5 | 9.0 | 7.0 | 7.5 | 6.5 | 7.0 |
| | initial load | kN | 17.0 | 19.0 | 13.0 | 16.5 | 15.5 | 17.5 | 16.0 | 14.0 | 13.6 |
| | displacement range included in initial load ±2 kN | mm | 5.8 | 5.0 | 5.3 | 6.1 | 6.3 | 6.0 | 5.6 | 5.0 | 5.3 |

TABLE 11

| | | | | Example | | | | | | | |
|---|---|---|---|---|---|---|---|---|---|---|---|
| | | | | 22 | 23 | 24 | 25 | 26 | 27 | 28 | 29 |
| Compounding ratio | thermoplastic resin-rubbery polymer composite composition (A-B) | Reference Example 11 | parts by weight | 100 | 0 | 0 | 0 | 0 | 0 | 0 | 0 |
| | | Reference Example 12 | parts by weight | 0 | 100 | 0 | 0 | 0 | 0 | 0 | 0 |
| | | Reference Example 13 | parts by weight | 0 | 0 | 100 | 0 | 0 | 0 | 0 | 0 |
| | | Reference Example 14 | parts by weight | 0 | 0 | 0 | 100 | 0 | 0 | 0 | 0 |
| | | Reference Example 15 | parts by weight | 0 | 0 | 0 | 0 | 100 | 0 | 0 | 0 |
| | | Reference Example 16 | parts by weight | 0 | 0 | 0 | 0 | 0 | 100 | 0 | 0 |
| | | Reference Example 17 | parts by weight | 0 | 0 | 0 | 0 | 0 | 0 | 100 | 0 |
| | | Reference Example 18 | parts by weight | 0 | 0 | 0 | 0 | 0 | 0 | 0 | 100 |
| | inorganic filler (C) | C-4 | parts by weight | 45 | 0 | 0 | 0 | 0 | 0 | 0 | 0 |
| | | C-5 | parts by weight | 0 | 45 | 45 | 45 | 45 | 45 | 0 | 0 |
| | | C-6 | parts by weight | 0 | 0 | 0 | 0 | 0 | 0 | 45 | 0 |
| | | C-7 | parts by weight | 0 | 0 | 0 | 0 | 0 | 0 | 0 | 45 |
| Melt kneading | screw diameter of twin screw extruder | | Mm | 65 | 65 | 65 | 65 | 65 | 65 | 65 | 65 |
| | L/D of twin screw extruder | | — | 35 | 35 | 35 | 35 | 35 | 35 | 35 | 35 |
| | screw configuration | | — | III | III | III | III | III | III | III | III |
| | components fed at root of extruder | | — | A-B | A-B | A-B | A-B | A-B | A-B | A-B | A-B |
| | components fed at midstream of extruder | | — | C | C | C | C | C | C | C | C |
| | position of midstream feeding of components into extruder | | % | 66 | 66 | 66 | 66 | 66 | 66 | 66 | 66 |
| | elongational flow zone existent/absent | | — | absent | absent | absent | absent | absent | absent | absent | absent |
| | mixing zone existent/absent | | — | absent | absent | absent | absent | absent | absent | absent | absent |
| | cylinder temperature setting outside elongational flow zones and mixing zones | | °C. | 290 | 250 | 280 | 260 | 210 | 290 | 290 | 210 |
| | screw rotating speed | | Rpm | 200 | 200 | 200 | 200 | 200 | 200 | 200 | 200 |
| | extrusion rate | | kg/h | 300 | 300 | 300 | 300 | 300 | 300 | 300 | 300 |
| | discharged resin temperature | | °C. | 330 | 290 | 305 | 292 | 243 | 331 | 328 | 245 |
| | existent/absent of gelled material | | — | absent | absent | absent | absent | absent | absent | absent | absent |

TABLE 12

| | | | Example | | | | | | | |
|---|---|---|---|---|---|---|---|---|---|---|
| | | | 22 | 23 | 24 | 25 | 26 | 27 | 28 | 29 |
| Morphology | continuous phase resin | — | A | A | A | A | A | A | A | A |
| | dispersed phase resin | — | B | B | B | B | B | B | B | B |
| | existent/absent of 1 to 100 nm fine particles in dispersed phase | — | existent | existent | existent | existent | existent | existent | existent | existent |
| | proportion of 1 to 100 nm fine particles in dispersed phase | % | 22 | 16 | 16 | 14 | 15 | 17 | 21 | 15 |

TABLE 12-continued

|  |  |  | Example | | | | | | | |
|---|---|---|---|---|---|---|---|---|---|---|
|  |  |  | 22 | 23 | 24 | 25 | 26 | 27 | 28 | 29 |
| distribution of glass fiber in thermoplastic resin composition | weight average fiber length of glass fiber | μm | 333 | 374 | 380 | 390 | 388 | 310 | 360 | 380 |
|  | proportion of glass fiber filaments with 300 μm or less length to entire glass fiber | wt % | 37 | 25 | 25 | 23 | 21 | 38 | 30 | 23 |
| Molding | cylinder temperature setting | ° C. | 320 | 250 | 290 | 250 | 195 | 320 | 305 | 185 |
|  | mold temperature setting | ° C. | 130 | 80 | 130 | 80 | 80 | 130 | 130 | 40 |
| Flowability | flow length | mm | 15 | 23 | 27 | 30 | 32 | 12 | 22 | 36 |
| General physical properties | tensile strength ISO527-1, 2 | MPa | 123 | 100 | 88 | 98 | 99 | 97 | 108 | 80 |
|  | tensile elongation at break ISO527-1, 2 | % | 6.7 | 6.5 | 6.2 | 6.0 | 6.5 | 5.7 | 7.0 | 6.6 |
|  | flexural modulus ISO178 | GPa | 7.0 | 6.3 | 6.0 | 6.4 | 6.9 | 5.9 | 6.6 | 4.9 |
|  | Charpy impact strength ISO179 | kJ/m$^2$ | 30 | 30 | 29 | 26 | 29 | 24 | 34 | 31 |
|  | deflection temperature under load ISO75, 0.45 MPa | kJ/m$^2$ | 270 | 208 | 190 | 150 | 150 | 220 | 265 | 155 |
| High speed compression test (as test for shock absorption members) | displacement when load becomes zero | mm | 6.2 | 6.3 | 6.1 | 6.5 | 6.5 | 6.1 | 7.3 | 6.4 |
|  | initial load | kN | 19.0 | 15.0 | 13.0 | 14.6 | 15.3 | 15.0 | 16.8 | 13.0 |
|  | displacement range included in initial load ±2 kN | mm | 4.7 | 4.5 | 4.2 | 4.6 | 4.8 | 4.1 | 5.7 | 4.9 |

TABLE 13

|  |  |  |  | Comparative Example | | | | | | | |
|---|---|---|---|---|---|---|---|---|---|---|---|
|  |  |  |  | 1 | 2 | 3 | 4 | 5 | 6 | 7 | 8 |
| Compounding ratio | thermoplastic resin (A) | A-1 | parts by weight | 100 | 0 | 0 | 0 | 0 | 70 | 70 | 70 |
|  | rubbery polymer having a reactive functional group (B) | B-1 | parts by weight | 0 | 0 | 0 | 0 | 0 | 30 | 30 | 30 |
|  | thermoplastic resin-rubbery polymer | Reference Example 2 | parts by weight | 0 | 100 | 100 | 100 | 0 | 0 | 0 | 0 |
|  | composite composition (A-B) | Reference Example 19 | parts by weight | 0 | 0 | 0 | 0 | 100 | 0 | 0 | 0 |
|  | inorganic filler (C) | C-1 | parts by weight | 0 | 0 | 0.4 | 230 | 45 | 45 | 0 | 0 |
|  |  | C-3 | parts by weight | 0 | 0 | 0 | 0 | 0 | 0 | 45 | 45 |
|  | thermal stabilizer (G) | G-1 | parts by weight | 0 | 0 | 0 | 0 | 0 | 0.2 | 0.2 | 0.2 |
|  |  | G-2 | parts by weight | 0 | 0 | 0 | 0 | 0 | 0.2 | 0.2 | 0.2 |
| Melt kneading | screw diameter of twin screw extruder | mm | | — | — | 65 | 65 | 65 | 65 | 65 | 65 |
|  | L/D of twin screw extruder | | — | — | — | 35 | 35 | 35 | 35 | 35 | 35 |
|  | screw configuration | | — | — | — | III | III | III | III | III | III |
|  | components fed at root of extruder | | | — | — | A-B | A-B | A-B | A B G | A B C | A C G |
|  | components fed at midstream of extruder | | — | — | — | C | C | C | C | — | B |
|  | position of midstream feeding of components into extruder | % | | — | — | 66 | 66 | 66 | 66 | — | 66 |
|  | elongationa flow zone | existent/absent | — | — | — | absent | absent | absent | absent | absent | absent |
|  | mixing zone | existent/absent | — | — | — | absent | absent | absent | absent | absent | absent |
|  | cylinder temperature setting outside elongational flow zones and mixing zones | ° C. | | — | — | 250 | 250 | 250 | 250 | 250 | 250 |
|  | screw rotating speed | rpm | | — | — | 200 | 200 | 200 | 200 | 200 | 200 |
|  | extrusion rate | kg/h | | — | — | 300 | 300 | 300 | 300 | 300 | 300 |
|  | discharged resin temperature | ° C. | | — | — | 292 | 345 | 280 | 280 | 275 | 271 |
|  | existent/absent of gelled material | — | | — | — | absent | absent | absent | absent | absent | absent |

TABLE 14

| | | | | Comparative Example | | | | | | | |
|---|---|---|---|---|---|---|---|---|---|---|---|
| | | | | 1 | 2 | 3 | 4 | 5 | 6 | 7 | 8 |
| Morphology | continuous phase resin | | | — | — | A | A | A | A | A | A |
| | dispersed phase resin | | | — | — | B | B | B | B | B | B |
| | existent/absent of 1 to 100 nm fine particles in dispersed phase | | | — | — | existent | existent | existent | existent | existent | existent |
| | proportion of 1 to 100 nm fine particles in dispersed phase | | % | — | 24 | 24 | 24 | 7 | 5 | 5 | 3 |
| distribution of glass fiber in thermoplastic resin composition | weight average fiber length of glass fiber | | μm | — | — | 450 | — | 388 | 393 | — | — |
| | proportion of glass fiber filaments with 300 μm or less length to entire glass fiber | | wt % | — | — | 13 | — | 23 | 22 | — | — |
| Molding | cylinder temperature setting | | °C. | 250 | 250 | 250 | 250 | 250 | 250 | 250 | 250 |
| | mold temperature setting | | °C. | 80 | 80 | 80 | 80 | 80 | 80 | 80 | 80 |
| Flowability | flow length | | mm | 130 | 37 | 32 | molding impossible | 45 | 50 | 65 | 75 |
| General physical properties | tensile strength | ISO527-1, 2 | MPa | 78 | 43 | 46 | — | 115 | 117 | 56 | 60 |
| | tensile elongation at break | ISO527-1, 2 | % | 50.0 | >200 | 60.0 | — | 4.2 | 4.0 | 6.0 | 12.0 |
| | flexural modulus | ISO178 | GPa | 2.8 | 1.5 | 1.6 | — | 6.6 | 6.6 | 2.5 | 4.0 |
| | Charpy impact strength | ISO179 | kJ/m² | 5 | 107 | 80 | — | 25 | 24 | 20 | 50 |
| | deflection temperature under load | ISO75, 0.45 MPa | kJ/m² | 150 | 85 | 105 | — | 215 | 215 | 150 | 170 |
| High speed compression test (as test for shock absorption members) | displacement when load becomes zero | | mm | 7.0 | >10 | >10 | — | 4.7 | 4.5 | 4.7 | 5.7 |
| | initial load | | kN | 24.0 | 9.5 | 10.0 | — | 17.0 | 17.2 | 12.0 | 12.0 |
| | displacement range included in initial load ±2 kN | | mm | <2 | <2 | <2 | — | 3.3 | 3.4 | <2 | 3.0 |

TABLE 15

| | | | | Comparative Example | | | | |
|---|---|---|---|---|---|---|---|---|
| | | | | 9 | 10 | 11 | 12 | 13 |
| Compounding Ratio | thermoplastic resin (A) | A-1 | parts by weight | 0 | 0 | 0 | 50 | 50 |
| | thermoplastic resin-rubbery polymer composite composition (A-B) | Reference Example 2 | parts by weight | 100 | 100 | 100 | 50 | 50 |
| | inorganic filler (C) | C-1 | parts by weight | 45 | 45 | 45 | 45 | 5 |
| | dendritic polyester resin (E) | E-1 | parts by weight | 0 | 1.5 | 1.5 | 0 | 0 |
| | anhydride (F) | F-1 | parts by weight | 0 | 0 | 0.2 | 0 | 0 |
| Melt kneading | screw diameter of twin screw extruder | | mm | 65 | 65 | 65 | 65 | 65 |
| | L/D of twin screw extruder | | — | 35 | 35 | 35 | 35 | 35 |
| | screw configuration | | — | III | III | III | III | III |
| | components fed at root of extruder | | | A-B C | A-B C E | A-B C E F | A A-B | A A-B |
| | components fed at midstream of extruder | | — | — | — | — | C | C |
| | position of midstream feeding of components into extruder | | % | — | — | — | 66 | 66 |
| | elongational flow zone | existent/absent | — | absent | absent | absent | absent | absent |
| | mixing zone | existent/absent | — | absent | absent | absent | absent | absent |
| | cylinder temperature setting outside elongational flow zones and mixing zones | | °C. | 250 | 250 | 250 | 250 | 250 |
| | screw rotating speed | | rpm | 200 | 200 | 200 | 200 | 200 |
| | extrusion rate | | kg/h | 300 | 300 | 300 | 300 | 300 |
| | discharged resin temperature | | °C. | 335 | 330 | 322 | 293 | 286 |
| | existent/absent of gelled material | | — | absent | absent | absent | absent | absent |

TABLE 16

| | | | | Comparative Example | | | | |
|---|---|---|---|---|---|---|---|---|
| | | | | 9 | 10 | 11 | 12 | 13 |
| Morphology | continuous phase resin | | — | A | A | A | A | A |
| | dispersed phase resin | | — | B | B | B | B | B |
| | existent/absent of 1 to 100 nm fine particles in dispersed phase | | — | existent | existent | existent | existent | existent |
| | proportion of 1 to 100 nm fine particles in dispersed phase | | % | 24 | 24 | 24 | 24 | 24 |

TABLE 16-continued

|  |  |  | Comparative Example | | | | |
|---|---|---|---|---|---|---|---|
|  |  |  | 9 | 10 | 11 | 12 | 13 |
| distribution of glass fiber in thermoplastic resin composition | weight average fiber length of glass fiber | μm | 220 | 230 | 250 | 405 | 420 |
|  | proportion of glass fiber filaments of 300 μm or less length to entire glass fiber | wt % | 60 | 55 | 51 | 18 | 15 |
| Molding | cylinder temperature setting | °C. | 250 | 250 | 250 | 250 | 250 |
|  | mold temperature setting | °C. | 80 | 80 | 80 | 80 | 80 |
| Flowability | flow length | mm | 22 | 44 | 65 | 38 | 48 |
| General physical properties | tensile strength | ISO527-1, 2 MPa | 95 | 98 | 100 | 146 | 60 |
|  | tensile elongation at break | ISO527-1, 2 % | 5.5 | 5.8 | 6.0 | 5.0 | 13.0 |
|  | flexural modulus | ISO178 GPa | 6.0 | 6.0 | 6.0 | 7.4 | 2.2 |
|  | Charpy impact strength | ISO179 kJ/m$^2$ | 28 | 29 | 30 | 25 | 27 |
|  | deflection temperature under load | ISO75, 0.45 MPa kJ/m$^2$ | 210 | 210 | 210 | 214 | 150 |
| High speed compression test (as test for shock absorption members) | displacement when load becomes zero | mm | 7.4 | 7.2 | 7.0 | 4.4 | 6.3 |
|  | initial load | kN | 11.0 | 11.5 | 11.6 | 23.0 | 11.0 |
|  | displacement range included in initial load ±2 kN | mm | 3.7 | 3.7 | 3.7 | 2.5 | 2.3 |

In Examples 1 to 12 and 14 to 29, thermoplastic resin compositions were produced by adding components such as inorganic filler to the thermoplastic resin-rubbery polymer composite compositions (A-B) prepared in Reference Examples. The dispersed phase (B) of a rubbery polymer having a reactive functional group (B) successfully contains fine particles with a particle diameter of 1 to 100 nm formed of a compound resulting from a reaction between the thermoplastic resin (A) and the rubbery polymer having a reactive functional group (B), with the area occupied by the fine particles accounting for 10% or more of the area of the dispersed phase (B). In the thermoplastic resin compositions prepared by adding glass fiber as an inorganic filler in Examples 1 to 8, 12, and 14 to 29, the glass fiber in the thermoplastic resin composition has a weight-average fiber length in the range of 300 to 400 μm, and the glass fiber filaments with a length of 300 μm or less account for 20 to 40 wt % of the entire glass fiber. Results of the high speed compression test for a square prism specimen prepared by molding such a thermoplastic resin composition show a displacement when load becomes zero of 6 mm or more, an initial load of 12 to 30 kN, and a displacement range included in initial load ±2 kN of 4 mm or more, suggesting that square prism shaped moldings can give a high-load square wave. Thus, the use of this thermoplastic resin composition makes it possible to design shock absorbing members in simple shapes.

In Example 13, thermoplastic resin-rubbery polymer composite composition (A-B) is produced in the upstream (front) region of the extruder and inorganic filler (C) is added subsequently. The melt-kneading process in the upstream region is controlled elaborately to promote the reaction between the thermoplastic resin (A) and the rubbery polymer having a reactive functional group (B) to produce, prior to the addition of the inorganic filler (C), a thermoplastic resin-rubbery polymer composite composition (A-B) in which the dispersed phase (B) contains fine particles with a particle diameter of 1 to 100 nm formed of a compound resulting from the reaction between the thermoplastic resin (A) and the rubbery polymer having a reactive functional group (B), with the area occupied by the fine particles accounting for 10% or more of the area of the dispersed phase (B). The existence of these fine particles was confirmed by examining a sample taken through a sampling valve provided at a position where L/D=30 in the extruder. Accordingly, in the resulting thermoplastic resin composition as well, the dispersed phase (B) of a rubbery polymer having a reactive functional group (B) successfully contains fine particles with a particle diameter of 1 to 100 nm formed of a compound resulting from the reaction between the thermoplastic resin (A) and the rubbery polymer having a reactive functional group (B), with the area occupied by the fine particles accounting for 10% or more of the area of the dispersed phase (B). Furthermore, the glass fiber in the thermoplastic resin composition has a weight-average fiber length in the range of 300 to 400 μm, and the glass fiber filaments with a length of 300 μm or less account for 20 to 40 wt % of the entire glass fiber. Results of the high speed compression test for a square prism specimen prepared by molding such a thermoplastic resin composition show a displacement when load becomes zero of 7.5 mm, an initial load of 17.2 kN, and a displacement range included in initial load ±2 kN of 5.5 mm, suggesting that moldings of a square prism shape can give a high-load square wave. Thus, the use of this thermoplastic resin composition makes it possible to design shock absorbing members in simple shapes.

In Comparative Examples 1 and 2 in which no inorganic filler is used, results of the high speed compression test for square prism specimens suggest that although the displacement when load becomes zero is large, the displacement range included in initial load ±2 kN is small (less likely to give a square wave). In Comparative Example 2, the initial load is low.

In Comparative Example 3, a thermoplastic resin composition was produced by adding components such as inorganic filler to the thermoplastic resin-rubbery polymer composite composition (A-B) prepared in Reference Example 2. However, the inorganic filler accounted for only less than 1 part by weight, and accordingly, although the displacement when load becomes zero was large, the initial load was small and the displacement range included in initial load ±2 kN was also small (less likely to give a square wave).

In Comparative Example 4, a thermoplastic resin composition was produced by adding components such as inorganic filler to the thermoplastic resin-rubbery polymer composite compositions (A-B) prepared in Reference Example 2. The inorganic filler accounted for as large as more than 200 parts by weight, and accordingly, it was impossible to perform injection molding.

In Comparative Example 5, a thermoplastic resin composition was produced by adding components such as inorganic filler to the thermoplastic resin-rubbery polymer composite composition (A-B) prepared in Reference Example 19. A thermoplastic resin-rubbery polymer composite composition (A-B) in which the area occupied by the fine particles accounts for only less than 10% is use and, accordingly, fine particles also account for only less than 10% of the dispersed phase (B) in the resulting thermoplastic resin composition. The thermoplastic resin-rubbery polymer composite composition (A-B) have the relation E(V1)<E(V2) where E(V1) and E(V2) represent the tensile modulus at tension speeds V1 and V2, respectively, and where V1<V2. The relation ϵ(V1)>ϵ(V2) is met where ϵ(V1) and ϵ(V2) represent the tensile elongation at break at tension speeds V1 and V2, respectively, and where V1<V2. Accordingly, results of the high speed compression test for square prism specimens show that both the displacement when load becomes zero and the displacement range included in initial load ±2 kN are small.

In Comparative Example 6, as in Example 13, an inorganic filler (C) is added after producing a thermoplastic resin-rubbery polymer composite composition (A-B) in the upstream (front) region of the extruder, but since the melt kneading process in Comparative Example 6 is not controlled so elaborately as in Example 13, the reaction between the thermoplastic resin (A) and the rubbery polymer having a reactive functional group (B) does not progress adequately, resulting in a small proportion of fine particles in the dispersed phase (B) of the rubbery polymer having a reactive functional group. Accordingly, results of the high speed compression test for square prism specimens show that both the displacement when load becomes zero and the displacement range included in initial load ±2 kN are small.

In Comparative Examples 7 and 8 as well, since the melt kneading process is not controlled elaborately, the reaction between thermoplastic resin (A) and rubbery polymer having a reactive functional group (B) does not progress adequately, resulting in a small proportion of fine particles in the dispersed phase (B). Compared to Example 11, therefore, results of the high speed compression test for square prism specimens show that both the displacement when load becomes zero and the displacement range included in initial load ±2 kN are small.

In Comparative Examples 9 to 11, a thermoplastic resin composition was produced by adding components such as inorganic filler (C) to the thermoplastic resin-rubbery polymer composite composition (A-B) prepared in Reference Example 2. Since the inorganic filler is fed at the root of the extruder, the glass fiber in the thermoplastic resin composition has a weight-average fiber length of less than 300 μm, and the glass fiber filaments with a length of 300 μm or less account for more than 40 wt % of the entire glass fiber. Accordingly, results of the high speed compression test for square prism specimens show that both the initial load and the displacement range included in initial load ±2 kN are small.

In Comparative Examples 12 and 13, a thermoplastic resin composition was produced by compounding the thermoplastic resin-rubbery polymer composite composition (A-B) prepared in Reference Example 2, the thermoplastic resin (A) and the inorganic filler (C). Since rubbery polymer (B) accounts for only a small portion of the thermoplastic resin composition, results of the high speed compression test for square prism specimens show that both the displacement when load becomes zero and the displacement range included in initial load ±2 kN are small.

The invention claimed is:

1. A thermoplastic resin composition for shock absorbing members comprising 1 to 200 parts by weight of an inorganic filler (C) blended with 50 to 80 parts by weight of a thermoplastic resin (A) and 20 to 50 parts by weight of a rubbery polymer having a reactive functional group (B) which together account for 100 parts by weight;

having morphological features observed by electron microscopy such that:

the thermoplastic resin (A) and the rubbery polymer having a reactive functional group (B), form a continuous phase and a dispersed phase, respectively, while the inorganic filler (C) are dispersed in the continuous phase and/or the dispersed phase; and the dispersed phase (B) of the rubbery polymer having a reactive functional group (B) contains fine particles with a particle diameter of 1 to 100 nm of a compound resulting from a reaction between the thermoplastic resin (A) and the rubbery polymer having a reactive functional group (B); and an area occupied by the fine particles account for 10% or more of the dispersed phase (B); and a load-displacement curve meeting all of (I), (II) and (III) listed below when a square prism specimen with a cross section of 12.7 mm×12.7 mm and a height of 25.4 mm prepared by injection-molding the thermoplastic resin composition in a parallel direction to its height is subjected to a compression test in which a weight with a mass of 26 kg is allowed to fall freely onto the square prism specimen from a height of 0.5 m:

(I) the displacement when load becomes zero is 6 mm or more, (II) the initial load is 12 kN or more and 30 kN or less, and (III) the displacement range included in initial load ±2 kN is 4 mm or more.

2. The composition as described in claim 1 further comprising 0.1 to 30 parts by weight of a dendritic polyester resin (E) per a total of 100 parts by weight of the thermoplastic resin (A) and the rubbery polymer having a reactive functional group (B) combined, wherein the dendritic polyester resin (E) contains at least one structural unit selected from the group consisting of aromatic oxycarbonyl unit (S), aromatic and/or aliphatic dioxy unit (T), and aromatic dicarbonyl unit (U), along with tri- or higher functional organic residue (D), the organic residue (D) accounting for 7.5 to 50 mol % relative to the total quantity of the monomers that constitute the dendritic polyester.

3. The composition as described in claim 1, wherein the thermoplastic resin (A) is at least one selected from the group consisting of polyamide resin, polyester resin, polyphenylene sulfide resin, polyphenylene oxide resin, polycarbonate resin, polylactic acid resin, and polypropylene resin.

4. The composition as described in claim 1, wherein the thermoplastic resin (A) is polyamide resin.

5. The composition as described in claim 4, wherein 0.01 to 3 parts by weight of an acid anhydride (F) is added per a total of 100 parts by weight of the thermoplastic resin (A) and the rubbery polymer having a reactive functional group (B) combined.

6. The composition as described in claim 5, wherein the acid anhydride (F) is succinic anhydride and/or phthalic anhydride.

7. The composition as described in claim 1, wherein the reactive functional group in the rubbery polymer having a reactive functional group (B) is at least one selected from the group consisting of epoxy group, acid anhydride group, amino group, carboxyl group, carboxyl metal salt, and oxazoline group.

8. The composition as described in claim 1, wherein the inorganic filler (C) is glass fiber.

9. The composition as described in claim 8, wherein the glass fiber in the thermoplastic resin composition has a weight-average fiber length of 300 to 400 μm and the glass fiber filaments with a length of 300 μm or less account for 20 to 40 wt % of the entire glass fiber.

10. A process of manufacturing the composition as described in claim 1, comprising:
blending a thermoplastic resin (A) and a rubbery polymer having a reactive functional group (B) to produce a thermoplastic resin-rubbery polymer composite composition (A-B) having morphological features such that:
the thermoplastic resin (A) and the rubbery polymer having a reactive functional group (B) form a continuous phase and a dispersed phase, respectively;
the dispersed phase (B) formed by the rubbery polymer having a reactive functional group (B) contains fine particles with a diameter of 1 to 100 nm of a compound resulting from a reaction between the thermoplastic resin (A) and the rubbery polymer having a reactive functional group (B); and
the area occupied by the fine particles accounts for 10% or more of the entire dispersed phase (B); and
subsequently adding an inorganic filler (C) and other required components.

11. A process of manufacturing a thermoplastic the composition as described in claim 10, comprising:
providing a twin screw extruder, and
adding an inorganic filler (C) at a position of 50% or more and 80% or less assuming that the materials are fed from near an upstream end while a molten resin composition is discharged from near a downstream end and that the upstream end of the screw is located at a 0% position while the downstream end of the screw is located at a 100% position.

12. A process of manufacturing the composition as described in claim 1, comprising:
blending a thermoplastic resin (A) and a rubbery polymer having a reactive functional group (B) to form a thermoplastic resin-rubbery polymer composite composition (A-B) meeting the relation $E(V1)>E(V2)$ where $E(V1)$ and $E(V2)$ represent the tensile modulus at tension speeds V1 and V2, respectively, and where $V1<V2$; and
subsequently adding an inorganic filler (C).

13. A process of manufacturing the composition as described in claim 1, comprising:
blending a thermoplastic resin (A) and a rubbery polymer having a reactive functional group (B) to form a thermoplastic resin-rubbery polymer composite composition (A-B) meeting the relation $\epsilon(V1)<\epsilon(V2)$ where $\epsilon(V1)$ and $\epsilon(V2)$ represent the tensile elongation at break at tension speeds V1 and V2, respectively, and where $V1<V2$; and
subsequently adding an inorganic filler (C).

14. Moldings produced by melt-molding a composition as described in claim 1.

15. Shock absorbing members produced by melt-molding the composition as described in claim 1.

16. The shock absorbing members as described in claim 15 in a shape of either a square prism or a round bar.

17. The shock absorbing members as described in claim 15 adapted for use as interior or exterior members of automobiles.

18. The shock absorbing members as described in claim 17 adapted for use as crush boxes, air bag parts, pillars, bumpers, fenders, or door panels.

* * * * *